(12) United States Patent
Malakhov et al.

(10) Patent No.: US 8,623,419 B2
(45) Date of Patent: Jan. 7, 2014

(54) TECHNOLOGY FOR PREPARATION OF MACROMOLECULAR MICROSPHERES

(75) Inventors: Michael P. Malakhov, San Francisco, CA (US); Fang Fang, Rancho Santa Fe, CA (US)

(73) Assignee: Ansun Biopharma, Inc., San Diego, CA (US)

( * ) Notice: Subject to any disclaimer, the term of this patent is extended or adjusted under 35 U.S.C. 154(b) by 0 days.

(21) Appl. No.: 13/289,644

(22) Filed: Nov. 4, 2011

(65) Prior Publication Data

US 2012/0116062 A1 May 10, 2012

Related U.S. Application Data

(63) Continuation of application No. 12/633,773, filed on Dec. 8, 2009, now abandoned, which is a continuation of application No. 11/657,812, filed on Jan. 24, 2007, now abandoned.

(60) Provisional application No. 60/762,002, filed on Jan. 24, 2006.

(51) Int. Cl.
*A61K 38/43* (2006.01)
*A61K 9/14* (2006.01)
*A61K 9/19* (2006.01)

(52) U.S. Cl.
USPC ............. 424/499; 424/94.1; 514/21.2

(58) Field of Classification Search
None
See application file for complete search history.

(56) References Cited

U.S. PATENT DOCUMENTS

| | | | |
|---|---|---|---|
| 3,439,089 A | 4/1969 | Cherkas et al. | 514/159 |
| 5,033,252 A | 7/1991 | Carter | 53/425 |
| 5,052,558 A | 10/1991 | Carter | 206/439 |
| 5,145,702 A | 9/1992 | Stark et al. | 426/531 |
| 5,323,907 A | 6/1994 | Kalvelage | 206/531 |
| 5,981,719 A | 11/1999 | Woiszwillo et al. | 530/410 |
| 6,051,256 A | 4/2000 | Platz et al. | 424/489 |
| 6,063,910 A | 5/2000 | Debenedetti et al. | |
| 6,090,925 A | 7/2000 | Woiszwillo et al. | 530/410 |
| 2002/0142985 A1 | 10/2002 | Dwek et al. | |
| 2005/0004020 A1 | 1/2005 | Yu et al. | 514/12 |
| 2005/0112751 A1 | 5/2005 | Fang et al. | 435/206 |
| 2005/0234114 A1 | 10/2005 | Lee | 514/365 |
| 2007/0207210 A1 | 9/2007 | Brown et al. | |

FOREIGN PATENT DOCUMENTS

| | | |
|---|---|---|
| CN | 1729013 | 2/2006 |
| EP | 0542314 | 5/1993 |
| WO | WO9420856 | 9/1994 |
| WO | 98/06279 | 2/1998 |
| WO | 01/28524 | 4/2001 |
| WO | 2004/047735 | 6/2004 |
| WO | WO2005/035088 | 4/2005 |
| WO | 2006/031291 | 3/2006 |

OTHER PUBLICATIONS

US 5,849,884, 11/09/99, Woiszwillo et al (withdrawn).
Agrawal et al., "Basis of rise in intracellular sodium in airway hyper-responsiveness and asthma," Lung, 183:375-387, (2005).
Alcock, R., et al., "Modifying the release of leuprolide from spray dried OED microparticles," Journal of Control Release, 82(2-3):429-440, (2002).
Barbey-Morel, C.L., et al., "Role of respiratory tract proteases in infectivity of influenza A virus," Journal of Infectious Diseases, 155:667-672, (1987).
Bot A.I, et al., "Novel lipid-based hollow-porous microparticles as a platform for immunoglobulin delivery to the respiratory tract," Pharmaceutical Research, 17(3):275-283, (2000).
Cryan S.A., "Carrier-based strategies for targeting protein and peptide drugs to the lungs," American Association of Pharmaceutical Scientists PharmSci AAPS [electronic resource], 7(1):E20-E41, (2005).
Edwards D.A. et al., "Large porous particles for pulmonary drug delivery," Science, 276(5320):1868-1871, (1997).
Garcia-Contreras, L, et al., "Evaluation of novel particles as pulmonary delivery systems for insulin in rats," American Association of Pharmaceutical Scientists PharmSci AAPS [electronic resource], 5(2):E9, (2003).
Goger, B., et al., "Different affinities of glycosaminoglycan oligosaccharides for monomeric and dimeric interleukin-8: a model for chemokine regulation at inflammatory sites," Biochemistry, 41:1640-1646, (2002).
Grenha A, et al., "Microencapsulated chitosan nanoparticles for lung protein delivery," European Journal of Pharmaceutical Sciences, 25(4-5):427-437, (2005).
Huntington, J.A., et al., "Structure of a serpin-protease complex shows inhibition by deformation," Nature, 407:923-926, (2000).
Ito, T., "Interspecies transmission and receptor recognition of influenza A viruses," Microbiology and Immunology, 44:423-430, (2000).
Laube, B.L., "The expanding role of aerosols in systemic drug delivery, gene therapy, and vaccination," Respiratory Care, 50(9):1161-1176, (2005).
Le Calvez, H., et al., "Biochemical prevention and treatment of viral infections—a new paradigm in medicine for infectious diseases," Virology Journal, 1:12, (2004).
LeBlond, J., et al., "The serpin proteinase inhibitor 8: an endogenous furin inhibitor released from human platelets," Thrombosis and Haemostasis, 95:243-252, (2006).

(Continued)

*Primary Examiner* — Marianne P Allen
(74) *Attorney, Agent, or Firm* — Fish & Richardson P.C.

(57) ABSTRACT

Microspheres are produced by contacting an aqueous solution of a protein or other macromolecule with an organic solvent and a counterion, and chilling the solution. The microspheres are useful for preparing pharmaceuticals of defined dimensions.

11 Claims, No Drawings

(56) References Cited

OTHER PUBLICATIONS

Lee, M.K. and A.D. Lander, "Analysis of affinity and structural selectivity in the binding of proteins to glycosaminoglycans: development of a sensitive electrophoretic approach," Proceedings of the National Academy of Sciences of the United States of America, 88:2768-2772, (1991).
LiCalsi, C., et al., "A powder formulation of measles vaccine for aerosol delivery," Vaccine, 19(17-19):2629-2636, (2001).
Maa, Y.F., et al., "Spray-drying of air-liquid interface sensitive recombinant human growth hormone," Journal of Pharmaceutical Sciences, 87(2):152-159, (1998).
Maa Y.F., et al., "Protein inhalation powders: spray drying vs spray freeze drying," Pharmaceutical Research, 16(2):249-254, (1999).
Maa Y.F., et al., "Biopharmaceutical powders: particle formation and formulation considerations," Current Pharmaceutical Biotechnology, 1(3):283-302, (2000).
Malakhov, M.P., et al., "Sialidase fusion protein as a novel broad-spectrum inhibitor of influenza virus infection," Antimicrobial Agents and Chemotherapy, 1470-1479, (2006).
McKenna, B.J., et al., "Micrometer-sized spherical assemblies of polypeptides and small molecules by acid-base chemistry," Angewandte Chemie, 43(42):5652-5655, (2004).
*NexBio Featured by NIH News Article: New Drugs Against Flu—Seal off* (articlecanbefoundat:www3.niaid.nih.gov/news/focuson/flu/research/treatment/chen_newdrugs.htm) (accessed on Jun. 12, 2007) (2004).
Oh, M. and C.A. Mirkin, M, "Chemically tailorable colloidal particles from infinite coordination polymers," Nature, 438(7068):651-654, (2005).
Pages THER-1 to THER-28 of The Merck Index, 12th Edition, Merck & Co. Rahway, N.J. (1996).
Pfutzner, A., et al., "Pilot study with technosphere/PTH(1-34)—a new approach for effective pulmonary delivery of parathyroid hormone (1-34)," Hormone and Metabolic Research, 35(5):319-323, (2003).
Potier, M., et al., "Fluorometric assay of neuraminidase with a sodium (4-methylumbelliferyl-alpha-D-N-acetylneuraminate) substrate," Analytical Biochemistry, 94:287-296, (1979).
Sellers, S.P., et al., "Dry powders of stable protein formulations from aqueous solutions prepared using supercritical CO(2)-assisted aerosolization," Journal of Pharmaceutical Sciences, 90(6):785-797, (2001).
Shak, S., et al., "Recombinant human DNase I reduces the viscosity of cystic fibrosis sputum," Proceedings of the National Academy of Sciences of the United States of America, 87:9188-9192 (1990).
Sinha, V.R., et al, "Biodegradable microspheres for protein delivery," Journal of Controlled Release, 90(3): 261-280, (2003).
Smyth, H. and A.J. Hickey, "Carriers in drug powder delivery. Implications for inhalation system design," American Journal of Drug Delivery, 3(2):117-132, (2005).
Sprecher, C.A., et al., "Molecular cloning, expression, and partial characterization of two novel members of the ovalbumin family of serine proteinase inhibitors," Journal of Biological Chemistry, 270:29854-29861, (1995).
Tashiro, M., et al., "Inhibitory effect of a protease inhibitor, leupeptin, on the development of influenza pneumonia, mediated by concomitant bacteria," Journal of General Virology, 68:2039-2043, (1987).
Taylor, G. and M. Gumbleton, "Aerosols for Macromolecule Delivery: Design Challenges and Solutions," American Journal of Drug Delivery, 2(3):143-155, (2004).
Vanbever, R, et al., "Formulation and physical characterization of large porous particles for inhalation," Pharmaceutical Research, 16(11):1735-1742, (1999).
Varki, A., "Selectins and other mammalian sialic acid-binding lectins," Current Opinion in Cell Biology, 4:257-266, (1992).
Weisgraber, K.H., et al., "Human apolipoprotein E. Determination of the heparin binding sites of apolipoprotein E3," Journal of Biological Chemistry, 261:2068-2076, (1986).
Witt, D.P. and A.D. Lander, "Differential binding of chemokines to glycosaminoglycan subpopulations," Current Biology, 4:394-400, (1994).
Zhirnov, O.P., et al., "Cleavage of Influenza A Virus Hemagglutinin in Human Respiratory Epithelium Is Cell Associated and Sensitive to Exogenous Antiproteases," Journal of Virology, 76:8682-8689, (2002).
Zhirnov, O.P., et al., "Protective effect of protease inhibitors in influenza virus infected animals," Archives of Virology, 73:263-272, (1982).

TECHNOLOGY FOR PREPARATION OF MACROMOLECULAR MICROSPHERES

RELATED APPLICATIONS

This application is a continuation of U.S. application Ser. No. 12/633,773, filed Dec. 8, 2009, now abandoned, which claims priority to U.S. application Ser. No. 11/657,812, filed Jan. 24, 2007, now abandoned, which claims priority to U.S. provisional application No. 60/762,002, filed Jan. 24, 2006. The prior applications are hereby incorporated by reference in their entireties.

This application also is related to International PCT application Application Serial No. PCT/US2007/001914, filed 24 Jan. 2007. This application also is related to published U.S. application Serial Nos. US20050004020 A1 and US20050112751 A1. Each of these applications is incorporated by reference in its entirety.

FEDERALLY SPONSORED RESEARCH OR DEVELOPMENT

This invention was made with Government support under Grant No. 5R43AI056786 awarded by the Department of Health and Human Services, National Institutes of Health. The Government has certain rights in this invention.

BACKGROUND

The administration of proteins to animals, including humans, in nutritional supplements or as therapeutics has been known for some time. Proteins for therapeutic or nutritional administration generally are available either as (1) concentrates or powders that are administered directly or are reconstituted in a liquid of choice prior to use; or (2) liquid formulations.

The preparation and delivery of therapeutic proteins of interest in powder or particle form is an area of concentrated research and development activity in the pharmaceutical industry. For therapeutic efficacy, it is desirable to have a uniform formulation. For example, for pulmonary administration, the protein ideally is prepared in the form of discrete microspheres, which are solid or semi-solid particles having a diameter of between 0.5 and 5.0 microns. It also is desirable for the particles to have a protein content that is as high as possible and that maintains its activity for concentrated delivery and therapeutic efficacy.

Previous methods of producing protein microparticles or nanoparticles have involved complex steps, such as blending with organic polymers and/or forming a lattice array with polymers; spray drying, spray freeze-drying or supercritical fluid antisolvent techniques that use specialized and complex equipment; or lyophilization followed by pulverization or milling that often results in non-uniform particles that must further be sorted. Often previous methods of producing solid protein formulations involve processing steps, such as heating, that denature the protein and compromise its activity. In addition, some methods do not provide high recovery from solution into the solid formulation.

Accordingly, there is a need for a method for producing protein and other macromolecular microparticles that does not require complex or specialized equipment and that produces uniform-sized microparticles for delivery. There further is a need for a method of producing microparticles that contain high concentrations of the protein or macromolecule relative to other components, that are stable and maintain their activity for long periods of time when stored at ambient temperature and that do not contain a significant amount of denatured protein. There also is a need for a method of producing microparticles of proteins and other macromolecules wherein substantially all of the protein or macromolecule in the starting material is recovered in the microparticle formulation, with minimal loss. There also is a need for microparticles of proteins or other macromolecules containing these properties for administration, for example, as a therapeutic or nutritional supplement.

SUMMARY

Provided herein are methods for producing protein and other macromolecular microparticles that do not require complex or specialized equipment and that produces uniform-sized microparticles for delivery; methods for producing microparticles that contain high concentrations of protein or macromolecule relative to other components, that are stable and maintain their activity for long periods of time when stored at ambient temperature and that do not contain a significant amount of denatured protein. Also provide are methods for producing microparticles of proteins and other macromolecules where substantially all of the protein or macromolecule in the starting material is recovered in the microparticle formulation, with minimal loss. Also provided are microparticles of proteins and other macromolecules containing these properties for administration, for example, as a therapeutic or nutritional supplement.

The methods of making a protein-based composition, the protein-based compositions themselves, combinations, articles of manufacture provided below are characterized by a variety of component ingredients, steps of preparation, and biophysical, physical, biochemical and chemical parameters. As would be apparent to one of skill in the art, the compositions and methods provided herein include any and all permutations and combinations of the ingredients, steps and/or parameters described below.

Provided herein are methods of making a protein-based composition. The method provided herein can be used to make compositions from other macromolecules besides proteins, including DNA, RNA, PNA, lipids, oligosaccharides and combinations thereof.

The methods provided herein can include the steps of:
a) adding a counterion to a solution containing the protein in an aqueous solvent;
b) adding an organic solvent to the solution; and
c) gradually cooling the solution to a temperature below about 25° C., whereby a composition containing microparticles comprising the protein is formed, wherein steps a), b) and c) are performed simultaneously, sequentially, intermittently, or in any order.

In one embodiment, the steps are performed sequentially a), b) and then c). In another embodiment, the method of making a protein-based composition includes performing steps a) and b) simultaneously or sequentially in any order, followed by step c).

The resulting microparticles can be obtained by precipitation, by phase separation or by colloid formation. In some aspects, the methods provided herein further comprise separating the microparticles from the solution to remove components other than the microparticles. This separation step can be performed following the above-mentioned step c). The separation can be effected by, for example, sedimentation, filtration and/or freeze-drying.

The methods provided herein include the addition of an organic solvent to an aqueous solvent containing the protein. In certain embodiments, the organic solvent in miscible or partially miscible with the aqueous solvent. In further embodiments of the methods provided herein, the organic solvent is selected from among aliphatic alcohols, aromatic alcohols, chloroform, dimethyl chloride, polyhydric sugar alcohols, aromatic hydrocarbons, aldehydes, ketones, esters, ethers, dioxanes, alkanes, alkenes, conjugated dienes, dichloromethane, acetonitrile, ethyl acetate, polyols, polyimides, polyesters, polyaldehydes and mixtures thereof. For example, where the organic solvent is an aliphatic alcohol, the organic solvent can be isopropanol. The amount of organic solvent added can vary in the methods provided herein. For example, the amount of organic solvent added can be from about 0.1% or 0.1% to about 50% or 50% v/v. In other embodiments, the amount of organic solvent added is from about 1% or 1% to about 30% or 30% v/v, from about 5% or 5% to about 30% or 30% v/v, from about 10% or 10% to about 30% or 30% v/v or from about 15% or 15% to about 20% or 20% v/v.

The counterion used in the methods provided herein can be an anionic compound, a cationic compound and/or a zwitterionic compound. For example, when the counterion is an anionic compound, the counterion can be glycine, sodium citrate, sodium sulfate, zinc sulfate, magnesium sulfate, potassium sulfate or calcium sulfate. The concentration of organic solvent added to the solution can vary in the method provided herein. For example, the concentration of counterion added to the solution can be from about 0.1 mM or 0.1 mM to about 100 mM or 100 mM. In other embodiments, the concentration of counterion added to the solution is from about 0.2 mM or 0.2 mM to about 50 mM or 50 mM, from about 0.3 mM or 0.3 mM to about 30 mM or 30 mM, from about 0.5 mM or 0.5 mM to about 20 mM or 20 mM or from about 1 mM or 1 mM to about 10 mM or 10 mM. In a particular embodiment, the concentration of counterion added to the solution is about 5 mM or 5 mM.

In one aspect of the methods provided herein, the pH of the solution that contains the protein is at or below the pI of the protein. In some aspects, the pH of the solution is from about 4.0 or 4.0 to about 9.0 or 9.0. In other aspects, the pH of the solution is from about 4.5 or 4.5 to about 8.0 or 8.0, from about 4.5 or 4.5 to about 6.5 or 6.5, or from about 4.5 or 4.5 to about 5.5 or 5.5.

The protein that is used in the methods provided herein to make a protein-based composition can be selected from among sialidases, sialidase fusion proteins, proteases, protease inhibitors, cytokines, insulin, human growth hormone, calcitonin, recombinant human DNase, interferons and parathyroid hormone. In one embodiment, where the protein is a protease inhibitor, the protein is human protease inhibitor 8 (PI8). In another embodiment, the protein is a sialidase fusion protein. In some aspects where the protein is a sialidase fusion protein, the sialidase fusion protein contains a catalytic domain of a sialidase and an anchoring domain, wherein the catalytic domain of the sialidase is the only portion of the sialidase in the sialidase fusion protein. The sialidase can be, for example, an *Actinomyces viscosus* sialidase, a *Clostridium perfringens* sialidase, an *Arthrobacter ureafaciens* sialidase, a *Micromonospora viridifaciens* sialidase, a human Neu2 sialidase or a human Neu4 sialidase.

In one aspect, where the sialidase is an *Actinomyces viscosus* sialidase, the amino acid sequence of the catalytic domain contains the sequence of amino acid residues beginning at any of the amino acids from amino acid 270 to amino acid 290 and ending at any of the amino acids from amino acid 665 to amino acid 901 of the sequence of amino acids set forth in SEQ ID NO. 1. For example, in one embodiment, the sequence of the sialidase catalytic domain contains the sequence of amino acid residues set forth in SEQ ID NO:2. In another embodiment, the sequence of the catalytic domain comprises the sequence of amino acid residues beginning at amino acid 274 and ending at amino acid 681 of the sequence of amino acids set forth in SEQ ID NO. 1. In a different embodiment, the sequence of the catalytic domain comprises the sequence of amino acid residues beginning at amino acid 274 and ending at amino acid 666 of the sequence of amino acids set forth in SEQ ID NO. 1. In another embodiment, the sequence of the catalytic domain comprises the sequence of amino acids beginning at amino acid 290 and ending at amino acid 681 of the sequence of amino acids set forth in SEQ ID NO. 1.

In one aspect, where the protein that is used in the methods provided herein to make a protein-based composition is a sialidase fusion protein that contains an anchoring domain, the anchoring domain is a glycosaminoglycan (GAG)-binding domain. In a further aspect, the GAG-binding domain is selected from among the GAG-binding domain of human platelet factor 4, the GAG-binding domain of human interleukin 8, the GAG-binding domain of human antithrombin III, the GAG-binding domain of human apoprotein E, the GAG-binding domain of human angio-associated migratory protein and the GAG-binding domain of human amphiregulin. In particular embodiments, the amino acid sequence of the GAG-binding domain contains the sequence of amino acid residues set forth in SEQ ID NO:3, SEQ ID NO:4, SEQ ID NO:5, SEQ ID NO:6, SEQ ID NO:7 or SEQ ID NO:8.

In some aspects where the protein that is used in the methods provided herein to make a protein-based composition is a sialidase fusion protein, the amino acid sequence of the sialidase fusion protein contains the sequence of amino acid residues set forth in SEQ ID NO:9, the sequence of amino acid residues set forth in SEQ ID NO:10, the sequence of amino acid residues set forth in SEQ ID NO:11, the sequence of amino acid residues set forth in SEQ ID NO:12, the sequence of amino acid residues set forth in SEQ ID NO:13, the sequence of amino acid residues set forth in SEQ ID NO:14, or the sequence of amino acid residues set forth in SEQ ID NO:17.

In one aspect, the amount of protein in the microparticles produced by the methods provided herein, relative to the total amount of protein in the solution of step a) is about 80% or 80% to greater than about 99% or 99%. In another aspect, the resulting microparticle composition produced by the methods provided herein can further comprise acid-resistant coating agents, protease-resistant coating agents, enteric coating agents, bulking agents, excipients, inactive ingredients, stability enhancers, taste and/or odor modifiers or masking agents, vitamins, therapeutic agents, anti-oxidants, immunomodulators, trans-membrane transport modifiers, anti-caking agents, chitosans or flowability enhancers.

The solution and/or the resulting composition of the methods provided herein can, in one aspect, further comprise an active agent. In some embodiments, the active agent is selected from among antidiabetics, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides and polysaccharides. In another embodiment, the active agent is a nutritional supplement.

The methods provide herein involve gradually cooling the solution to a temperature below about 25° C. In one embodiment, the temperature is between about 4° C. to about −45° C. In another embodiment, the temperature is between about 2° C. to about −20° C. In a further embodiment, the temperature is between about 2° C. to about −15° C. In another embodiment, the temperature is between about 0° C. or 0° C. to about −2° C. or −2° C. to from about −15° C. or −15° C. to about −20° C. or −20° C. The gradual cooling can be performed at a variety of rates. For example, cooling can be effected at a rate of from about 0.01° C./min or 0.01° C./min to about 20° C./min or 20° C./min. In other embodiments, the gradual cooling is at a rate of from about or at 0.05° C./min or about or at 0.1° C./min to about or at 10° C./min or about or at 15° C./min, about or at 0.2° C./min to about or at 5° C./min, or about or at 0.5° C./min to about or at 2° C./min. In a particular embodiment, the gradual cooling is performed at a rate of about or at 1° C./min.

In one aspect, the size of the microparticles produced by the methods provided herein is from about 0.001 μm or 0.001 μm to about 50 μm or 50 μm. In other embodiments, the size of the microparticles is from about 0.3 μm or 0.3 μm to about 30 μm or 30 μm, from about 0.5 μm or 0.5 μm to about 10 μm or 10 μm, from about 0.5 μm or 0.5 μm to about 5.0 μm or 5.0 μm, from about 1.0 μm or 1.0 μm to about 5.0 μm or 5.0 μm or from about 1.0 μm to about 2.0, 3.0, 4.0 or 5.0 μm.

In some aspects of the methods provided herein, the resulting protein-based composition has a shelf life of from about one week to about 1 month, from about 1 month to about six months, from about six months to about one year, from about 1 year to about 2 years, or from about 2 years to about 5 years at a temperature of about 55° C., 50° C., 45° C., 44° C., 42° C., 40° C., 39° C., 38° C., 37° C. or below. 54. In another aspect, the moisture content of the microparticles is adjusted whereby at least about 90% of the activity of the protein is retained after storage for about six months to about 1 year at a temperature of about 25° C. In another aspect, the moisture content of the microparticles is adjusted whereby at least about 90% of the microparticles are not aggregated after storage for about six months to about 1 year at a temperature of about 25° C.

In a certain aspect of the methods provided herein, the protein is a fusion protein containing a sialidase catalytic domain and an anchoring domain, wherein the sialidase catalytic domain is the only portion of the sialidase in the fusion protein, the organic solvent is added in an amount of about 5% or 5% to about 20% or 20% v/v, the counterion is added in an amount of about 1 mM or 1 mM to about 5 mM or 5 mM, and the pH of the solution is adjusted to about 4.5 or 4.5 to about 5.5 or 5.5. In one embodiment of this aspect, the sialidase catalytic domain is from *Actinomyces viscosus* and the anchoring domain is the GAG-binding domain from human amphiregulin. Further still, the pH is about 5.0 and/or the counterion is selected from among glycine, sodium citrate, sodium sulfate, zinc sulfate, magnesium sulfate, potassium sulfate or calcium sulfate. In another embodiment of this aspect, the organic solvent is isopropanol. In one embodiment of this aspect, the resulting composition contains the microparticles containing the protein as the only active ingredient (i.e. consists essentially of). In another embodiment, the method includes separating the microparticles from the solution to remove components other than the microparticles, such as by sedimentation, filtration and/or freeze-drying. In some embodiments of this aspect, the moisture content of the microparticles is from about 6% to about 12%, or from about 7% to about 10.5%.

Provided herein are compositions containing microparticles of a sialidase or a sialidase fusion protein. Where the protein is a sialidase fusion protein, the sialidase fusion protein can comprise a catalytic domain of a sialidase and an anchoring domain. In some aspects, the sialidase in the composition is an *Actinomyces viscosus* sialidase, a *Clostridium perfringens* sialidase, an *Arthrobacter ureafaciens* sialidase, a *Micromonospora viridifaciens* sialidase, a human Neu2 sialidase, or a human Neu4 sialidase.

In one aspect, where the sialidase of the composition is an *Actinomyces viscosus* sialidase, the amino acid sequence of the catalytic domain comprises the sequence of amino acids beginning at any of the amino acid residues from amino acid 270 to amino acid 290 and ending at any of the amino acid residues from amino acid 665 to amino acid 901 of the sequence of amino acids set forth in SEQ ID NO. 1. For example, the sequence of the catalytic domain can comprise the sequence of amino acids beginning at amino acid 274 and ending at amino acid 681 of the sequence of amino acids set forth in SEQ ID NO. 1, the sequence of amino acids beginning at amino acid 290 and ending at amino acid 666 of the sequence of amino acids set forth in SEQ ID NO. 1 or the sequence of amino acids beginning at amino acid 290 and ending at amino acid 681 of the sequence of amino acids set forth in SEQ ID NO. 1. In another embodiment, the sequence of the sialidase catalytic domain comprises the sequence of amino acids set forth in SEQ ID NO:2.

In one aspect, where the composition comprising microparticles of a sialidase fusion protein, the anchoring domain of the sialidase fusion protein is a glycosaminoglycan (GAG)-binding domain. In a further aspect, the GAG-binding domain is selected from among the GAG-binding domain of human platelet factor 4, the GAG-binding domain of human interleukin 8, the GAG-binding domain of human antithrombin III, the GAG-binding domain of human apoprotein E, the GAG-binding domain of human angio-associated migratory protein and the GAG-binding domain of human amphiregulin. In particular embodiments, the amino acid sequence of the GAG-binding domain contains the sequence of amino acid residues set forth in SEQ ID NO:3, SEQ ID NO:4, SEQ ID NO:5, SEQ ID NO:6, SEQ ID NO:7 or SEQ ID NO:8.

The sialidase fusion proteins of the compositions provided herein can contain, for example, the sequence of amino acid residues set forth in SEQ ID NO:9, SEQ ID NO:10, SEQ ID NO:11, SEQ ID NO:12, SEQ ID NO:13, SEQ ID NO:14, or SEQ ID NO:17.

The amount of protein in the microparticles of the compositions provided herein can vary. For example, the amount of protein in the microparticles can be from about 60% to greater than about 99% w/w. In one embodiment, the amount of protein in the microparticles is from about 65% to about 90% w/w. In another embodiment, the amount of protein in the microparticles is from about 70% to about 85%, 86%, 87%, 88%, 89% or 90% w/w. The amount of protein in the microparticles of the compositions provided herein also can be from about 90% to about 99% w/w.

The microparticles in the compositions provided herein can further contain acid-resistant coating agents, protease-resistant coating agents, enteric coating agents, bulking agents, excipients, inactive ingredients, stability enhancers, taste and/or odor modifiers or masking agents, vitamins, therapeutic agents, anti-oxidants, immuno-modulators, trans-membrane transport modifiers, anti-caking agents, chitosans or flowability enhancers.

In one aspect, the compositions provided herein can further contain an active agent. The active agent can be a nutritional supplement, antidiabetics, anticonvulsants, analgesics, anti-parkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides and polysaccharides.

The compositions provided herein can have a shelf-life of varying length. In one aspect, the shelf life is from about one week to about 1 month, from about 1 month to about six months, from about six months to about one year, from about 1 year to about 2 years, or from about 2 years to about 5 years at a temperature of about 55° C., 50° C., 45° C., 44° C., 42° C., 40° C., 39° C., 38° C., 37° C. or below. In a certain aspect, the moisture content of the microparticles is adjusted whereby at least about 90% of the activity of the protein is retained after storage for about six months to about 1 year at a temperature of about 25° C.

The microparticles in the compositions provided herein can further contain a counterion, such as, for example, an anion, a cation, or a zwitterion. In certain embodiments, the counterion is selected from among glycine, sodium citrate, sodium sulfate, zinc sulfate, magnesium sulfate, potassium sulfate or calcium sulfate. The amount of counterion in a microparticle can be varied. For example, the amount of counterion in the microparticles can be from about 0.5% or 0.5% to about 5% or 5% w/w, from about 0.5% or 0.5% to about 2% or 2% w/w, or from about 1% or 1% to about 2% or 2% w/w.

In some embodiments, the moisture content of the microparticles in the compositions provided herein is from about 6% or 6% to about 12% or 12%, or from about 7% or 7% to about 10.5% or 10.5%.

The compositions provided herein can be formulated for a variety of modes of administration. For example, the compositions can be orally e.g. by ingestion, intravenously, intranasally, parenterally, subcutaneously or intramuscularly administered. The compositions also can formulated for pulmonary or ophthalmic administration. In a certain aspect, the composition provided herein is for inhalation.

The compositions provided herein can be formulated as tablets, caplets, gels, vials, pre-filled syringes, inhalers, electrostatic devices and other devices for delivery. The delivery dosage of the compositions can be from between about 0.5 mg protein per dose to about 100 mg protein per dose, or about 0.75 mg, 1 mg, 1.5 mg, 2 mg, 3 mg, 5 mg, 10 mg, 15 mg, 20 mg, 30 mg, 40 mg, 45 mg, 50 mg, 55 mg or 60 mg protein per dose. The frequency of administration of a dose, for example, for the treatment or prophylaxis of influenza, can be from three or more times a day, to two times a day, to once a day, to two times a week, to once a week, to once every two weeks or less frequent than once every two weeks. For prophylaxis, the administration generally can be of the order of about once every two weeks or less frequent, such as once every three weeks or once every four weeks or longer.

The size of the microparticles in the compositions provided herein can vary. For example, the size of the microparticles can be from about 0.001 µm or 0.001 µm to about 50 µm or 50 µm. In certain embodiments, the size of the microparticles is from about 0.3 µm or 0.3 µm to about 30 µm or 30 µm, from about 0.5 µm or 0.5 µm to about 10 µm or 10 µm, from about 0.5 µm or 0.5 µm to about 5.0 µm or 5.0 µm, from about 1.0 µm or 1.0 µm to about 5.0 µm or 5.0 µm or from about 1.0 µm to about 2.0, 3.0, 4.0 or 5.0 µm.

Also provided herein are articles of manufacture that contain a composition containing microparticles of a sialidase or a sialidase fusion protein, a packaging material for the composition and a label that indicates that the composition is for a therapeutic indication. In one embodiment, the therapeutic indication is influenza. The article of manufacture also can contain an inhaler for pulmonary administration of the composition. In certain embodiments, the inhaler is a dry powder inhaler, a metered dose inhaler or an electrostatic delivery device.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, the term "macromolecule" is used to mean a molecule composed of two or more monomeric subunits, or derivatives thereof, which are linked by a bond, or any macromolecule that can form tertiary structure. A macromolecule can be, for example, a polynucleotide, a nucleic acid molecules including DNA, RNA and peptide nucleic acid (PNA) a polypeptide, a protein, a carbohydrate, or a lipid, or derivatives or combinations thereof, for example, a nucleic acid molecule containing a peptide nucleic acid portion or a glycoprotein, respectively. The methods, compositions, combinations, kits and articles of manufacture provided herein, although described with reference to proteins, can be adapted for use with other macromolecules as defined and provided herein.

The term "substantially" or "substantial" as used herein generally means at least about 60% or 60%, about 70% or 70%, or about or at 75%, 80%, 85%, 90%, 95%, 96%, 97%, 98%, 99% or higher relative to a reference such as, for example, a nucleic acid or protein sequence or the original composition of an entity. Thus, a composition containing microparticles separated from "substantially" all other contaminants and/or ingredients including counterions, salts and solvents from the cocktail solution means that at least about 60% or 60%, about 70% or 70%, or about or at 75%, 80%, 85%, 90%, 95%, 96%, 97%, 98%, 99% or higher amounts of contaminants and/or reagents have been removed from the cocktail solution in which the microparticles are formed. The term "substantially identical" or "substantially homologous"

or similar varies with the context as understood by those skilled in the relevant art and generally means at least about 60% or 60%, about 70% or 70%, or about or at 75%, 80%, 85%, 90%, 95%, 96%, 97%, 98%, 99% or higher identity.

The term "consists essentially of" or "consisting essentially of" as used herein refers to an entity from which substantially all other components/ingredients that are not associated with the entity or its properties have been removed or separated from the entity. Thus, a composition "consisting essentially of" microparticles means that all other ingredients such as contaminants and solvents have substantially been removed from the solution/suspension containing the microparticles.

The term "microparticle" as used herein is interchangeable with "microsphere" and refers to particles in the size range (average length, width or diameter) of about or at 0.001 micron (μm) to about or at 500 microns that contain a macromolecule and deliver an agent of interest, such as a drug or nutritional supplement, to a subject. The agent can be the macromolecule, for example, a protein, nucleic acid, lipid or polysaccharide, or the macromolecule forming the microparticle can be a carrier for the active agent, such as a drug or a nutritional supplement. The microparticles also can contain synthetic macromolecules including polymers, such as polyethylene glycol (PEG), polylactic acid (PLA), polylactic-co-glycolic acid (PLGA), and natural polymers such as albumin, gelatin, chitosan and dextran. The "microparticles" as described herein can contain and can be made from a particular natural or synthetic macromolecule alone, or from more than one type of the same natural or synthetic macromolecule (e.g., more than one type of protein), or from combinations of more than one different type of natural or synthetic macromolecule (e.g., a protein and a nucleic acid or a protein and a synthetic polymer).

The term "microparticle" as used herein also generally refers to a particle that is not a solid form of the entire solution from which it is produced, although frozen and/or dried particles of a solution containing macromolecules also are contemplated herein. Rather, the microparticle as used herein generally is an assembly of a fraction of the components of a solution, including salts, counterions, solvents and other ingredients, that is formed by a process including, but not limited to, precipitation, sedimentation, phase separation and colloid formation.

The term "precipitation" as used herein refers to a process whereby a solute or solutes of interest in a solution, such as the components of a microparticle, no longer stay in solution and form a phase that is distinct from the solvent or solvents that were used to form the solution. Precipitation of a microparticle and controlling the size of the precipitated microparticle can be accomplished by a variety of means including, but not limited to, adjusting temperature, ionic strength, pH, dielectric constant, counterion concentration, organic solvent concentration, the addition of polyelectrolytes or polymers, surfactants, detergents, or a combination thereof.

The term "phase separation" as used herein refers to the transformation of a single homogeneous phase, such as a solution, into two or more phases, such as a suspension of a solid particle in a solvent or solution.

The term "sedimentation" as used herein refers to the motion of particles, such as microparticles, which are in a suspension in a liquid or which are formed in a solution in response to an external force such as gravity, centrifugal force or electric force.

The term "solution" is used interchangeably with "cocktail solution" herein and refers to a homogeneous mixture of two or more ingredients in a single phase, solid, liquid, or gas, where the distinct ingredients only are recognizable at the molecular level. The solution can be a liquid in which one or more solutes, such as salts, are dissolved in a solvent, such as water or alcohol, or dissolved in a mixture of miscible solvents, such as a mixture of water and ethyl alcohol. The solution also can be a frozen form of a liquid solution.

The term "miscible" as used herein refers to the ability of one or more components, such as liquids, solids and gases, to mix together to form a single, homogeneous phase. Thus, two liquids are miscible if they can be mixed to form a single, homogenous liquid whose distinct components are recognized only at the molecular level. When components are "partially miscible," it means that they can be mixed to form a single homogenous phase in a certain concentration range, but not at other concentration ranges. As used herein, when a solvent is "partially miscible" with another solvent, it means that it is miscible at a concentration of about or at 50%, 45%, 40%, 35%, 30%, 25%, 20%, 15%, 10%, 9%, 8%, 7%, 6%, 5%, 4%, 3%, 2%, 1%, 0.5% or below volume/volume (v/v), when mixed with the other solvent.

As used herein, "immiscible" means that when two or more components, such as liquids, solids or gases are mixed, they form more than one phase. For example, when an organic solvent is immiscible with an aqueous solvent (e.g., hexane and water), the organic solvent is visible as a distinct layer that does not mix with the layer of aqueous solvent.

As used herein, the term "polypeptide," means at least two amino acids, or amino acid derivatives, including mass modified amino acids and amino acid analogs, that are linked by a peptide bond, which can be a modified peptide bond. The terms "polypeptide," "peptide" and "protein" are used essentially synonymously herein, although the skilled artisan will recognize that peptides generally contain fewer than about fifty to about one hundred amino acid residues, and that proteins often are obtained from a natural source and can contain, for example, post-translational modifications.

A polypeptide or protein can be translated from a polynucleotide, which can include at least a portion of a coding sequence, or a portion of a nucleotide sequence that is not naturally translated due, for example, to it being located in a reading frame other than a coding frame, or it being an intron sequence, a 3' or 5' untranslated sequence, a regulatory sequence such as a promoter, or the like. A polypeptide also can be chemically synthesized and can be modified by chemical or enzymatic methods following translation or chemical synthesis. A polypeptide can be post-translationally modified by phosphorylation (phosphoproteins), glycosylation (glycoproteins, proteoglycans), and the like, which can be performed in a cell or in a reaction in vitro.

As used herein, the term "fusion protein" refers to a protein that is a conjugate of domains obtained from more than one protein or polypeptide. A domain can be a polypeptide tag, such as a $His_6$ tag. The conjugates can be prepared by linking the domains by chemical conjugation, recombinant DNA technology, or combinations of recombinant expression and chemical conjugation.

A variety of chemical linkers are known to those of skill in the art and include, but are not limited to, amino acid and peptide linkages, typically containing between one and about 60 amino acids, more generally between about 10 and 30 amino acids, heterobifunctional cleavable cross-linkers, including but are not limited to, N-succinimidyl (4-iodoacetyl)-aminobenzoate, sulfosuccinimidyl (4-iodoacetyl)-aminobenzoate, 4-succinimidyl-oxycarbonyl-a-(2-pyridyldithio)toluene, sulfosuccinimidyl-6-[a-methyl-a-(pyridyldithiol)-toluamido]hexanoate, N-succinimidyl-3-(–2-pyridyldithio)-propionate, succinimidyl 6[3(-(-2- pyridyldithio)-propionamido]hexanoate, sulfosuccinimidyl 6[3(-(-2-pyridyldithio)-propionamido]hexanoate, 3-(2-pyridyldithio)-propionyl hydrazide, Ellman's reagent, dichlorotriazinic acid, and S-(2-thiopyridyl)-L-cysteine.

The term "sialidase fusion protein" as used herein refers to a fusion protein in which one or more domains is a sialidase or a portion thereof that retains at least about 60% or 60%, about 70% or 70%, or about or at 75%, 80%, 85%, 90%, 95%, 96%, 97%, 98%, 99% or more of its catalytic activity. A sialidase fusion protein as used herein also can refer to a fusion protein that contains a protein or polypeptide that is substantially homolgous to a sialidase and possesses the enzymatic activity of a sialidase.

The term "catalytic domain" of a protein as used herein refers to a protein or polypeptide in which the only portion of the sequence that is substantially homologous to a sialidase is a sequence of amino acid residues that includes the domain responsible for the catalytic activity of the protein (e.g., residues 274-666 of SEQ ID NO: 1 are identified as the catalytic domain of *Actinomyces viscosus* sialidase) or catalytically active fragments thereof. The catalytic domain or catalytically active fragment thereof retains at least about 60% or 60%, about 70% or 70%, or about or at 75%, 80%, 85%, 90%, 95%, 96%, 97%, 98%, 99% or more of the catalytic activity of the protein.

As used herein, the term "flowability characteristic" refers to a property that renders the ability to "flow," where "flow" is a property that can permit a substance to be poured and to assume the shape of a container that it is poured into, without hindrance due to, for example, aggregation. Fluids generally have the property of "flow," which generally renders them deformable, i.e., they can change their shape. The term "fluid" as used herein encompasses colloids containing liquids, including emulsions, aerosols and gases. Liquids, aerosols and gases with suspensions of solid particles, such as microparticles, also are considered "fluid" as defined herein.

As used herein, an emulsion is defined as a colloid of two immiscible liquids, a first liquid and a second liquid, where the first liquid is dispersed in the second liquid.

As used herein, surfactants (or "surface-active agents") are chemical or naturally occurring entities which, when dissolved in an aqueous solution, reduce the surface tension of the solution or the interfacial tension between two or more phases in solution. The surfactant molecules generally are amphiphilic and contain hydrophilic head groups and hydrophobic tails. The surfactant molecules can act as stabilizers and/or improve flowability characteristics of the microparticles provided herein.

As used herein, a combination refers to any association between two or among more items for a purpose. For example, a combination of microparticles and an inhaler can be used for pulmonary delivery of a therapeutic agent.

As used herein, a composition refers to any mixture. It can be a solution, a suspension, liquid, powder, a paste, aqueous, non-aqueous or any combination thereof.

As used herein, a kit refers to a combination in which components are packaged optionally with instructions for use and/or reagents and apparatus for use with the combination.

As used herein, the term "enzyme" means a protein that catalyzes a chemical reaction or biological process. Enzymes generally facilitate and/or speed up such reactions and processes. In addition, enzymes generally are specific for a particular reaction or process, converting a specific set of reactants into specific products.

As used herein, the term "colloid" refers to a dispersion of solid particles, such as microparticles, in a liquid, such as the solution in which the microparticles are formed. The term "colloidal stability" refers to a colloid in which the particles are not substantially aggregated. For example, a stable colloid is one in which about 30%, 25%, 20%, 15%, 10%, 5%, 4%, 3%, 2%, 1%, 0.5% or less of the solid particles, such as microparticles, have formed aggregates.

The term "agglomerates" refers to the association of one or more particles, such as microspheres, loosely held together by van der Waals forces or surface tension or electrostatic or combinations thereof. In some instances, associations held by electrostatic forces can be defined as "Flocculates." For the purposes herein, "Agglomerates" also encompass "Flocculates". Agglomerates can generally readily be broken apart by shear forces within the air or liquid. The term "disperse" or "dispersivity" refers to the ability of the particles to "flow," i.e., the extent to which the movement is not impeded by the presence of, for example, aggregates.

The term "aggregates" refers to the association of one or more particles, such as microspheres, amorphous precipitates, crystal- or glass-like particles or combinations thereof. Aggregates generally are not easily broken apart which inhibits their ability to disperse or form homogeneous suspensions or to form aerosols with desirable properties.

The term "non-denatured" as used herein is in reference to proteins and means a conformation of a protein, i.e., its secondary structure, tertiary structure, quaternary structure or combinations thereof, which essentially is unaltered from the protein in its naturally occurring state. The terms "non-denatured" and "native" are used interchangeably herein and mean a protein that retains all or at least about 50%, 60%, 70%, 80%, 85%, 90% 91%, 92%, 93%, 94%, 95%, 96%, 97%, 98% or 99% of its length and/or natural conformation. The terms "non-denatured" or "native" as used interchangeably herein include the natural state of a protein in a cell, such as it's length and conformation including secondary, tertiary and quaternary structures. As defined herein, the "non-denatured" or "native" proteins including those in the compositions provided herein generally retain all or at least about 50%, 60%, 70%, 80%, 85%, 90%, 91%, 92%, 93%, 94%, 95%, 96%, 97%, 98% or 99% of the normal activity or function of the proteins in their natural state, e.g., as a nutrient to provide amino acid building blocks, an antioxidant, an enzyme, an antibody, a regulator of gene expression, a scaffold, etc.

As used herein, the terms "activity" or "function" are interchangeable with "biological activity" and refer to the in vivo activities of a compound, such as a protein, vitamin, mineral or drug, or physiological responses that result upon in vivo administration of a compound, composition or other mixture. Activity, thus, encompasses therapeutic effects and pharmaceutical activity of compounds, compositions and mixtures. Biological activities also can be observed in in vitro systems designed to test or use such activities.

As used herein, "functional activity" also is interchangeable with "activity," "biological activity" or "function" and refers to a polypeptide or portion thereof that displays one or more activities associated with the native or non-denatured protein. Functional activities include, but are not limited to, biological activity, catalytic or enzymatic activity, antigenicity (ability to bind to or compete with a polypeptide for binding to an anti-polypeptide antibody), immunogenicity, ability to form multimers, and the ability to specifically bind to a receptor or ligand for the polypeptide.

The term "denatured" as used herein refers to a protein that is altered from its native or non-denatured conformation, i.e., its secondary, tertiary or quaternary structure or combinations thereof. The altered conformation generally occurs by processing steps that include pasteurization, radiation, heat, chemicals, enzyme action, exposure to acids or alkalis, and ion-exchange and any combinations thereof. Denaturation of a protein generally results in diminishing all or some, generally more than 50% and at least about 70%, 80%, 85%, 90%, 91%, 92%, 93%, 94%, 95%, 96%, 97%, 98% or 99%, of the original properties including activity and function of the protein in its native or non-denatured state.

As used herein, the term "nutritional supplement" means a substance or composition that provides nutrients, including vitamins, minerals, fatty acids, amino acids, carbohydrates, enzymes, proteins, biochemicals and their metabolites, herbs and plants, to a host, such as an animal, including a human being. Nutrients that are supplied to the host through nutritional supplements can include nutrients essential for survival, good health, curing disease or preventing disease that are missing or deficient in a host's diet, and nutrients that are believed to augment good health, prevent disease or cure disease but are not considered essential for survival or good health.

As used herein, "hydrophobic" refers to a substance that is not charged or charge-polarized, or is not sufficiently charged or charge-polarized to bond with water or other polar solvents. Hydrophobic ligands can associate with each other or with other non-polar molecules or solvents in the presence of water or a polar solvent, through hydrophobic interactions. A hydrophobic ligand generally also is more soluble in non-polar solvents than in polar solvents. Examples of non-polar solvents include alkanes such as hexane, alkyl ethers such as diethyl ether, aromatic hydrocarbons such as benzene and alkyl halides such as methylene chloride and carbon tetrachloride, mono-, di- and triglycerides, fatty acids, such as oleic, linoleic, palmitic, stearic, conjugated forms thereof and their esters.

As used herein, the term "therapeutic agent" means an agent which, upon administration to a host, including humans, effectively ameliorates or eliminates symptoms or manifestations of an inherited or acquired disease or that cures said disease.

As used herein, "shelf life" or "stability" refers to the time after preparation
of the microparticle composition that the composition retains at least about or 70%, 80%, 85%, 90%, 91%, 92%, 93%, 94%, 95%, 96%, 97%, 98% or 99% of the initial protein activity that is present in the composition and other general physical characteristics of microspheres such as size, shape, and aerodynamic particle size distribution. Thus, for example, a composition that is stable for or has a shelf life of 30 days at room temperature, defined herein as range of between about 18° C. to about 25° C., 26° C., 27° C. or 28° C., would have at least about 70%, 80%, 85%, 90% 91%, 92%, 93%, 94%, 95%, 96%, 97%, 98% or 99% of the initial amount of the activity of protein present in the composition at 30 days following storage at 18° C. to about 25° C., 26° C., 27° C. or 28° C. The shelf life of the microparticle compositions provided herein generally is at least about 10 days at 55° C., at least about 2-3 weeks at 42° C., and at least about eight months or greater at 25° C., however, microparticles compositions of any length of shelf life at any temperature that are produced by the methods provided herein are contemplated herein.

As used herein, "a biologically active agent, "an active agent," "a biological agent," or "an agent," is any substance which when introduced into the body causes a desired biological response, such as altering body function at the cellular, tissue or organ level and/or altering cosmetic appearance, such as body weight and shape. Such substance can be any synthetic or natural element or compound, protein, cell, or tissue including a pharmaceutical, drug, therapeutic, nutritional supplement, herb, hormone, or the like, or any combinations thereof. The terms also encompass pharmaceutically acceptable, pharmacologically active derivatives of those active agents specifically mentioned herein, including, but not limited to, salts, esters, amides, prodrugs, active metabolites, isomers, fragments, analogs, and the like. When the terms "biologically active agent," "biological agent" and "agent" are used, then, or when a particular active agent is specifically identified, it is intended to include the active agent per se as well as pharmaceutically acceptable, pharmacologically active salts, esters, amides, prodrugs, active metabolites, isomers, fragments and analogs.

As used herein, a "subject" is defined as an animal, including a mammal, typically a human.

As used herein, "therapeutically effective amount" refers to an amount of the active agent for a desired therapeutic, prophylactic, or other biological effect or response when a composition is administered to a subject in a single dosage form. The particular amount of active agent in a dosage will vary widely according to conditions such as the nature of the active agent, the nature of the condition being treated, the age and size of the subject.

As used herein, "pharmaceutically acceptable derivatives" of a compound include salts, esters, enol ethers, enol esters, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

As used herein, "treatment" means any manner in which one or more of the symptoms of a condition, disorder or disease are ameliorated or otherwise beneficially altered. Treatment also encompasses any pharmaceutical use of the compositions herein, such as use for treating influenza.

As used herein, "organic solvent" refers to a solvent that is an organic compound, which is any member of a large class of chemical compounds whose molecules contain carbon and hydrogen. Such solvents can include, for example, compounds from the following classes: aliphatic or aromatic alcohols, polyols, aldehydes, alkanes, alkenes, alkynes, amides, amines, aromatics, azo compounds, carboxylic acids, esters, dioxanes, ethers, haloalkanes, imines, imides, ketones, nitriles, phenols and thiols.

As used herein, an "aqueous solvent" refers to water, or a mixture of solvents that contains at least about 50% or 50%, at least about 60% or 60%, at least about 70% or 70%, or about or at 75%, 80%, 85%, 90%, 95%, 96%, 97%, 98%, 99% or higher amounts of water. The term "aqueous solvent" as used herein also refers to solutions containing water as a solvent, such as buffers, salt solutions, solutions containing counterions, and other solutes that are soluble in water.

As used herein, the term "pI" or "isoelectric point" refers to the pH at which there is no net charge on a protein or polypeptide.

As used herein, the term "counterion" refers to a charged or charge-polarizable molecule that can initiate formation of a microparticle from a macromolecule, such as a protein, nucleic acid, lipid or oligosaccharide. For example, in the case of the DAS181 fusion protein (SEQ ID NO:17), sodium sulfate is a counterion because it can initiate the formation of microparticles in the methods provided herein, whereas glycine, sodium chloride or sodium acetate generally are not suitable as counterions for DAS181. Whether a charged molecule is a counterion can be determined empirically based on parameters including, but not limited to, the type of protein, the pH, the ionic strength, the type of organic solvent used, and the presence of salts and additional ingredients such as active agents. As provided and described herein, counterions can be anionic or having a net negative charge or charge-polarizable group(s), cationic or having a net positive charge or charge-polarizable group(s), or zwitterionic and possessing both negative and positive charged or charge-polarizable groups.

As used herein, the term "cooling" refers to a lowering of temperature to a desired temperature for obtaining microparticles or, once the microparticles are obtained, further lowering the temperature to a desired temperature for obtaining dry preparations of the microparticles by volatilizing solvents (e.g., for freeze-drying). The term "gradual cooling" or "gradually cooling" or "gradually cooled" as used herein means that the lowering of temperature to a desired temperature from ambient temperature (about or at 18° C. to about or at 30° C.) for microparticle formation occurs at a rate or for an amount of time that is suitable for generating microparticles in a solution before the solution becomes frozen. Thus gradual cooling is different from, for example, snap freezing, spray drying or spray freeze-drying, whereby the entire solution is converted to a solid form without the generation of distinct microparticles.

The rate of gradual cooling is empirically determined based on the type of macromolecule, solvents, counterions and other ingredients as well as the method of cooling (e.g., a heat exchanger, refrigerator or freezer or freeze-dryer) and can vary, for example, for an amount of time for microparticle formation of between about or at 1 min, 2 min, 3 min, 5 min, 7 min, 10 min, 15 min, 20 min, 25 min, 30 min, 1 h, 2 h, 5 h or 10 h to about or at 1.5 min, 2 min, 3 min, 5 min, 7 min, 10 min, 15 min, 20 min, 25 min, 30 min, 1 h, 2 h, 5 h, 10 h or 15 h.

As used herein, the term "cooling" refers to a lowering of temperature to a desired temperature for obtaining microparticles or, once the microparticles of desired dimensions are obtained, further lowering the temperature to a desired temperature for obtaining dry preparations of the microparticles by volatilizing solvents (e.g., for freeze-drying). The term "gradual cooling" or "gradually cooling" or "gradually cooled" as used herein means that the lowering of temperature to a desired temperature from ambient temperature at which the solution cocktail was formed (about or at −15° C. to about or at 50° C., generally about or at 18° C. to about or at 30° C.) for microparticle formation occurs at a rate or for an amount of time that is suitable for generating microparticles of desired dimensions in a solution before the solution becomes frozen. Thus gradual cooling is different from, for example, snap freezing, spray drying or spray freeze-drying, whereby the entire solution is converted to a solid form without the generation of distinct microparticles.

The rate of gradual cooling is empirically determined based on the type of macromolecule, solvents, counterions and other ingredients as well as the method of cooling (e.g., a heat exchanger, refrigerator or freezer or freeze-dryer) and can vary, for example, for an amount of time for microparticle formation of between about or at 0.1 sec, 0.2 sec, 0.5 sec, 1 sec, 10 sec, 20 sec, 30 sec, 40 sec, 50 sec, 1 min, 2 min, 3 min, 5 min, 7 min, 10 min, 15 min, 20 min, 25 min, 30 min, 1 h, 2 h, 5 h or 10 h to about or at 1.5 min, 2 min, 3 min, 5 min, 7 min, 10 min, 15 min, 20 min, 25 min, 30 min, 1 h, 2 h, 5 h, 10 h or 15 h.

Microparticles of desired size also can be formed, for example, by rapidly chilling the cocktail (e.g. using a heat exchanger) and allowing the suspension of microparticles to be maintained for a certain period of time without significant temperature changes, then snap freezing the cocktail.

The temperature at which microparticles are formed also is empirically determined based on the type of macromolecule, solvents, counterions and other ingredients as well as the method and uniformity of cooling and can vary from about or at 15° C., 10° C., 8° C., 5° C., 3° C., 2° C., 1° C., −2° C., −5° C., −7.5° C., −10° C., −15° C., −20° C., −25° C., −30° C., −35° C., −40° C. or −45° C.

As used herein, the term "spray drying" refers to a process wherein a solution containing a macromolecule, such as a protein, is transformed into a dry particulate form by atomizing into a hot drying medium, generally for a period of about a few milliseconds to 1-2 seconds to a few tens of seconds. The term "spray freeze-drying" as used herein refers to a process wherein a solution containing a macromolecule, such as a protein, is atomized into a cryogenic medium, such as liquid nitrogen, to obtain frozen droplets of solution that can then be dried by lyophilization. The term "snap freezing" or "rapid freezing" or "quick freezing" as used interchangeably herein refers to freezing a solvent or solution, including solutions containing macromolecules, such as proteins, by immersing the container with good heat transfer properties (e.g. thin-wall glass or metal test tube) holding the solvent or solution in liquid nitrogen or pouring the solution directly into liquid nitrogen. "Snap freezing" and "rapid freezing" generally occur within a period of about a few milliseconds to 1-2 seconds to a few tens of seconds.

The term "lyophilize" or "lyophilization" as used herein is synonymous with "freeze drying" and refers to a process wherein a solution, including an emulsion, colloid or suspension, is frozen and the solvents are volatilized directly into the vapor state, leaving behind the solid components.

B. Methods for Preparing Macromolecular Microparticle Compositions

Provided herein are methods of making microspheres having a high content of a macromolecule, such as a protein. The microspheres provided herein are prepared by controlled precipitation in the presence of a counterion and an organic solvent. The microspheres are suitable for preparing pharmaceutical compositions which can be delivered to a patient by delivery routes including pulmonary, parenteral and oral administration routes. The method also can be performed in a batch or continuous mode, for increased efficiency and production.

The microspheres obtained by the methods provided herein are useful as prophylactic, therapeutic or diagnostic agents for treating or diagnosing disease states in a subject in vivo or in vitro. The sizes of the microspheres obtained by the methods provided herein can be controlled by adjusting parameters including type and concentration of organic solvent, protein or macromolecule concentration, ionic strength, counterion type and concentration, rate and time of cooling, to provide microspheres in a wide range of sizes, from 0.001 micron to 50 microns or greater, that can deliver therapeutic agents via a desired route including pulmonary (e.g., 1 micron to 5 micron particles for delivery to the throat, trachea and bronchi for treatment of influenza and other respiratory infections), subcutaneous, intramuscular, intravenous and other routes (e.g., using particles of tens of microns in size). render active components of inhalant medicines for human subjects.

The steps of the method provided herein include: combining the a solution containing the macromolecule with a counterion and an organic solvent, and gradually cooling the resulting solution to a temperature whereby microparticles are formed. In one embodiment, the steps can be described as follows:

1) To a solution containing a macromolecule, such as a protein, nucleic acid, oligosaccharide or lipid, adding a counterion and an organic solvent at concentrations that do not cause precipitation of the macromolecule at ambient temperature;

2) Precipitation: cooling the macromolecule/solvent cocktail to initiate formation of microspheres; and 3) Dehydration: freezing of the suspension and removal of organic solvent and water by sublimation (freeze-drying, e.g., at a temperature of about −20° C. to about −80° C., or about −30° C. to about −80° C., or about −40° C. to about −80° C., or about −45° C. to about −80° C., or about −45° C. to about −75° C.).

The above steps of the method can be performed sequentially, intermittently or simultaneously in any order. In one embodiment, the counterion and the organic solvent are added simultaneously or sequentially in any order to the solution containing the macromolecule, followed by chilling. In other embodiments, the solution containing the macromolecule can be pre-chilled to a temperature suitable for microsphere formation, prior to adding the counterion and organic solvent. For example, a prechilled aqueous solution of a macromolecule, such as a protein, can be combined with ammonium sulfate and acetonitrile to form microspheres.

The resulting suspension of microparticles can be converted into a dry powder by further cooling to a temperature below freezing point and subsequent removal of volatiles (water, organic solvent and where possible the counterion) by, for example, sublimation using a standard freeze dryer.

In one embodiment, the microspheres formed by contacting the macromolecule with a counterion and organic solvent and exposed to low temperature, are separated from the suspension by methods including sedimentation or filtration techniques. After separation from the original precipitation mix, the microspheres can be washed and/or combined with other materials that improve and/or modify characteristics of macromolecules and microspheres.

In another embodiment, the microspheres prepared by the methods provided herein do not have a direct therapeutic effect, but serve as micro-carriers for other therapeutic agent(s) or active agent(s) including nutritional supplements. Therapeutic agents can be added at the time of precipitation or can be added to the suspension of formed microspheres prior to lyophilization. Alternatively, therapeutic agents can be blended into dry powder consisting of microspheres.

Without being bound by any theory, in one aspect, the methods provided herein can permit the formation of microspheres by: (1) neutralization of charges on the surface of macromolecule by the counterion and (2) decreased solubility of the macromolecule caused by the combined effects of added organic solvent and gradual cooling.

By choosing a suitable pH in the range of about or at pH 2.0 to about or at 10.5 or greater, depending on the macromolecule, counterion, and organic solvent, in the presence of a suitable amount of the counterion, a substantial number of the charged groups, in some embodiment all charged groups, on the surface of the macromolecule can become neutralized. A decrease in the polarity of the solution by adding a suitable organic solvent can then initiate the formation of microspheres by precipitation, phase separation, colloid formation, or other such method.

Alternatively, without being bound by any theory, in some embodiments, the observed phenomenon of the precipitation of microspheres also can be explained by the kosmotropic (structure forming) effect of counterions and organic solvents due to interactions with the water molecules of the aqueous solution containing the macromolecule at low temperatures. Regardless of the underlying mechanism, in the methods provided herein, the addition of relatively small amounts of organic solvent and counterion to an aqueous or other hydrophilic solution containing a macromolecule and cooling of the solution results in the production of compositions containing microspheres of the macromolecule(s).

In one embodiment, gradual cooling chilling of the cocktail solution can be performed by passing the cocktail solution through a heat exchanger. The temperature of the heat exchanger and the flow rate of the cocktail through the heat exchanger can be adjusted so that the cocktail is either prechilled prior to formation of the microspheres, or is chilled to a temperature whereby microspheres are formed.

In another embodiment, the microspheres formed by the methods provided herein are concentrated or separated from the suspension by methods such as sedimentation or filtration techniques. Upon formation of the microspheres, their growth (size) can be controlled by adjusting the ionic strength, polarity, pH, or other parameters of the suspension. The separation of microspheres from the liquid phase of the cocktail solution can be performed by centrifugation, filtration (hollow fiber, tangential flow, etc.), or other techniques. The resulting microspheres or concentrated suspensions thereof can be lyophilized or air dried.

In some embodiments, the microspheres separated from the original precipitation mix or the dried microspheres can be reconstituted prior to administration as a therapeutic agent or a carrier, or can be suspended in solutions that contain agents that modify characteristics of the microspheres. The modifying agents can include but are not limited to bulking agents, excipients, inactive ingredients, stability enhancers, taste and/or odor modifiers or masking agents, vitamins, therapeutic agents, anti-oxidants, immuno-modulators, trans-membrane transport modifiers, anti-caking agents, enteric coating agents, agents that confer acid resistance, such as against the acids of the digestive system, agents that confer protease resistance, chitosans, polymers, and flowability enhancers.

The formation and characteristics of the microspheres produced by the methods provided herein can empirically be determined by varying parameters, including: nature and concentration of the macromolecule, pH of the cocktail solution, nature and concentration of the counterion, nature and concentration of the organic solvent, ionic strength and the cooling rate by which gradual cooling is effected. The steps of the methods provided herein render the method amenable to high-throughput screening, such as in a microplate format, for determining suitable combinations of macromolecule, organic solvent, counterion, pH, ionic strength and cooling ramp for the generation of microspheres.

Macromolecules

Macromolecules that can be used to form microspheres according to the methods provided herein include a variety of therapeutic agents, diagnostic agents, nutritional agents and other active agents. Therapeutic agents include antibiotics, vaccines, hematopoietics, anti-infective agents, antiulcer agents, antiallergic agents, antipyretics, analgesics, anti-inflammatory agents, antidementia agents, antiviral agents, antitumoral agents, antidepressants, psychotropic agents, cardiotonics, antiarrythmic agents, vasodilators, antihypertensive agents, antidiabetic agents, anticoagulants, and cholesterol lowering agents. Other examples of suitable macromolecules include proteins, peptides, nucleic acids, carbohydrates, protein conjugates, viruses, virus particles, and mixtures thereof.

The macromolecules can be characterized by their ability to interact with the counterion and organic solvent, such as citrate (counterion) and isopropanol (solvent), to form intact, discrete microspheres containing a high content of macromolecule. The content of the macromolecule in the microspheres can vary from about or at 30%, 40%, 45%, 50%, 55%, 60%, 65%, 70%, 75%, 80%, 85%, 90%, 91%, 92%, 93%, 94%, 95%, 96%, 97%, 98%, 99% or greater weight/weight (w/w) of the microspheres. In some embodiments, the macromolecule content of microsphere is substantially the same as the amount of macromolecule initially in solution, prior to forming the microspheres.

The macromolecules used to prepare microspheres by the methods provided herein can include peptides, including polypeptides and proteins, carbohydrates, including polysaccharides and nucleic acids (DNA, RNA or PNA). In some embodiments, the macromolecules are proteins, including therapeutic proteins such as DAS181 (the sialidase fusion protein having the sequence of amino acid residues set forth in SEQ ID NO:17), alpha1-antitrypsin, PI8, eglin c, Ecotin, aprotinin, recombinant human DNase, insulin, interferons, recombinant human DNAse (rhDNAse, useful, for example, in the treatment of cystic fibrosis as an inhalation therapeutic (Genentech); see also Shak et al., Proc. Natl. Acad. Sci. USA, 87:9188-9192 (1990)), human serum albumin, human growth hormone, parathyroid hormone and calcitonin. In some embodiments, the protein is DAS181, the counterion is sodium sulfate or sodium citrate, and the organic solvent is isopropanol.

The methods provided herein can avoid the use of conditions, such as heat, that can denature the protein and reduce its activity. The microspheres provided according to the methods provided herein therefore can be used to prepare vaccines or other therapeutic medications that require proteins or peptides to be present in their native conformation.

The concentration of the macromolecule in solution, used during precipitation of the microspheres, can be between about or at 0.1 mg/ml to about or at 0.2, 05, 0.8, 1.0, 2.0, 5.0, 10.0, 12.0, 15.0, 20.0, 25.0, 30.0, 35.0, 40.0, 45.0, 50.0, 60.0, 70.0, 80.0, 90.0, 100, or 200 mg/ml. In some embodiments, the concentration is between about or at 1 mg/ml and about or at 20 mg/ml. Depending on the characteristics of the macromolecule (pI, hydrophobicity, solubility, stability, etc.) and other process parameters, the concentration of macromolecule can empirically be determined to achieve formation of microspheres of a desired size. In general, macromolecules with lower solubility in the solvent (generally, aqueous solvent) prior to adding counterion and organic solvent can be used at lower concentrations (0.1-5 mg/ml) to form microspheres according to the methods herein, while macromolecules with higher solubility can be used at 1-20 mg/ml or higher. If the formation of amorphous aggregates or aggregated microspheres is observed, the concentration of the macromolecule generally should be decreased to reduce or prevent such aggregation.

Nature and Concentration of Counterion

The counterion can be any compound capable of neutralizing one or more oppositely charged groups on the macromolecule at the pH at which the method is performed. Depending on the characteristics of the macromolecule (pK, pI, nature and quantity of charged groups, distribution of charge groups on the surface, solubility and structural stability under different pH conditions), the pH can empirically be determined for microsphere formation. In general, if precipitation is performed at a pH below the pK of the macromolecule, anionic counterions can be used. In general, if precipitation is performed at a pH above the pK of the macromolecule, cationic counterions can be used. The counterion can empirically be selected based on its suitability to initiate microsphere formation. In some embodiments, the counterion can have a molecular weight of 60 Da or greater, or about 75 Da or greater.

The counterions can be anionic, cationic or zwitterionic. Anionic counterions can be inorganic (phosphate, sulphate, thiocyanate, thiosulfate, hypochlorate, nitrate, bromine, iodine, etc.) or organic compounds that carry charge-polarizable groups including enol, hydroxy, —SH, carboxylic, carboxymethyl, sulfopropyl, sulfonic, and phosphoric. Organic compounds carrying other anionic groups or having negative charge due to other molecular characteristics also can be used. Compounds that can be used as anionic counterions also include, but are not limited to, the following: oxaloacetate, malate, maleate, oxalate, piruvate, citrate, succinate, fumarate, ketoglutarate, butanetricarboxylic acid, hydromuconic acid, cyclobutanedicarboxylic acid, dimethyl maleate, deoxyribonucleic acid, polyglutamic acid, folic acid, lactic acid, ascorbic acid, carminic acid, sorbic acid, malonic acid, EDTA, MOPS, TES, MES, PIPES, pyridine, tricine, glycine, glycylglycine, betaine, sulfuric acid, thiosulfuric acid, phosphoric acid, adenosine triphosphate, nitric acid, itaconic acid, pivalic acid, dimethylmalonic acid, and perchloric acid. In some embodiments, itaconic, pivalic, dimethylmalonic, and succinic acids are used as counterions in the methods provided herein.

Cationic counterions can be inorganic (ammonium, phosphonium, sulfonium, cesium, rubidium, etc.) or organic compounds that carry groups known as amine, amide, imine, imide, guanidine, imidazole, dioxane, aniline. Organic compounds carrying other cationic groups or have positive charge polarizability due to other molecular characteristics also can be used. Compounds that can be used as cationic counterions also include, but are not limited to, the following: Tris, Bis-Tris, Bis-Tris propane, diaminopropane, piperazine, piperadine, pentylamine, diaminobutane, propylamine, trimethylamine, triethylamine, spermine, spermidine, putrescine, cadaverine, ethanolamine, diethanolamine, triethanolamine, imidazole, tetramethylammonium, trimethylammonium, ammonium, cesium, rubidium, imidazole, polyethyleneimine, DEAE, TEAE, QAE.

Zwitterionic counterions possessing any charged groups in any combination can also be used. Compounds that can be used as zwitterionic counterions include, but are not limited to, the following: HEPES, BICINE, glycine, glycylglycine, 6-aminohexanoic acid, piperidic acid, natural and non-natural amino acids (e.g., histidine, glutamine, arginine, lysine).

The counterions can be used as acids (e.g. sulfuric acid) or bases (e.g. imidazole) or their salts (e.g. sodium sulfate or imidazole-HCl). Counterions that can be used in the methods provided herein include those listed by the National Formulary, United States Pharmacopeia, Japanese Pharmacopeia, or European Pharmacopeia, the clinical safety of which has been demonstrated (citric acid, malic acid, amino acids, sulfate, etc.). In some embodiments, counterions used in the methods provided herein include ones for which safety has been established or as falling into the GRAS (generally regarded as safe) category. The counterions (or their salts) can be solid at room temperature (about 25° C.), or at the intended temperature of use and storage). Combinations of two or more counterions also can be used. Volatile and liquid counterions also can be used in the methods provided herein.

The concentration of counterion generally is maintained between about 0.1 mM and about 0.2, 0.5, 0.8, 1.0, 2.0, 3.0, 5.0, 7.0, 10.0, 15.0, 20.0, 30.0, 40.0, 50.0, 60.0, 70.0, 80.0, 90.0 and 100.0 mM. In some embodiments, the concentration of the counterion is between about or at 0.5 mM and about or at 20 mM. Depending on the characteristics of macromolecule (pI, hydrophobicity, solubility, stability, etc.) and other process parameters, the concentration of the counterion can empirically be determined using, for example, a high-throughput format as provided herein. In general, the formation of oversized microspheres, amorphous aggregates or aggregated microspheres indicates that the concentration of counterion should be decreased, while failure to form microspheres (broken glass-like crystals or flakes) or formation of microspheres below the desired size indicates that the concentration of counterion should be increased.

Nature and Concentration of Organic Solvent

An organic solvent added to the cocktail in the methods provided herein generally can be water miscible and selected from among alcohols (methanol, ethanol, 1-propanol, isopropanol, butanol, tert-butyl alcohol), chloroform, dimethyl chloride, polyhydric sugar alcohols (glycerin, erythriol, arabitol, xylitol, sorbitol, mannitol), aromatic hydrocarbons, aldehydes, ketones, esters, ethers (di-ethyl ether), alkanes (hexane, cyclohexane, petroleum ether), alkenes, conjugated dienes, toluene, dichloromethane, acetonitrile, ethyl acetate, polyols, polyimids, polyesters, polyaldehydes, and mixtures thereof. In some embodiments, the organic solvent can be volatile. In other embodiments, when incorporation of the organic solvent into the microspheres is desired, non-volatile organic solvents can be used that provide, for example, novel characteristics to the microspheres (e.g., sustained release or added mechanical strength). The concentration of the organic solvent generally can be maintained between about or at 0.1%, to about or at 0.5%, 1%, 2%, 5%, 10%, 15%, 20%, 25%, 30%, 40% or 50%, volume/volume (v/v). In some embodiments, the concentration of the organic solvent is between about or at 1% to about or at 30%, v/v. Organic compounds that are partially miscible or completely immiscible with water also can be used.

Organic solvents that can be used in the methods provided herein include alcohols and others listed as Class 3 and 2 solvents in International Conference on Harmonisation (ICH) Harmonised Tripartite Guideline (Impurities: Guideline for Residual Solvents), safe handling of which has been established in pharmaceutical and food industries.

Depending on the characteristics of the macromolecule (hydrophobicity, solubility, stability, etc.) and other process parameters, the choice and concentration of the organic solvent can be optimized, for example, using high-throughput screening on microtiter plates or similar chips or other device. In general, uncontrolled precipitation before the initiation of cooling, the formation of oversized microspheres, amorphous aggregates, aggregated microspheres or sticky aggregates indicates that the concentration of organic solvent should be decreased, while failure to form microspheres (broken glass-like crystals or flakes) or formation of microspheres below the desired size indicates that the concentration of the organic solvent should be increased.

pH

In addition to initiating microsphere formation, the counterion also can serve as a buffer. Alternately, in some embodiments, a buffering compound can be used to obtain the desired pH. In some embodiments, the buffering compound is 60 Da or larger. Depending on the characteristics of the macromolecule (pI, hydrophobicity, solubility and stability at a specific pH, etc.) and other process parameters, the optimal pH can empirically be adjusted to achieve formation of microspheres of desired dimensions and preserve the activity of the macromolecule. In general, failure to form microspheres (broken glass-like crystals or flakes) indicates that the protein may be too soluble under the conditions used. Formation of amorphous aggregates can indicate that precipitation is not well controlled and the protein may not be stable or soluble at the pH used.

When the macromolecule is a protein, it has been observed that certain protein/counterion combinations can cause immediate and uncontrolled precipitation at certain pH values. The high-throughput screening methods provided herein can be used to empirically determine the appropriate combination of protein, pH and counterion to form microspheres of desired dimensions. his is easily remedied by changing the pH of the cocktail, by using a different counterion or by decreasing concentration of the protein in cocktail. In general, for forming protein-based microspheres, a pH value that is below the pI of the protein provides optimal microsphere formation Ionic Strength The ionic strength of the cocktail solution can be modulated by the concentration of the counterion or by other salts such as chlorides or acetates. In some embodiments, no additional salt is required to produce microspheres. In certain embodiments, the ionic strength can be adjusted to preserve the structural integrity and activity of the macromolecule. Examples of other applications where the presence of specific salts can be beneficial include formulations of parenteral and other drugs, or foods where specific tonicity or buffering capacity may be required upon reconstitution of microspheres.

Cooling Ramp

The cocktail containing a macromolecule, a counterion and an organic solvent initially is prepared, prior to cooling, at a temperature at which the macromolecule is soluble, generally about −15° C. to about 30° C. In some embodiments, the initial temperature, prior to cooling is at ambient temperature (18-25° C.). The microspheres are formed by a process such as precipitation, phase separation or colloid formation upon gradual cooling to a temperature below the temperature at which the macromolecule is dissolved and in solution. The rate at which cooling is performed can control the formation and other characteristics such as size of the microspheres. In general, when the macromolecule is protein, flash-freezing in liquid nitrogen does not generate microspheres The rate at which cooling and freezing of the cocktail (cooling ramp) is performed can determine the final size of the microspheres. In general, a faster cooling ramp yields smaller microspheres whereas a slower cooling ramp yields larger microspheres. Without being bound by any theory, the cooling rate can determine the rate of: (1) nucleation that produces initial smaller microspheres and (2) a fusion process in which the initial microspheres coalesce (aggregate) and anneal into larger microspheres. Fusion of the smaller particles into larger ones is a time dependent process that can be determined, for example, by the duration for which liquid suspension of microspheres exists prior to freezing. Due to the reversible nature of the bonds between certain macromolecules, such as some proteins, in the microsphere compositions provided herein, smaller microspheres annealing into larger particles can generate microspheres with smooth surfaces. Depending on the size of microparticles desired, the cooling rate can be from about 0.01° C./min or 0.01° C./min to about 20° C./min or 20° C./min; from about or at 0.05° C./min or about or at 0.1° C./min to about or at 10° C./min or about or at 15° C./min, from about or at 0.2° C./min to about or at 5° C./min, from about or at 0.5° C./min to about or at 2° C./min, or about or at 1° C./min. In some embodiments, the cooling ramp can be between 0.1° C. per minute and about 40° C. per minute. In other embodiments, a cooling ramp can be between about 0.5° C. per minute and 15° C. per minute.

Depending on the specific needs, in some embodiments it can be desirable to adapt the production process to the specific equipment. In some embodiments, a lyophilizer with temperature-controlled shelves can be used for the cooling. if the microspheres produced are larger than desired, other parameters of the process including concentration of macromolecule, organic solvent, counterion, ionic strength and/or pH can be modified to achieve the desired reduction in size of the microspheres.

For a faster cooling ramp (smaller particle size), the cocktail solution can be passed through a heat exchanger, such as that used in a continuous mode. If the size of microspheres needs to be increased, increased concentrations of one of the cocktail ingredients (macromolecule, organic solvent, counterion) can provide the desired increase in the size of microspheres.

In general, the cooling should be performed uniformly and at a steady rate to prevent the formation of aggregates and crystal. Depending on the concentration of the organic solvent, the precipitation of the macromolecule into microspheres can occur in several ways. At higher concentrations of organic solvent (about 5%-40%, dependent on the actual components used) the microspheres generally can form when the cocktail solution is still in liquid form. At lower concentrations of organic solvent (2-25%, dependent on the actual components used) ice crystals can form first, following which the expelled macromolecules and organic solvent reach can reach a critical local concentration and precipitate. A further decrease of temperature in the near-bottom layer of the lyophilizer tray can leas to complete solidification of the liquid suspension and further expulsion of the organic solvent into the top layer. An excess of organic solvent in the top layer can cause uncontrolled precipitation of the macromolecule and aggregation of microspheres. This effect usually can be alleviated by selecting appropriate ratios of the components—macromolecule, counterion, organic solvent, salts, etc. in the cocktail. In addition, maintaining a thin layer of cocktail in the lyophilization tray or mixing of the cocktail while chilled can prevent formation of aggregates and crystals and yield uniform microspheres. For example if a relatively low concentration of Isopropanol (e.g. 2-6%) is used, and a thin layer of cocktail (10-20 mm) is filled into the tray, and the tray is placed on a pre-chilled shelf (−30-75° C.) uniform microspheres can be obtained.

The methods provided herein can lead to substantially all or all the protein or other macromolecule being incorporated from the solution into the microspheres High-Throughout Screening of Microparticle Formation Conditions and Optimization of Particle Formation Depending on the characteristics of the macromolecule, the composition of the cocktail solution used to prepare the microspheres according to the methods provided herein can be optimized. The optimization can rapidly be performed in a medium or high throughput format using, for example microtiter plate(s) or chips where tens to hundreds to thousands to tens of thousands of cocktails can be screened simultaneously. In some embodiments, a number of pH values in conjunction with cationic, anionic or zwitterionic counterions and organic solvents at various concentrations can be screened. For example, the screening can be performed using several identical microtiter plates, to each of which the macromolecule of interest is added at various concentrations. Each set of test conditions can be screened in duplicate. In some embodiments, microplates with flat-bottom well can be used with the skirt of the microtiter plate broken off to permit good heat transfer between the lyophilizer shelf and the bottoms of the wells. The microplates can be placed on the shelves of the lyophilizer and cooled to form microspheres and to subsequently solidify the suspensions. Upon freezing of the contents of the wells, a vacuum can applied. At the end of lyophilization, one of the duplicate plates can be reconstituted with water or a buffer of choice to observe if certain conditions rendered the macromolecule insoluble or reduced its activity. Conditions that resulted in material that can readily be resolubilized or provide microspheres with desirable characteristics can be subjected to further analysis by spectroscopic, chromatographic, enzymatic or other assays to confirm that native structure and activity are preserved. Lyophilized material in a duplicate plate can be used for microscopy to determine whether microspheres are formed. Conditions that produced microspheres can further be modified and fine-tuned to produce microspheres of desirable size and characteristics.

Kits for performing high-throughput screens can be provided and can contain all the ingredients used in the methods provided herein including one or more of a macromolecule, such as a protein, buffers, pre-dispensed cocktail of known composition (organic solvent, counterion) and/or salts. Kits can contain 3, 4, 5, 10, 15, 20, 30, 40, 50, 100 or more (typically 96 or more) buffers with predetermined pH, counterion, ionic strength and organic solvent in each microtiter plate. The microtiter plate supplied with the kit can be modified so that bottoms of wells are in direct contact with the shelf of lyophilizer.

C. Macromolecular Microparticle Compositions

The macromolecules contained in the microparticle compositions obtained by the methods provided herein are substantially structurally and chemically unchanged by the methods. For example, when the macromolecule is Green Fluorescent Protein or Red Fluorescent Protein, their fluorescence and native conformation and activity of the proteins are retained in the microparticles. The dry microspheres, obtained by volatilizing substantially all of the solvents and/or moisture except for the solvent and other components associated with the microspheres, can be stored and their activity can substantially be recovered upon reconstitution.

The relatively low moisture content of the microparticles provided herein, for example, between about or at 0.1% to about or at 0.2%, 0.3%, 0.5%, 1.0%, 2.0%, 3.0%, 4.0%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 14%, 15%, 16%, 17%, 18% 19%, or 20%, can provide improved stability. The microspheres obtained by the methods provided herein also are homogeneous in size and shape, and can be obtained reproducibly with the desired characteristics. Other techniques traditionally used for preparation of dry formulations (salt precipitation, alcohol or acetone precipitation, lyophilization, e.g.) can result in complete or partial denaturation of the macromolecules, such as proteins. In addition, the microspheres prepared by the methods provided herein avoid the need for complex or specialized spray drying, spray freeze-drying, supercritical fluid anti-solvent based processes or milling processes (See, for example, Laube B L. The expanding role of aerosols in systemic drug delivery, gene therapy, and vaccination. Respir Care 2005; 50(9):1161-1176; Taylor G, Gumbleton M. Aerosols for Macromolecule Delivery: Design Challenges and Solutions. American Journal of Drug Delivery 2004; 2(3):143-155; Smyth H D C, Hickey A J. Carriers in Drug Powder Delivery. Implications for Inhalation System Design. American Journal of Drug Delivery 2005; 3(2):117-132; Cryan S A. Carrier-based strategies for targeting protein and peptide drugs to the lungs. AAPS J 2005; 7(1):E20-E41; LiCalsi C, Maniaci M J, Christensen T, Phillips E, Ward G H, Witham C. A powder formulation of measles vaccine for aerosol delivery. Vaccine 2001; 19(17-19):2629-2636; Maa Y F, Prestrelski S J. Biopharmaceutical powders: particle formation and formulation considerations. Curr Pharm Biotechnol 2000; 1(3):283-302; Maa Y F, Nguyen P A, Hsu S W. Spray-drying of air-liquid interface sensitive recombinant human growth hormone. J Pharm Sci 1998; 87(2):152-159; Vanbever R, Mintzes J D, Wang J et al. Formulation and physical characterization of large porous particles for inhalation. Pharm Res 1999; 16(11):1735-1742; Bot A I, Tarara T E, Smith D J, Bot S R, Woods C M, Weers J G. Novel lipid-based hollow-porous microparticles as a platform for immunoglobulin delivery to the respiratory tract. Pharm Res 2000; 17(3):275-283; Maa Y F, Nguyen P A, Sweeney T, Shire S J, Hsu C C. Protein inhalation powders: spray drying vs spray freeze drying. Pharm Res 1999; 16(2): 249-254; Sellers S P, Clark G S, Sievers R E, Carpenter J F. Dry powders of stable protein formulations from aqueous solutions prepared using supercritical $CO_2$-assisted aerosolization. J Pharm Sci 2001; 90(6):785-797; Garcia-Contreras L, Morcol T, Bell S J, Hickey A J. Evaluation of novel particles as pulmonary delivery systems for insulin in rats. AAPS PharmSci 2003; 5(2):E9; Pfutzner A, Flacke F, Pohl R et al. Pilot study with technosphere/PTH(1-34)—a new approach for effective pulmonary delivery of parathyroid hormone (1-34). Horm Metab Res 2003; 35(5):319-323; Alcock R, Blair J A, O'Mahony D J, Raoof A, Quirk A V. Modifying the release of leuprolide from spray dried OED microparticles. J Control Release 2002; 82(2-3):429-440; Grenha A, Seijo B, Remunan-Lopez C. Microencapsulated chitosan nanoparticles for lung protein delivery. Eur J Pharm Sci 2005; 25(4-5):427-437; Edwards D A, Hanes J, Caponetti G et al. Large porous particles for pulmonary drug delivery. Science 1997; 276(5320):1868-1871; McKenna B J, Birkedal H, Bartl M H, Deming T J, Stucky G D. Micrometer-sized spherical assemblies of polypeptides and small molecules by acid-base chemistry. Angew Chem Int Ed Engl 2004; 43(42): 5652-5655; Oh M, Mirkin C A. Chemically tailorable colloidal particles from infinite coordination polymers. Nature 2005; 438(7068):651-654; U.S. Pat. No. 5,981,719; U.S. Pat. No. 5,849,884 and U.S. Pat. No. 6,090,925; U.S. Patent application No. 20050234114; U.S. Pat. No. 6,051,256).

The microparticles obtained by the methods provided herein can be of any shape and can have sizes (mean width or diameters) in the range of from about or at 0.001 micron to about or at 0.002, 0.005, 0.01, 0.02, 0.03, 0.05, 0.1, 0.02, 0.03, 0.5, 1.0, 2.0, 2.5, 3.0, 3.5, 4.0, 4.5, 5.0, 5.5, 6.0, 6.5, 7.0, 7.5, 8.0, 8.5, 9.0, 9.5, 10.0, 15.0, 20.0, 25.0, 30.0, 35.0, 40.0, 45.0, or 50.0 or greater microns. For pulmonary administration to the alveoli, the size can be from about 0.1 micron or less to about 0.5 micron. For pulmonary administration to the throat, trachea and bronchi, the size can be from about or at 0.5 microns to about or at 1.0, 1.5, 2.0, 2.5, 3.0, 3.5, 4.0, 4.5, 5.0, 5.5, 6.0, or 6.5 microns, or in some embodiments from about or at 1.0 micron to about or at 2.0 microns. In some embodiments, the microparticles are substantially spherical in shape.

The macromolecules that can be used to form microparticles according to the methods provided herein can include therapeutic and diagnostic agents, processed foods, dietary supplements and polymers. In some embodiments, cross-linking agents, salts, or other compounds can be included in the formulation cocktail to modify solubility of the microspheres and/or enhance their mechanical strength. In some embodiments, microspheres that are insoluble in most aqueous or organic solvents can be used to manufacture particles such as chromatographic resins and dispersible abrasives. In other embodiments, microspheres with partial solubility in solvents such as pharmaceutical vehicles for delivery can be useful in the manufacture of sustained release active agent or therapeutic formulations.

In some embodiments, the microparticles provided herein can be used in combination with an inhaler device to deliver a therapeutic dose of macromolecular microspheres to the respiratory airways and lungs of a subject. For example, when the macromolecule is the DAS181 protein (sequence set forth in SEQ ID NO: 17), microspheres of about 0.5 micron to about 8 microns, or about 1 micron to about 5 micron can be obtained by the methods provided herein, using sodium sulfate as the counterion and isopropanol as the organic solvent. For DAS181 microspheres, which are administered to prevent or treat viral infections that initiate in the respiratory tract, such as influenza, it can be desirable to deposit the microspheres in the throat, trachea or bronchi. The DAS181 fusion protein formulated as microspheres can act by degrading the receptor sialic acids in the throat/trachea/bronchi, thus preventing viral binding and infection at these sites. For optimal delivery of the DAS181 microspheres to sites where respiratory viral infection can be initiated, i.e., in the throat, trachea or bronchi, the microspheres must not be (a) so big that they are trapped at the front end in the mouth (i.e., microspheres are too big, about 8 microns or greater); or (b) so small that they are absorbed deep in the lungs and absorbed systemically into the blood stream through the alveoli where they are not active and/or can be toxic (i.e., 0.5 micron or smaller). For delivery of the DAS181 microspheres to the throat, trachea and bronchi, a size range of about 1 micron to about 5.5-6 microns generally can be suitable.

The inhaler can be used to treat any medical condition in which the protein or other macromolecule can be administered by inhalation therapy. Typical inhaler devices can include dry powder inhalers, metered dose inhalers, and electrostatic delivery devices. Typical applications of the delivery apparatus of include the deep lung delivery of insulin and other therapeutic proteins.

In some embodiments, the microspheres obtained by the methods provided herein also can be delivered by oral ingestion, intranasally, intravenously, intramuscularly, subcutaneously, and by other delivery methods suitable for the delivery of therapeutic molecules. The microsphere formulations for pulmonary delivery generally can be in a size range of about 0.5 micron to about 5-6 microns, while those designed for other types of delivery, such as subcutaneous delivery, parenteral delivery or intramuscular delivery can be in a range of from about or at 10 micron to about or at 30, 40 or 50 microns.

In some embodiments, the microspheres provided herein have no direct therapeutic effect but can serve as microcarriers for other therapeutic agent(s). Examples of macromolecules useful for preparation of such microspheres include but are not limited to polysaccharides, glycans, proteins, peptides, polymers or combinations thereof. Therapeutic agents or other active agents can be added at the time of microsphere formation or added to the suspension of formed microspheres. Alternatively, therapeutic agents can be blended with the dry microsphere compositions by mixing, tumbling or other techniques practiced in pharmaceutical and food industries.

In some embodiments, cross-linking agents, lipophilic substances, salts such as those with poor solubility in aqueous solvents, or combinations thereof or other compounds can be included in the formulation cocktail solution to modify the solubility of the microspheres and/or enhance their mechanical strength. Slow dissolution of the microspheres can be useful in sustained release of therapeutics delivered by oral ingestion, inhalation, intranasally, intravenously, intramuscularly, subcutaneously, and by other delivery methods suitable for the delivery of therapeutic molecules. In some embodiments, the microspheres can be delivered by oral ingestion in a form of a pill or capsule with an enteric coating, endocytosed from the duodenum, and the macromolecule released into the blood stream or other site of action.

In some embodiments, the microspheres can be rendered insoluble by partial denaturation of the macromolecule, which upon delivery becomes renatured and bioavailable.

In other embodiments, the microspheres are substantially spherical in shape, and can have mean diameters within the range of from about 0.1 microns to 30.0 microns. In yet other embodiments, the mean diameter of the microspheres can be within the range of from about 0.5 microns to 5.0 microns, or from about 1.0 microns to 2.0 microns.

In yet another aspect, provided herein are devices and methods for delivering the microspheres to a subject, such as an animal or human patient in need of medical treatment. Suitable delivery routes can include parenteral, such as i.m., i.v. and s.c., and non-parenteral, such as oral, buccal, intrathecal, nasal, pulmonary, transdermal, transmucosal, and the like delivery routes. Delivery devices can include syringes, both needleless and needle containing, and inhalers.

The delivery devices can contain a single dose of the microspheres for treating a condition that is treatable by rapid or sustained release of the macromolecule in vivo. The number of microspheres present in the single dose is dependent on the type and activity of the macromolecule. The single dose can be selected to achieve sustained release over a period of time that has been optimized for treating the particular medical condition. For example, when the macromolecule is the DAS181 fusion protein (SEQ ID NO:17), the delivery dosage of microsphere compositions containing DAS181 can be from between about 0.5 mg protein per dose to about 100 mg protein per dose, or about 0.75 mg, 1 mg, 1.5 mg, 2 mg, 3 mg, 5 mg, 10 mg, 15 mg, 20 mg, 30 mg, 40 mg, 45 mg, 50 mg, 55 mg or 60 mg protein per dose.

The macromolecule component of the microsphere can be any molecule capable of forming microspheres according to the methods provided herein. In some embodiments the macromolecule is a protein, including enzymes and recombinant proteins, peptides, carbohydrates, polysaccharides, carbohydrate- or polysaccharide-protein conjugates, nucleic acids, virus, virus particles, conjugates of small molecules (such as a hapten) and proteins, or mixtures thereof. An organic or inorganic natural or synthetic pharmaceutical compound or drug can be incorporated into the microspheres by attaching the drug to a macromolecule, such as a protein, and then forming the microspheres from the macromolecule-drug complex or conjugate. It will be understood by those skilled in the art that a compound incapable of having a tertiary and quaternary structure can be formed into a microsphere by incorporation or coupling of the compound into a carrier molecule that has a tertiary and quaternary structure. It will further be understood by those of skill in the art that the macromolecule can be a portion of a molecule such as, for example, a peptide, a single-stranded segment of a double-stranded nucleic acid molecule, or a virus particle, or other macromolecule having a tertiary and quaternary structure.

The term “macromolecule” also can include a plurality of macromolecules and includes combinations of different macromolecules such as a combination of a pharmaceutical compound and an affinity molecule for targeting the pharmaceutical compound to a tissue, organ or tumor requiring treatment. An affinity molecule can be, foe example, a ligand or a receptor. Examples of ligands can include viruses, bacteria, polysaccharides, or toxins that can act as antigens to generate an immune response when administered to an animal and cause the production of antibodies.

In some embodiments, the macromolecule is a therapeutic protein including, but not limited to, a sialidase, a sialidase fusion protein, a fusion protein containing a sialidase catalytic domain fused to a GAG-binding domain, a protease, a protease inhibitor, insulin, interferons, human growth hormone, calcitonin, rhDNase or parathyroid hormone, and the protein content of the microspheres can be from about or at 50% to about or at 60%, 65%, 70%, 75%, 80%, 85%, 90%, 95%, 96%, 97%, 98%, 99% or greater. For pulmonary administration, the microspheres can have an average size in the range of from about or at 0.5 microns to about or at 5.0 microns, and in some embodiments, between about or at 1 micron and about or at 2 microns.

Other proteins that can be used to form microspheres by the methods provided herein can include, but are not limited to, therapeutic proteins including DAS181 (DAS181; SEQ ID NO:17), a1-antitrypsin, Ecotin, eglin c, serpin, Pulmozyme (rhDNase), Betaxolol™, Diclofenac™, doxorubicin, acetyl cysteine, Rifampin™, leuprolide acetate, luteinizing hormone releasing hormone (LHRH), (D-Tryp6)-LHRH, nafarelin acetate, insulin, sodium insulin, zinc insulin, protamine, lysozyme, alpha-lactalbumin, basic fibroblast growth factor (bFGF), beta-lactoglobulin, Trypsin, calcitonin, parathyroid hormone, carbonic anhydrase, ovalbumin, bovine serum albumin (BSA), human serum albumin (HSA), phosphorylase b, alkaline phosphatase, beta-galactosidase, IgG, fibrinogen, poly-L-lysine, IgM, DNA, desmopressin acetate, growth hormone releasing factor (GHRF), somatostatin, antide, Factor VIII, G-CSF/GM-CSF, human growth hormone (hGH), beta interferon, antithrombin III, alpha interferon, alpha interferon 2b.

An inhaler device can be used to deliver a therapeutic protein such as those listed above or other macromolecule-based microspheres to the respiratory airways and lungs of a subject. The protein microspheres can be prepared, for example by contacting an aqueous solution of the protein with a carboxylic acid such as citrate, or sulfate or other counterion and an organic solvent such as isopropanol, and cooling the solution to form the microspheres. The protein can be a therapeutic protein, such as a sialidase, a protease inhibitor, insulin, human growth hormone, calcitonin, rhDNase or parathyroid hormone, and the protein content of the microspheres can be about or at 70% to about or at 90% or more, 95% or more, or at least about 99% or more. For pulmonary administration, the microspheres, for example DAS181 microspheres, can be sized to have a mean diameter in the range of from about 0.5 microns to 5.0 microns, or between about 1 micron to about 2 microns.

Incubation conditions for forming the microspheres can be optimized to incorporate at least about 70%, 75%, 80%, 85%, 90%, 91%, 92%, 93%, 94%, 95%, 96%, 97%, 98%, or 99% or greater of the total amount of macromolecule present in the solution prior to formation of the microspheres, by adjusting parameters including pH, temperature, concentration of macromolecule, or duration of reaction or incubation.

In some embodiments, a molecule or compound that does not produce microspheres of desirable characteristics, can be incorporated into microspheres having desirable characteristics, e.g., of size, delivery profile, mechanical strength, by incorporation or coupling of the compound with a carrier molecule that can form microspheres with desirable characteristics. In some embodiments, the carrier macromolecule is a protein, and the molecule or compound is bound inside and/or on the surface of the microsphere. In some embodiments, the molecule or compound also can serve as the counterion and initiate and/or facilitate the formation of microspheres.

When preparing microspheres containing a protein, a protein stabilizer such as glycerol, fatty acids, sugars such as sucrose, ions such as zinc, sodium chloride, or any other protein stabilizers known to those skilled in the art can be added prior to cooling the cocktail during microsphere formation, n to minimize protein denaturation.

In some embodiments the microspheres can further be coated on the surface with suitable molecules and/or coating agents, such as those that lend resistance to acids, such as digestive acids, or proteases. In other embodiments, the microspheres can be non-covalently coated with compounds such as fatty acids or lipids. The coating can be applied to the microspheres by immersion in the solubilized coating substance, then spraying the microspheres with the substance, or by using other methods known to those of skill in the art. In some embodiments, the fatty acids or lipids are added directly to the microsphere-forming cocktail solution.

Formation of the microspheres by decreasing temperature can be performed by a multitude of conventional methods in batch or continuous modes. Microsphere formation can further be triggered by other methods including, but not limited to, modulating atmospheric pressure, g-force or surface expansion, including seeding. Microsphere formation can occur immediately upon exposure to these conditions or can require an extended period of time as provided herein.

Proteins

Exemplary proteins that can be used to form microparticles by the methods provided herein are described below Sialidases Sialidases, also referred to as neuraminidases and N-acyl-neuraminosylglycohydrolases, are a family exoglycosidases that catalyze the removal of terminal sialic acid residues from sialo-glycoconjugates. Sialic acids are a family of a keto acids with 9-carbon backbones that are usually found at the outermost positions of the oligosaccharide chains attached to glycoproteins and glycolipids. These molecules are involved in a variety of biological functions and processes, such as the regulation of innate immunity, cell adhesion, and the interaction between inflammatory cells and target cells, possibly mediated through the binding of various lectins (Varki et al. (1992) Curr Opin Cell Biol 4:257-266). Sialic acids also are excellent sources of carbon, nitrogen, energy, and precursors of cell wall biosynthesis. Further still, sialic acids on eukaryotic cells can be used as receptors or coreceptors for pathogenic microorganisms, including, but not limited to, influenza virus, parainfluenza virus, some coronavirus and rotavirus *Haemophilus influenzae, Streptococcus pneumonia, Mycoplasma pneumoniae, Moaxella catarrhalis, Helicobacter pylori* and *Pseudomonas aeruginosa*. The most prominent member of the sialic acid family is N-acetylneuraminic acid (Neu5Ac), which is the biosynthetic precursor for most of the other types. Two major linkages between Neu5Ac and the penultimate galactose residues of carbohydrate side chains are found in nature, Neu5Ac $\alpha(2,3)$-Gal and Neu5Ac $\alpha(2,6)$-Gal. Both Neu5Ac $\alpha(2,3)$-Gal and Neu5Ac $\alpha(2,6)$-Gal molecules can be recognized by influenza viruses and used as the receptor through which the virus binds and initiates infection. Human influenza viruses, however, seem to prefer Neu5Ac $\alpha(2,6)$-Gal, while avian and equine influenza viruses predominantly recognize Neu5Ac $\alpha(2,3)$-Gal (Ito et al. (2000) Microobiol Immunol 44:423-730). The human respiratory epithelium expresses both forms of sialic acids, but $\alpha(2,6)$-linked sialic acid is more abundant than $\alpha(2,3)$-linked sialic acid. The low abundance of $\alpha(2,3)$-linked sialic acid is most likely the basis for the species barrier for avian viruses, and indicates that reducing the level of a receptor sialic acid expressed on the airway epithelium would likely reduce the infectivity of an influenza virus. Thus, sialidases, which remove terminal sialic acid residues from sialo-glycoconjugates, present themselves as potential influenza virus therapeutic agents that function to reduce the levels of receptor sialic acids. Sialidases also can act as therapeutic agents for any other pathogen that utilizes sialic acids in the infection process including, but not limited to, *M. pneumoniae, M. catarrhalis, H. pylori, H. influenzae, S. pneumonia, P. aeruginosa*, parainfluenza viruses and some coronaviruses and rotaviruses.

Sialidases tend to be highly substrate specific. They can target particular types of complex molecules, such as glycoproteins or glycolipids; specific sugar linkages (e.g. 2-3, 2-6, or 2-8); or can be sensitive to the nature of the linkage sugar itself (e.g. D-galactose, N-acetyl-D-galactosamine). Substrate molecules include, but are not limited to, oligosaccharides, polysaccharides, glycoproteins, gangliosides, and synthetic molecules. For example, a sialidase can cleave bonds having $\alpha(2,3)$-Gal, $\alpha(2,6)$-Gal, or $\alpha(2,8)$-Gal linkages between a sialic acid residue and the remainder of a substrate molecule. A sialidase also can cleave any or all of the linkages between the sialic acid residue and the remainder of the substrate molecule. Many sialidase proteins have been purified from microbes and higher eukaryotes and of these, several have been shown to catalyze the removal of terminal sialic acid residues than can serve as receptors for pathogenic microorganisms. For example, among the large bacterial sialidases are those that that can degrade the influenza receptor sialic acids Neu5Ac $\alpha(2,6)$-Gal and Neu5Ac $\alpha(2,3)$-Gal, including sialidases from *Clostridium perfringens, Actinomyces viscosus, Arthrobacter ureafaciens*, and *Micromonospora viridifaciens*. Other sialidases that can serve as therapeutic agents include the human sialidases, such as those encoded by the genes NEU2 and NEU4.

Sialidase-GAG Fusion Proteins

Sialidase-GAG fusion proteins are proteins that are made up of a sialidase protein, or catalytically active portion thereof, fused to a glycosaminoglycan (GAG)-binding sequence. As such, these proteins effectively contain an anchoring domain (the GAG-binding sequence) and a therapeutic domain (the sialidase protein, or catalytically active portion thereof). The sialidase-GAG fusion proteins are designed to bind to the epithelium and remove the surrounding sialic acids, and can therefore be used as a therapeutic agent against pathogens that utilize sialic acids in the infection process. The ability of the fusion protein to bind to the epithelium increases its retention when the fusion protein is administered, for example, as an inhalant to treat influenza infection. The GAG-binding sequence acts as an epithelium-anchoring domain that tethers the sialidase to the respiratory epithelium and increases its retention and potency.

Heparan sulfate, closely related to heparin, is a type of glycosaminoglycan (GAG) that is ubiquitously present on cell membranes, including the surface of respiratory epithelium. Many proteins specifically bind to heparin/heparan sulfate, and the GAG-binding sequences in these proteins have been identified. For example, the GAG-binding sequences of human platelet factor 4 (PF4) (SEQ ID NO:3), human interleukin 8 (IL8) (SEQ ID NO:4), human antithrombin III (AT III) (SEQ ID NO:5), human apoprotein E (ApoE) (SEQ ID NO:6), human angio-associated migratory cell protein (AAMP) (SEQ ID NO:7), or human amphiregulin (SEQ ID NO:8) have been shown to exhibit high affinity for heparin (Lee et al. (1991) PNAS 88:2768-2772; Goger et al. (2002) Biochem. 41:1640-1646; Witt et al. (1994) Curr Bio 4:394-400; Weisgraber et al. (1986) J Bio Chem 261:2068-2076). The GAG-binding sequences of these proteins are distinct from their receptor-binding sequences, so they do not induce the biological activities associated with the full-length proteins or the receptor-binding domains. These sequences, or other sequences that can bind heparin/heparan sulfate, can be used as epithelium-anchoring-domains in sialidase-GAG fusion proteins.

In the context of a sialidase-GAG fusion protein, the sialidase can include the entire sialidase protein, or a catalytically active portion thereof. For example, sialidase-GAG fusion protein can contain the 901 amino acid sialidase protein from *A. viscosus* set forth in SEQ ID NO:1. In another example, the sialidase-GAG fusion protein can contain the 394 amino acid catalytically active portion of a sialidase protein from *A. viscosus* set forth in SEQ ID NO:2. The GAG-binding sequence can be linked to the sialidase by recombinant methods. In some examples, the fusion protein can include an amino acid linker, such as four glycine residues. Furthermore, linkage can be via the N- or C-terminus of the GAG-binding sequence, or the N- or C-terminus of the sialidase. Exemplary examples of sialidase-GAG fusion proteins include those polypeptides set forth in SEQ ID NOS: 9-13, and 17. In a further example, the sialidase and GAG-binding sequence components can be linked using chemical or peptide linkers, by any method known in the art.

Proteinase Inhibitor 8

Proteinase inhibitor 8 (PI8), also known as Serpin B8, is a serine protease inhibitor (serpin) Serpins are a large superfamily of structurally related proteins that are expressed in viruses, insects, plants and higher organisms, but not in bacteria or yeast. Serpins regulate the activity of proteases involved in many biological process, including coagulation, fibrinolysis, inflammation, cell migration, and tumorigenesis. They contain a surface-exposed reactive site loop (RSL), which acts as a "bait" for proteases by mimicking a protease substrate sequence. On binding of the target protease to the serpin, the RSL is cleaved, after which the protease is covalently linked to the serpin. The protease in the newly formed serpin-protease complex is inactive (Huntington et al. (2000) Nature 407:923-926).

PI8 is a member of a subfamily of serpins of which chicken ovalbumin is the archtype. Like other serpins that belong to this family, PI8 lacks a typical cleavable N-terminal signal sequence, resulting in a 374 amino acid protein (SEQ ID NO:14) that resides mainly intracellularly. Other members of this human ovalbumin-like subfamily include plasminogen activator inhibitor type 2 (PAI-2), monocyte neutrophil elastase inhibitor (MNEI), squamous cell carcinoma antigen (SCCA)-1, leupin (SCCA-2) maspin (PI5), protease inhibitor 6 (PI6), protease inhibitor (PI9) and bomapin (PI10). Within this family the serpins PI6, PI8, and PI9 show the highest structural homology (up to 68% amino acid identity) (Sprecher et al. (1995) J Biol Chem 270:29854-29861). PI-8 has been shown to inhibit trypsin, thrombin, factor Xa, subtilisin A, furin, and also chymotrypsin in vitro. It is released by platelets and appears to be involved in the regulation of furin activity and, therefore, platelet aggregation (LeBlond et al. (2006) Thromb Haemost 95:243-252).

In addition to their role in the regulation of endogenous biological processes, such as coagulation, serine protease inhibitors also can function to inhibit the biological activities of exogenous microorganisms. For example, a number of serine protease inhibitors have been shown to reduce influenza virus activation in cultured cells, chicken embryos and in the lungs of infected mice. The serpins bind to hemagglutinin (HA) molecules on the surface of the influenza virus and inhibit its activity, thus reducing the infectivity of the virus. For example trypsin inhibitors, such as: aprotinin (Zhimov et al. (2002) J Virol 76:8682-8689), leupeptin (Zhimov et al. (2002) J Virol 76:8682-8689; Tashiro et al. (1987) J Gen Virol 68:2039-2043), soybean protease inhibitor (Barbey-Morel et al. (1987) J Infect Dis 155:667-672), e-aminocaproic acid (Zhimov et al. 1982. Arch Virol 73:263-272) and n-p-tosyl-L-lysine chloromethylketone (TLCK) (Barbey-Morel et al. (1987) J Infect Dis 155:667-672) have all been shown to inhibit influenza virus infection, and are candidate therapeutic agents for use in the treatment of influenza virus infection. Thus, as a related trypsin inhibitor, PI8 also can be used as a therapeutic agent in the treatment of influenza virus infection.

Surface Active Agents

The compositions provided herein can contain one or more surface active agents that are added in an amount sufficient to form a stable emulsion. The appropriate amount of surface active agent is a function of the non-denatured protein, optionally additional active agents for delivery, and other components present in the emulsion, since some agents can have self-emulsifying properties and other agents and components affect surface tension.

The surface active agents for use herein are substances which, when dissolved in an aqueous solution, reduce the surface tension of the solution or the interfacial tension between the aqueous phase and the oil phase, to form a stable oil in water or water in oil emulsion. The surfactant molecules are amphiphilic and contain hydrophilic head groups and hydrophobic tails. The surfactant molecules form various macro-molecular structure in an emulsion, such as micelles, inverse micelles, lipid bilayers (liposomes) and cubosomes. The exact macromolecular structure which is formed depends on the relative sizes of the hydrophilic and hydrophobic regions of the surface active molecule. In certain embodiments, the surface active agent is selected from sodium lauryl sulfate; sorbitan laurate, sorbitan palmitate, sorbitan stearate (available under the tradename Span® 20-40-60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20-40-60 etc.); benzalkonium chloride, mixed chain phospholipids, cationic lipids, oligolipids, phospholipids, carnitines, sphingosines, sphingomyelins, ceramides, glycolipids, lipoproteins, apoproteins, amphiphilic proteins, amphiphilic peptides, amphiphilic synthetic polymers, and combinations thereof. Other exemplary surface active agents for use herein include, but are not limited to i) Natural lipids, i.e. Cholesterol, Sphingosine and Derivatives, Gangliosides, Sphingosine derivatives (Soy Bean), Phytosphingosine and derivatives (Yeast), Choline (Phosphatidylcholine), Ethanolamine (Phosphatidylethanolamine), Glycerol (Phosphatidyl-DL-glycerol), Inositol (Phosphatidylinositol), Serine (Phosphatidylserine (Sodium Salt)), Cardiolipin, Phosphatidic Acid, Egg Derived, Lyso (Mono Acyl) Derivatives (Lysophosphatides), Hydrogenated Phospholipids, Lipid Tissue Extracts, ii) Synthetic lipids, i.e. Asymmetric Fatty Acid, Symmetric Fatty Acid—Saturated Series, Symmetric Fatty Acid—Unsaturated Series, Acyl Coenzyme A (Acetoyl Coenzyme A, Butanoyl Coenzyme A, Crotanoyl Coenzyme A, Hexanoyl Coenzyme A, Octanoyl Coenzyme A, Decanoyl Coenzyme A, Lauroyl Coenzyme A, Myristoyl Coenzyme A, Palmitoyl Coenzyme A, Stearoyl Coenzyme A, Oleoyl Coenzyme A, Arachidoyl Coenzyme A, Arachidonoyl Coenzyme A, Behenoyl Coenzyme A, Tricosanoyl Coenzyme A, Lignoceroyl Coenzyme A, Nervonoyl Coenzyme A, Hexacosanoyl Coenzyme A, iii) Sphingolipids, i.e. D-erythro (C-18) Derivatives (Sphingosine, such as: D-erythro Sphingosine (synthetic), Sphingosine-1-Phosphate, N,N Dimethylsphingosine, N,N,N-Trimethylsphingosine, Sphingosylphosphorylcholine, Sphingomyelin and Glycosylated Sphingosine), Ceramide Derivatives (Ceramides, D-erythro Ceramide-1-Phosphate, Glycosulated Ceramides), Sphinganine (Dihydrosphingosine) (Sphinganine-1-Phosphate, Sphinganine (C20), D-erythro Sphinganine, N-Acyl-Sphinganine C2, N-Acyl-Sphinganine C8, N-acyl-Sphinganine C16, N-Acyl-Sphinganine C18, N-Acyl-Sphinganine C24, N-Acyl-Sphinganine C24:1), Glycosylated (C18) Sphingosine and Phospholipid Derivatives (Glycosylated-Sphingosine) (Sphingosine, βD-Glucosyl, Sphingosine, βD-Galactosyl, Sphingosine, βD-Lactosyl), Glycosylated-Ceramide (D-Glucosyl-β1' Ceramide (C8), D-Galactosyl-β1' Ceramide (C8), D-Lactosyl-β1-1' Ceramide (C8), D-Glucosyl-β1-1' Ceramide (C12), D-Galactosyl-β1-1' Ceramide (C12), D-Lactosyl-β1-1' Ceramide (C12)), Glycosylated-Phosphatidylethanolamine (1,2-Dioleoyl-sn-Glycero-3-Phosphoethanolamine-N-Lactose), D-erythro (C17) Derivatives (D-erythro Sphingosine, D-erythro Sphingosine-1-phosphate), D-erythro (C20) Derivatives (D-erythro Sphingosine), L-threo (C18) Derivatives (L-threo Sphingosine, Safingol (L-threo Dihydrosphingosine)), Sphingosine Derivatives (Egg, Brain & Milk) (D-erythro-Sphingosine, Sphingomyelin, Ceramides, Cerebrosides, Brain Sulfatides), Gangliosides (Gangliosides Structures, Gangliosides—Ovine Brain, Gangliosides—Porcine Brain), Sphingosine Derivatives (Soy Bean) (Glucosylceramide), Phytosphingosine Derivatives (Yeast) (Phytosphingosine, D-ribo-Phytosphingosine-1-Phosphate, N-Acyl Phytosphingosine C2, N-Acyl Phytosphingosine C8, N-Acyl Phytosphingosine C18, iv) Acyl coenzyme A, i.e. Acetoyl Coenzyme A (Ammonium Salt), Butanoyl Coenzyme A (Ammonium Salt), Crotanoyl Coenzyme A (Ammonium Salt), Hexanoyl Coenzyme A (Ammonium Salt), Octanoyl Coenzyme A (Ammonium Salt), Decanoyl Coenzyme A (Ammonium Salt), Lauroyl Coenzyme A (Ammonium Salt), Myristoyl Coenzyme A (Ammonium Salt), Palmitoyl Coenzyme A (Ammonium Salt), Stearoyl Coenzyme A (Ammonium Salt), Oleoyl Coenzyme A (Ammonium Salt), Arachidoyl Coenzyme A (Ammonium Salt), Arachidonoyl Coenzyme A (Ammonium Salt), Behenoyl Coenzyme A (Ammonium Salt), Tricosanoyl Coenzyme A (Ammonium Salt), Lignoceroyl Coenzyme A (Ammonium Salt), Nervonoyl Coenzyme A (Ammonium Salt), Hexacosanoyl Coenzyme A (Ammonium Salt), Docosahexaenoyl Coenzyme A (Ammonium Salt), v) Oxidized lipids, i.e. 1-Palmitoyl-2-Azelaoyl-sn-Glycero-3-Phosphocholine, 1-O-Hexadecyl-2-Azelaoyl-sn-Glycero-3-Phosphocholine, 1-Palmitoyl-2-Glutaroyl-sn-Glycero-3-Phosphocholine (PGPC), 1-Palmitoyl-2-(9'-oxo-Nonanoyl)-sn-Glycero-3-Phosphocholine, 1-Palmitoyl-2-(5'-oxo-Valeroyl)-sn-Glycero-3-Phosphocholine, vi) Ether lipids, i.e.: Diether Lipids (Dialkyl Phosphatidylcholine, Diphytanyl Ether Lipids), Alkyl Phosphocholine (Dodedylphosphocholine), O-Alkyl diacylphosphatidylcholinium (1,2-Diacyl-sn-Glycero-3-Ethylphosphocholine), Synthetic PAF & Derivatives (1-Alkyl-2-Acyl-Glycero-3-Phosphocholine & Derivatives), vii) Fluorescent lipids, i.e.: Glycerol Based (Phosphatidylcholine (NBD), Phosphatidic Acid (NBD), Phosphatidylethanolamine (NBD), Phosphatidylglycerol (NBD), Phosphatidylserine (NBD)), Sphingosine Based (Ceramide (NBD), Sphingomyelin (NBD), Phytosphingosine (NBD), Galactosyl Cerebroside (NBD)), Headgroup Labeled Lipids (Glycerol Based) (Phosphatidylethanolamine (NBD), Phosphatidylethanolamine (Lissamine Rhodamine B), Dioleoyl Phosphatidylethanolamine (Dansyl, Pyrene, Fluorescein), Phosphatidylserine (NBD), Phosphatidylserine (Dansyl)), 25-NBD-Cholesterol, viii) Other lipids including, but not limited to Lecithin, Ultralec-P (ADM), Soy powder, ix) Surfactants including, but not limited to polyethylene glycol 400; sodium lauryl sulfate; sorbitan laurate, sorbitan palmitate, sorbitan stearate (available under the tradename Span® 20-40-60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20-40-60 etc.); benzalkonium chloride.

In certain embodiments, the phospholipids for use are phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In certain embodiments, the surface active agent is selected from polysorbate-80, lecithin and phosphatidylcholine. The surface active agents are present in an amount sufficient to form a stable emulsion.

The amount of surface active agent can be empirically determined and is a function of the agent selected, the desired form of the resulting composition. The amount include can be from less than 0.1% by weight up to 35% or more. In certain embodiments, the surface active agent is present at a concentration of about 1%, 2%, 3%, 4%, 5%, 6%, 7%, 8%, 9%, 10%, 15%, 20%, 25% by weight up to about 30% by weight of the total weight of the composition. In certain embodiments, the surface active agent is present at a concentration of about 1 weight % up to about 20 weight % of the total weight of the composition. In certain embodiments, the surface active agent is present at a concentration of about 1 weight % up to about 15 weight % of the total weight of the composition. In other embodiments, the surface active agent is present at a concentration of about 1 weight % up to about 10 weight % of the total weight of the composition. In other embodiments, the surface active agent is present at a concentration of about 1 weight % up to about 8 weight % of the total weight of the composition. In other embodiments, the surface active agent is present at a concentration of about 1 weight % up to about 6 weight % of the total weight of the composition. In other embodiments, the surface active agent is present at a concentration of about 1 weight % up to about 4 weight % of the total weight of the composition. In other embodiments, the surface active agent is present at a concentration of about 20 weight % of the total weight of the composition. In other embodiments, the surface active agent is present at a concentration of about 15 weight % of the total weight of the composition. In other embodiments, the surface active agent is present at a concentration of about 13 weight % of the total weight of the composition. In other embodiments, the surface active agent is present at a concentration of about 11 weight % of the total weight of the composition. In other embodiments, the surface active agent is present at a concentration of about 8 weight % of the total weight of the composition. In other embodiments, the surface active agent is present at a concentration of about 6 weight % of the total weight of the composition. In other embodiments, the surface active agent is present at a concentration of about 4 weight % of the total weight of the composition. In other embodiments, the surface active agent is present at a concentration of about 2 weight % of the total weight of the composition. In other embodiments, the surface active agent is present at a concentration of about 1 weight % of the total weight of the composition.

The stable emulsions provided herein can contain one or more delivery vehicles selected from among micelles, liposomes and cubosomes and mixtures thereof, or macromolecular assemblies of non-denatured proteins such as tubes, helices, spheres and the like, that can encapsulate additional nutrients or active agents. The delivery vehicles encapsulating the active agent are then absorbed in the epithelium where the non-denatured proteins and/or additional nutrients/active agents are delivered.

Optional Additional Agents

The compositions provided herein can optionally, in addition to non-denatured proteins, contain one or more pharmaceutical or nutraceutical or other such agent for ingestion by a subject. Generally the agents are those that have a function in a host, e.g., immune regulation, regulation of biochemical processes, or enzymatic activity. Any agent that can be formulated as described herein can be administered in the compositions provided herein. Where the agent is a therapeutic the compositions contain a therapeutically effective amount of an agent to be delivered. The particular amount of active agent in a dosage will vary widely according to the nature of the active agent, the nature of the condition being treated, the age and size of the subject, and other parameters.

Generally, the amount of additional active agent or nutrient besides the non-denatured proteins in the composition will vary from less than about 0.01% by weight to about 20% by weight of the composition, or more and typically are formulated for single dosage administration. A single dosage can vary from about 0.01 µg to 10 mg of an agent per kilogram of body weight of the host, with dosages from about 0.1 µg to 1 mg/kg being commonly employed. These concentrations, however, are general guidelines only and particular amounts and dosages may be selected based on the active agent being administered, the condition being treated, and the treatment regimen being employed means an amount of a drug or an active agent that is sufficient to provide the desired local or systemic effect and performance at a reasonable benefit/risk ratio to a subject attending any medical treatment.

Agents can be selected from inorganic and organic drugs including, but not limited to drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems, histamine systems, and the like. The active agents that can be delivered using the compositions provided herein include, but are not limited to, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements.

The level of agent to be delivered is from about 0.01% up to about 50%, from about 0.1% up to about 40%, from about 0.1% up to about 30%, from about 0.1% up to about 20%, from about 0.1% up to about 10%, from about 0.1% up to about 9%, from about 0.1% up to about 8%, from about 0.1% up to about 7%, from about 0.1% up to about 6%, from about 0.1% up to about 5%, from about 0.1% up to about 4%, from about 0.1% up to about 3%, from about 0.1% up to about 2%, from about 0.1% up to about 1% by weight of the composition. The agent to be delivered can be water soluble, slightly water soluble, or oil soluble. In certain embodiments, the agent to be delivered is selected from anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, non denatured whey protein, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements.

In certain embodiments, the active agent is selected as follows:

α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline;

β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol;

α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine;

β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol;

Alcohol deterrents such as Calcium Cyanamide Citrated, Disulfuram, Nadide and Nitrefazole;

Aldose reductase inhibitors such as Epalrestat, Ponalrestat, Sorbinil and Tolrestat;

Anabolics such as Androisoxazole, Androstenediol, Bolandiol, Bolasterone, Clostebol, Ethylestrenol; Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone;

Analgesics (dental) such as Chlorobutanol, Clove and Eugenol;

Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydrocodone Bitartrate, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papavereturn, Pentazocine, Phenadoxone, Phenazocine, Pheoperidine, Piminodine, Piritramide, Proheptazine, Promedol, Properidine, Propiram, Propoxyphene, Sufentanil and Tilidine;

Analgesics (non-narcotic) such as Acetaminophen, Acetaminosalol, Acetanilide, Acetylsalicylsalicylic Acid, Alclofenac, Alminoprofen, Aloxiprin, Aluminum Bis(acetylsalicylate), Aminochlorthenoxazin, 2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac;

Androgens such as Androsterone, Boldenone, Dehydroepiandrosterone, Fluoxymesterone, Mestanolone, Mesterolone, Methandrostenolone, 17-Methyltestosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate and Tiomesterone;

Anesthetics such as Acetamidoeugenol, Alfadolone Acetate, Alfaxalone, Amucaine, Amolanone, Amylocalne Hydrochloride, Benoxinate, Benzocaine, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocalne, Procaine, Propanidid, Propanocaine, Proparacaine, Propipocaine, Propofol, Propoxycaine Hydrochloride, Pseudococaine, Pyrrocaine, Quinine Urea Hydrochloride, Risocaine, Salicyl Alcohol, Tetracaine Hydrochloride, Thialbarbital, Thimylal, Thiobutabarbital, Thiopental Sodium, Tolycaine, Trimecaine and Zolamine;

Anorexics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phendimetrazine Tartrate, Phenmetrazine, Phenpentermine, Phenylpropanolamine Hydrochloride and Picilorex;

Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine;

Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dyrnanthine, Gentian Violet, 4-Hexylresorcinol, Kainic Acid, Mebendazole, 2-Napthol, Oxantel, Papain, piperazine, piperazine Adipate, piperazine Citrate, piperazine Edetate Calcium, piperazine Tartrate, Pyrantel, Pyrvinium Pamoate, α-Santonin, Stilbazium Iodide, Tetrachloroethylene, Tetramisole, thiabendazole, Thymol, Thymyl N-Isoamylcarbamate, Triclofenol piperazine and Urea Stibamine;

Anthelmintics (Onchocerca) such as Ivermectin and Suramin Sodium;

Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen and Urea Stibamine;

Anthelmintic (Trematodes) such as Anthiolimine and Tetrachloroethylene;

Antiacne drugs such as Adapelene, Algestone Acetophenide, Azelaic Acid, Benzoyl Peroxide, Cyoctol, Cyproterone, Motretinide, Resorcinol, Retinoic Acid, Tetroquinone and Tretinonine;

Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol;

Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Timidazole;

Antiandrogens such as Bifluranol, Cyoctol, Cyproterone, Delmadinone Acetate, Flutimide, Nilutamide and Oxendolone;

Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil;

Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encamide, Esmolol, Flecamide, Gallopamil, Hydroquinidine, Indecamide, Indenolol, Ipratropium Bromide, Lidocaine, Lorajmine, Lorcamide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocamide, Verapamil, Viquidil and Xibenolol;

Antiarteriosclerotics such as Pyridinol Carbamate;

Antiarthritic/Antirheumatics such as Allocupreide Sodium, Auranofin, Aurothioglucose, Aurothioglycanide, Azathioprine, Calcium 3-Aurothio-2-propanol-1-sulfonate, Celecoxib, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine;

Antibacterial (antibiotic) drugs including: Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin;

β-Lactams, including: Carbapenems such as Imipenem;

Cephalosporins such as Cefactor, Cefadroxil, Cefamandole, Cefatrizine, Cefazedone, Cefazolin, Cefixime, Cefinenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefinetazole, Cefminox, Cefetan and Cefoxitin;

Monobactams such as Aztreonam, Carumonam and Tigemonam;

Oxacephems such as Flomoxef and Moxolactam;

Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocill in, Cloxacill in, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin 0, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithroimycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin;

Antibacterial drugs (synthetic), including: 2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N_2$ Formylsulfisomidine, $N^2$-β-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, N-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N,N' digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol;

Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1,2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide;

Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, Garbapentin, 5-Hydroxytryptophan, Lamotrigine, Lomactil, Magnesium Bromide, Magnesium Sulfate, Mephenyloin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenyloin, Phethenylate Sodium, Potassium Bromide, Pregabatin, Primidone, Progabide, Sodium Bromide, Sodium Valproate, *Solanum*, Strontium Bromide, Suclofenide, Sulthiame, Tetrantoin, Tiagabine, Trimethadione, Valproic Acid, Valpromide, Vigabatrin and Zonisamide;

Antidepressants, including: Bicyclics such as Binedaline, Caroxazone, Citalopram, Dimethazan, Indalpine, Fencamine, Fluvoxamine Maleate, Indeloxazine Hydrochcloride, Nefopam, Nomifensine, Oxitriptan, Oxypertine, Paroxetine, Sertraline, Thiazesim, Trazodone, Venlafaxine and Zometapine;

Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;

Tetracyclics such as Maprotiline, Metralindole, Mianserin and Oxaprotiline;

Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine;

Antidiabetics, including: Biguanides such as Buformin, Metformin and Phenformin;

Hormones such as Glucagon, Insulin, Insulin Injection, Insulin Zinc Suspension, Isophane Insulin Suspension, Protamine Zinc Insulin Suspension and Zinc Insulin Crystals;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol;

Antidiarrheal drugs such as Acetyltannic Acid, Albumin Tannate, Alkofanone, Aluminum Salicylates—Basic, Catechin, Difenoxin, Diphenoxylate, Lidamidine, Loperamide, Mebiquine, Trillium and Uzarin;

Antidiuretics such as Desmopressin, Felypressin, Lypressin, Ornipressin, Oxycinchophen, Pituitary—Posterior, Terlipressin and Vasopressin;

Antiestrogens such as Delmadinone Acetate, Ethamoxytriphetol, Tamoxifen and Toremifene;

Antifungal drugs (antibiotics), including: Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, PyrroInitrin, Siccanin, Tubercidin and Viridin;

Antifungal drugs (synthetic), including: Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;

Triazoles such as Fluconazole, Itraconazole and Terconazole; and others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate;

Antiglaucoma drugs such as Acetazolamide, Befunolol, Betaxolol, Bupranolol, Carteolol, Dapiprazole, Dichlorphenamide, Dipivefrin, Epinephrine, Levobunolol, Methazolamide, Metipranolol, Pilocarpine, Pindolol and Timolol;

Antigonadotropins such as Danazol, Gestrinone and Paroxypropione;

Antigout drugs such as Allopurinol, Carprofen, Colchicine, Probenecid and Sulfinpyrazone;

Antihistamines, including: Alkylamine derivatives such as Acrivastine, Bamipine, Brompheniramine, Chlorpheniramine, Dimethindene, Metron S, Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

piperazines such as Cetirizine, Chlorcyclizine, Cinnarizine, Clocinizine and Hydroxyzine;

Tricyclics, including: Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Fluticasone Propionate, Mebhydroline, Phenindamine, Terfenadine and Tritoqualine;

Antihyperlipoproteinemics, including: Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Fluvastatin, Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, β-Benzalbutyramide, Carnitine, Chondroitin Sulfate, Clomestone, Detaxtran, Dextran Sulfate Sodium, 5,8,11,14,17-Eicosapentaenoic Acid, Eritadenine, Furazbol, Meglutol, Melinamide, Mytatrienediol, Ornithine, γ-Oryzanol, Pantethine, Penataerythritol Tetraacetate, α-Phenylbutyramide, Pirozadil, Probucol, α-Sitosterol, Sultosilic Acid, piperazine Salt, Tiadenol, Triparanol and Xenbucin;

Antihypertensive drugs, including: Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;

N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipirne;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Phentolamine Mesylate, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidiunum Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, γ-Aminobutyric Acid, Bufeniode, Candesartan, Chlorthalidone, Cicletaine, Ciclosidomine, Cryptenamine Tannates, Eprosartan, Fenoldopam, Flosequinan, Indoramin, Irbesartan, Ketanserin, Losartan, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase, Urapidil and Valsartan;

Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital and 2-Thiouracil;

Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine;

Antihypothyroid drugs such as Levothyroxine Sodium, Liothyronine, Thyroid, Thyroidin, Thyroxine, Tiatricol and TSH;

Anti-Inflammatory (non-steroidal) drugs, including: Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid;

Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizon, Butibufen, Fenbufen and Xenbucin;

Arylcarboxylic acids such as Clidanac, Ketorolac and Tinoridine;

Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;

Thiazinecarboxamides such as Droxicam, Isoxicam, Piroxicam and Tenoxicam; and others such as ∈-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap;

Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic;

Antimigraine drugs such as Alpiropride, Dihydroergotamine, Eletriptan, Ergocornine, Ergocorninine, Ergocryptine, Ergot, Ergotamine, Flumedroxone acetate, Fonazine, Lisuride, Methysergid(e), Naratriptan, Oxetorone, Pizotyline, Rizatriptan and Sumatriptan;

Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide;

Antineoplastic drugs, including: Alkylating agents, such as Alkyl sulfonates such as Busulfan, Improsulfan and Piposulfan;

Aziridines such as Benzodepa, Carboquone, Meturedepa and Uredepa;

Ethylenimines and methylmelamines such as Altretamine, Triethylenemelamine, Triethylenephosphoramide, Triethylenethiophosphoramide and Trimethylolomelamine;

Nitrogen mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;

Nitrosoureas such as Carmustine, Chlorozotocin, Fotemustine, Lomustine, Nimustine and Ranimustine; and others such as Camptothecin, Dacarbazine, Mannomustine, Mitobronitol, Mitolactol and Pipobroman;

Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin;

Antimetabolites, including: Folic acid analogs such as Denopterin, Methotrexate, Pteropterin and Trimetrexate;

Purine analogs such as Fludarabine, 6-Mercaptopurine, Thiamiprine and Thioguanaine; and Pyrimidine analogs such as Ancitabine, Azacitidine, 6-Azauridine, Carmofur, Cytarabine, Doxifluridine, Enocitabine, Floxuridine Fluoroouracil and Tegafur;

Enzymes such as L-Asparaginase; and others such as Aceglatone, Amsacrine, Bestrabucil, Bisantrene, Bryostatin 1, Carboplatin, Cisplatin, Defofamide, Demecolcine, Diaziquone, Elformithine, Elliptinium Acetate, Etoglucid, Etoposide, Gallium Nitrate, Hydroxyurea, Interferon-α, Interferon-β, Interferon-γ, Interleukine-2, Lentinan, Letrozole, Lonidamine, Mitoguazone, Mitoxantrone, Mopidamol, Nitracrine, Pentostatin, Phenamet, Pirarubicin, Podophyllinicc Acid, 2-Ethylhydrazide, Polynitrocubanes, Procarbazine, PSK7, Razoxane, Sizofuran, Spirogermanium, Taxol, Teniposide, Tenuazonic Acid, Triaziquone, 2.2'.2"-Trichlorotriethylamine, Urethan, Vinblastine, Vincristine, Vindesine and Vinorelbine;

Antineoplastic (hormonal) drugs, including: Androgens such as Calusterone, Dromostanolone Propionate, Epitiostanol, Mepitiostane and Testolactone;

Antiadrenals such as Aminoglutethimide, Mitotane and Trilostane;

Antiandrogens such as Flutamide and Nilutamide; and

Antiestrogens such as Tamoxifen and Toremifene;

Antineoplastic adjuncts including folic acid replenishers such as Frolinic Acid;

Antiparkinsonian drugs such as Amantadine, Benserazide, Bietanautine, Biperiden, Bromocriptine, Budipine, Cabergoline, Carbidopa, Deprenyl (a/k/a L-deprenyl, L-deprenil, L-deprenaline and selegiline), Dexetimide, Diethazine, Diphenhydramine, Droxidopa, Ethopropazine, Ethylbenzhydramine, Levodopa, Naxagolide, Pergolide, Piroheptine, Pramipexole, Pridinol, Prodipine, Quinpirole, Remacemide, Ropinirole, Terguride, Tigloidine and Trihexyphenidyl Hydrochloride;

Antipheochromocytoma drugs such as Metyrosine, Phenoxybenzamine and Phentolamine;

Antipneumocystis drugs such as Efformithine, Pentamidine and Sulfamethoxazole;

Antiprostatic hypertrophydrugs such as Gestonorone Caproate, Mepartricin, Oxendolone and Proscar7;

Antiprotozoal drugs (Leshmania) such as Antimony Sodium Gluconate, Ethylstibamine, Hydroxystilbamidine, N-Methylglucamine, Pentamidine, Stilbamidine and Urea Stibamine;

Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Timidazole;

Antiprotozoal drugs (Trypanosma) such as Benznidazole, Eflornithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide;

Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine;

Antipsoriatic drugs such as Acitretin, Ammonium Salicylate, Anthralin, 6-Azauridine, Bergapten(e), Chrysarobin, Etretinate and Pyrogallol;

Antipsychotic drugs, including: Butyrophenones such as Benperidol, Bromperidol, properidol, Fluanisone, Haloperidol, Melperone, Moperone, Pipamperone, Sniperone, Timiperone and Trifluperidol;

Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;

Thioxanthenes such as Chlorprothixene, Clopenthixol, Flupentixol and Thiothixene;

other tricyclics such as Benzquinamide, Carpipramine, Clocapramine, Clomacran, Clothiapine, Clozapine, Opipramol, Prothipendyl, Tetrabenazine, and Zotepine; and others such as Alizapride, Amisulpride, Buramate, Fluspirilene, Molindone, Penfluridol, Pimozide, Spirilene and Sulpiride;

Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 51-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine;

Antirickettsial drugs such as p-Aminobenzoic Acid, Chloramphenicol, Chloramphenicol Palmitate, Chloramphenicol Pantothenate and Tetracycline;

Antiseborrheic drugs such as Chloroxine, 3-O-Lauroylpyridoxol Diacetate, Piroctone, Pyrithione, Resorcinol, Selenium Sulfides and Tioxolone;

Antiseptics, including: Guanidines such as Alexidine, Ambazone, Chlorhexidine and Picloxydine;

Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Fluorosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium;

Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate(II), Potassium Triiodomercurate (II) Solution, Thimerfonate Sodium and Thimerosal;

Nitrofurans such as Furazolidone, 2-(Methoxymethyl)-5-nitrofuran, Nidroxyzone, Nifuroxime, Nifurzide and Nitrofurazone;

Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Napthyl Salicylate, 2-Napthyl Salicylate, 2,4,6-Tribromo-m-cresol, and 3',4',5'-Trichlorosalicylanilide;

Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol7, Noxytiolin, Ornidazole, β-Propiolactone, α-Terpineol;

Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Brcmide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, *Trifolium*, Trimebutine, N,N-lTrimethyl-3,3-diphenyl-propylamine, Tropenzile, Trospium Chloride and Xenytropium Bromide;

Antithrombotic drugs such as Anagrelide, Argatroban, Cilostazol, Chrysoptin, Daltroban, Defibrotide, Enoxaparin, Fraxiparine-7, Indobufen, Lamoparan, Ozagrel, Picotamide, Plafibride, Reviparin, Tedelparin, Ticlopidine, Triflusal and Warfarin;

Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, propropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol;

Antiulcerative drugs such as Aceglutamide Aluminum Complex, ∈-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, γ-Oryzanol, Pifamine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide and Zolimidine;

Antiurolithic drugs such as Acetohydroxamic Acid, Allopurinol, Potassium Citrate and Succinimide;

Antivenin drugs such as Lyovac7 Antivenin;

Antiviral drugs, including: Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Penciclovir, Trifluridine, Vidrarbine and Zidovudiine; and others such as Acetylleucine Monoethanolamine, Amantadine, Amidinomycin, Cosalane, Cuminaldehyde Thiosemicarbzone, Foscarnet Sodium, Imiquimod, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid;

Anxiolytic drugs, including: Arylpiperazines such as Buspirone, Gepirone, Ipsapirone and Tondospirone;

Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;

Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron;

Benzodiazepine antagonists such as Flumazenil;

Bronchodilators, including: Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Salmeterol, Soterenol, Terbutaline and Tulobuterol;

Quaternary ammonium compounds such as Bevonium Methyl Sulfate, Clutropium Bromide, Ipratropium Bromide and Oxitropium Bromide;

Xanthine derivatives such as Acefylline, Acefylline piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Montekulast, Methoxyphenanime, Tretoquinol and Zafirkulast;

Calcium channel blockers, including: Arylalkylamines such as Bepridil, Ditiazem, Fendiline, Gallopanil, Prenylamine, Terodiline and Verapamil;

Dihydropyridine derivatives such as Felodipine, Isradipine, Nicardipine, Nifedipine, Nilvadipine, Nimodipine, Nisoldipine and Nitrendipine;

Piperazine derivatives such as Cinnarizine, Flunarisine and Lidoflazine; and others such as Bencyclane, Etafenone and Perhexyline;

Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate;

Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol;

Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine;

Cholecystokinin antagonists such as Proglumide;

Cholelitholytic agents such as Chenodiol, Methyl tert-Butyl Ether, Monooctanoin and Ursodiol;

Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4A'-Oxydi-2-butanol, Piprozolin, Prozapine, 4-Salicyloylmorpholine, Sincalide, Taurocholic Acid, Timonacic, Tocamphyl, Trepibutone and Vanitiolide;

Cholinergic agents such as Aceclidine, Acetylcholine Bromide, Acetylcholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isofluorophate, Methacholine chloride, Muscarine, Neostigmine, Oxapropanium Iodide, Physostigmine and Pyridostigmine Bromide;

Cholinesterase inhibitors such as Ambenonium Chloride, Distigmine Bromide and Galanthamine;

Cholinesterase reactivators such as Obidoximine Chloride and Pralidoxime Chloride;

Central nervous system stimulants and agents such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Fluorothyl, Galanthamine, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone;

Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline;

Dental agents, including: Bisphosphonates (anti-periodontal disease and bone resorption) such as Alendronate, Clodronate, Etidronate, Pamidronate and Tiludronate; Carries Prophylactics such as Arginine and Sodium Fluoride;

Desensitizing Agents such as Potassium Nitrate and Citrate Oxalate;

Depigmentors such as Hydroquinine, Hydroquinone and Monobenzone;

Diuretics, including: Organomercurials such as Chlormerodrin, Meralluride, Mercamphamide, Mercaptomerin Sodium, Mercumallylic Acid, Mercumatilin Sodium, Mercurous Chloride and Mersalyl;

Pteridines such as Furterene and Triamterene;

Purines such as Acefylline, 7-Morpholinomethyltheophylline, Pamabrom, Protheobromine and Theobromine;

Steroids such as Canrenone, Oleandrin and Spironolactone;

Sulfonamide derivatives such as Acetazolmide, Ambuside, Azosemide, Bumetanide, Butazolamide, Chloraminophenamide, Clofenamide, Clopamide, Clorexolene, Diphenylmethane-4,4'-disulfonamide, Disulfamide, Ethbxzolamide, Furosemide, Indapamide, Mefruside, Methazolamide, Piretanide, Quinethazone, Torasemide, Tripamide and Xipamide;

Uracils such as Aminometradine and Amisometradine;

others such as Amanozine, Amiloride, Arbutin, Chlorazanil, Ethacrynic Acid, Etozolin, Hydracarbazine, Isosorbide, Mannitol, Metochalcone, Muzolimine, Perhexyline, Ticrynafen and Urea;

Dopamine receptor agonists such as Bromocriptine, Dopexamine, Fenoldopam, Ibopamine, Lisuride, Naxagolide and Pergolide;

Ectoparasiticides such as Amitraz, Benzyl Benzoate, Carbaryl, Crotamiton, DDT, Dixanthogen, Isobornyl Thiocyanoacetate-Technical, Lime Sulfurated Solution, Lindane, Malathion, Mercuric Oleate, Mesulphen and Sulphur-Pharmaceutical;

Enzymes, including: Digestive enzymes such as α-Amylase (Swine Pancreas), Lipase, Pancrelipase, Pepsin and Rennin;

Mucolytic enzymes such as Lysozyme;

Penicillin inactivating enzymes such as Penicillinase; and

Proteolytic enzymes such as Collagenase, Chymopapain, Chymotrypsins, Papain and Trypsin;

Enzyme inducers (hepatic) such as Flumecinol;

Estrogens, including: Nonsteroidal estrogens such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril and Methestrol; and Steroidal estrogens such as Colpormon, Conjugated Estrogenic Hormones, Equilenin, Equilin, Estradiol, Estradiol Benzoate, Estradiol 17β-Cypionate, Estriol, Estrone, Ethinyl Estradiol, Mestranol, Moxestrol, Mytatrienediol, Quinestradiol and Quinestrol;

Gastric secretion inhibitors such as Enterogastrone and Octreotide;

Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, Hydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide;

Gonad-Stimulating principles such as Buserelin, Clomiphene, Cyclofenil, Epimestrol, FSH, HCG and LH-RH;

Gonadotropic hormones such as LH and PMSG;

Growth hormone inhibitors such as Octreotide and Somatostatin;

Growth hormone releasing factors such as Semorelin;

Growth stimulants such as Somatotropin;

Hemolytic agents such as Phenylhydrazine and Phenylhydrazine Hydrochloride;

Heparin antagonists such as Hexadimethrine Bromide and Protamines;

Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin;

Immunomodulators such as Amiprilose, Bucillamine, Ditiocarb Sodium, Inosine Pranobex, Interferon-γ, Interleukin-2, Lentinan, Muroctasin, Platonin, Procodazole, Tetramisole, Thymomodulin, Thymopentin and Ubenimex;

Immunosuppressants such as Azathioprine, Cyclosporins and Mizoribine;

Ion exchange resins such as Carbacrylic Resins, Cholestyramine Resin, Colestipol, Polidexide, Resodec and Sodium Polystyrene Sulfonate;

Lactation stimulating hormone such as Prolactin;

LH-RH agonists such as Buserelin, Goserelin, Leuprolide, Nafarelin, and Triptorelin;

Lipotropic agents such as N-Acetylmethionine, Choline Chloride, Choline Dehydrocholate, Choline Dihydrogen Citrate, Inositol, Lecithin and Methionine;

Lupus erythematosus suppressants such as Bismuth Sodium Triglycollamate, Bismuth Subsalicylate, Chloroquine and Hydroxychloroquine;

Mineralcorticoids such as Aldosterone, Deoxycorticosterone, Deoxycorticosterone Acetate and Fludrocortisone;

Miotic drugs such as Carbachol, Physostigmine, Pilocarpine and Pilocarpus;

Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine;

Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol;

Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Lauexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine;

Narcotic antagonists such as Amiphenazole, Cyclazocine, Levallorphan, Nadide, Nalmfene, Nalorphine, Nalorphine Dinicotinate, Naloxone and Naltrexone;

Neuroprotective agents such as Dizocilpine;

Nootropic agents such as Aceglutamide, Acetylcarnitine, Aniracetam, Bifematlane, Exifone, Fipexide, Idebenone, Indeloxazune Hydrochloride, Nizofenone, Oxiracetam, Piracetam, Propentofylline, Pyritinol and Tacrine;

Ophthalmic agents such as 15-ketoprostaglandins;

Ovarian hormone such as Relaxin;

Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2\alpha}$ and Sparteine;

Pepsin inhibitors such as Sodium Amylosulfate;

Peristaltic stimulants such as Cisapride;

Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Fluorogestone Acetate, Gestodene, Gestonorone Caproate, Haloprogesterone, 17-Hydroxy-16-methyleneprogesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone;

Prolactin inhibitors such as Metergoline;

Prostaglandins and prostaglandin analogs such as Arbaprostil, Carboprost, Enprostil, Bemeprost, Limaprost, Misoprostol, Ornoprostil, Prostacyclin, Prostaglandin $E_1$, Prostaglandin $E_2$, Prostagland in $F_{2\alpha}$, Rioprostil, Rosaprostol, Sulprostone and Trimoprostil;

Protease inhibitors such as Aprotinin, Camostat, Gabexate and Nafamostat;

Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine;

Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside;

Sedatives and hypnotics, including: Acyclic ureides such as Acecarbromal, Apronalide, Bomisovalum, Capuride, Carbromal and Ectylurea;

Alcohols such as Chlorhexadol, Ethchlorvynol, Meparfynol, 4-Methyl-5-thiazoleethanol, tert-Pentyl Alcohol and 2,2,2-Trichloroethanol;

Amides such as Butoctamide, Diethylbromoacetamide, Ibrotamide, Isovaleryl Diethylamide, Niaprazine, Tricetamide, Trimetozine, Zolpidem and Zopiclone;

Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallyipropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;

Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;

Bromides such as Ammonium Bromide, Calcium Bromide, Calcium Bromolactobionate, Lithium Bromide, Magnesium Bromide, Potassium Bromide and Sodium Bromide;

Carbamates such as Amyl Carbamate—Tertiary, Ethinamate, Hexaprpymate, Meparfynol Carbamate, Novonal and Tricholorourethan;

Chloral derivatives such as Carbocloral, Chloral Betaine, Chloral Formamide, Chloral Hydrate, Chloralantipyrine, Dichloralphenazone, Pentaerythritol Chloral and Triclofos;

Piperidinediones such as Glutehimide, Methyprylon, Piperidione, Pyrithyldione, Taglutimide and Thalidomide;

Quinazolone derivatives such as Etaqualone, Mecloqualone and Methaqualone; and others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane;

Thrombolytic agents such as APSAC, Plasmin, Pro-Urokinase, Streptokinase, Tissue Plasminogen Activator and Urokinase;

Thyrotropic hormones such as TRH and TSH;

Uricosurics such as Benzbromarone, Ethebenecid, Orotic Acid, Oxycinchophen, Probenecid, Sulfinpyrazone, Ticrynafen and Zoxazolamine;

Vasodilators (cerebral) such as Bencyclane, Cinnarizine, Citicoline, Cyclandelate, Ciclonicate, Diisopropylamine Dichloractetate, Eburnamorine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil;

Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, proprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexyline, Pimethylline, Prenylamine, Propatyl Nitrate, Pyridofylline, Trapidil, Tricromyl, Trimetazidine, TroInitrate Phosphate and Visnadine;

Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, lsoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate;

Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin;

Vitamins, vitamin sources, and vitamin extracts such as Vitamins A, B, C, D, E, and K and derivatives thereof, Calciferols, Glycyrrhiza and Mecobalamin;

Vulnerary agents such as Acetylcysteine, Allantoin, Asiaticoside, Cadexomer Iodine, Chitin, Dextranomer and Oxaceprol;

Anticoagulants such as heparin;

Miscellaneous such as Erythropoietin (Hematinic), Filgrastim, Finasteride (Benign Prostate Hypertrophy) and Interferon β 1-α (Multiple Sclerosis).

In certain embodiments, the agent to be delivered is one or more proteins, hormones, vitamins or minerals. In certain embodiments, the agent to be delivered is selected from insulin, IGF-1, testosterone, vinpocetin, hexarelin, GHRP-6 or calcium. In certain embodiments, the compositions contain two or more agents.

The above list of active agents is based upon those categories and species of drugs set forth on pages THER-1 to THER-28 of The Merck Index, 12th Edition, Merck & Co. Rahway, N.J. (1996). This reference is incorporated by reference herein in its entirety.

D. Uses of the Compositions

Therapeutic and diagnostic applications of the microspheres include drug delivery, vaccination, gene therapy, and in vivo tissue or tumor imaging. Routes of administration include oral or parenteral administration; mucosal administration; ophthalmic administration; intravenous, subcutaneous, intra articular, or intramuscular injection; inhalation administration; and topical administration.

The diseases and disorders can include, but are not limited to neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The microparticles provided herein can be used to treat Infectious diseases, such as arboviral infections, botulism, brucellosis, candidiasis, campylobacteriosis, chickenpox, chlamydia, cholera, coronovirus infections, *staphylococcus* infections, coxsackie virus infections, Creutzfeldt-Jakob disease, cryptosporidiosis, cyclospora infection, cytomegalovirus infections, Epstein-Barr virus infection, dengue fever, diphtheria, ear infections, encephalitis, influenza virus infections, parainfluenza virus infections giardiasis, gonorrhea, *Haemophilus influenzae* infections, hantavirus infections, viral hepatitis, herpes simplex virus infections, HIV/AIDS, *helicobacter* infection, human papillomavirus (HPV) infections, infectious mononucleosis, legionellosis, leprosy, leptospirosis, listeriosis, lyme disease, lymphocytic choriomeningitis, malaria, measles, marburg hemorrhagic fever, meningitis, monkeypox, mumps, mycobacteria infection, mycoplasma infection, norwalk virus infection, pertussis, pinworm infection, pneumococcal disease, *Streptococcus pneumonia* infection, *Mycoplasma pneumoniae* infection, *Moraxella catarrhalis* infection, *Pseudomonas aeruginosa* infection, rotavirus infection, psittacosis, rabies, respiratory syncytial virus infection (RSV), ringworm, rocky mountain spotted fever, rubella, salmonellosis, SARS, scabies, sexually transmitted diseases, shigellosis, shingles, sporotrichosis, streptococcal infections, syphilis, tetanus, trichinosis, tuberculosis, tularemia, typhoid fever, viral meningitis, bacterial meningitis, west nile virus infection, yellow fever, yersiniosis zoonoses, and any other infectious respiratory, pulmonary, dermatological, gastrointestinal and urinary tract diseases.

Other diseases and conditions, including arthritis, asthma, allergic conditions, Alzheimer's disease, cancers, cardiovascular disease, multiple sclerosis (MS), Parkinson's disease, cystic fibrosis (CF), diabetes, non-viral hepatitis, hemophilia, bleeding disorders, blood disorders, genetic disorders, hormonal disorders, kidney disease, liver disease, neurological disorders, metabolic diseases, skin conditions, thyroid disease, osteoporosis, obesity, stroke, anemia, inflammatory diseases and autoimmune diseases.

E. Combinations, Kits, Articles of Manufacture

Combinations and kits containing the combinations provided herein including microparticles or ingredients for forming the microparticles such as a protein or other macromolecule, counterions, solvents, buffers, or salts and optionally including instructions for administration are provided. The combinations include, for example, the compositions as provided herein and reagents or solutions for diluting the compositions to a desired concentration for administration to a host subject, including human beings. The combinations also can include the compositions as provided herein and additional nutritional and/or therapeutic agents, including drugs, as provided herein.

Additionally provided herein are kits containing the above-described Combinations and optionally instructions for administration by oral, subcutaneous, transdermal, intravenous, intramuscular, ophthalmic or other routes, depending on the protein and optional additional agent(s) to be delivered.

The compositions provided herein can be packaged as articles of manufacture containing packaging material, a composition provided herein, and a label that indicates that the composition, e.g., a DAS181 formulation, is formulated for oral, pulmonary or other delivery.

The articles of manufacture provided herein can contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment.

The following examples are included for illustrative purposes only and are not intended to limit the scope of the invention.

EXAMPLE 1

Preparation of Microspheres of the Sialidase Fusion Protein, DAS181

A. Purification of DAS181

DAS181 is a fusion protein containing the heparin (glysosamino glycan, or GAG) binding domain from human amphiregulin fused via its N-terminus to the C-terminus of a catalytic domain of *Actinomyces Viscosus* (sequence of amino acids set forth in SEQ ID NO:17). The DAS181 protein was purified as described in Malakhov et al., *Antimicrob. Agents Chemother.*, 1470-1479, 2006, which is incorporated in its entirety by reference herein. Briefly, the DNA fragment coding for DAS181 was cloned into the plasmid vector pTrc99a (Pharmacia; SEQ ID NO:16) under the control of a IPTG (isopropyl-β-D-thiogalactopyranoside)-inducible promoter. The resulting construct was expressed in the BL21 strain of *Escherichia Coli* (*E. Coli*).

The *E. Coli* cells containing the expressed construct were lysed by sonication in 50 mM phosphate buffer, pH 8.0; 0.3 M NaCl and 10% glycerol. The clarified lysate was passed through an SP-Sepharose column. Proteins were eluted from the column with lysis buffer that contained 0.8 M NaCl. The fraction eluted from SP-Sepharose was adjusted to 1.9 M ammonium sulfate ($(NH_4)_2SO_4$), clarified by centrifugation, and loaded onto a butyl-Sepharose column. The column was washed with two volumes of 1.3 M $(NH_4)_2SO_4$, and the DAS181 fusion protein was eluted with 0.65 M $(NH_4)_2SO_4$.

For the final step, size exclusion chromatography was performed on Sephacryl S-200 equilibrated with phosphate-buffered saline (PBS). The protein purity was determined to be greater than 98% as assessed by sodium dodecyl sulfate-polyacrylamide gel electrophoresis, reversed-phase high-pressure liquid chromatography, and enzyme-linked immunosorbent assay with antibodies generated against *E. Coli* cell proteins. The purified DAS181, molecular weight 44,800 Da, was dialyzed against 2 mM sodium acetate buffer, pH 5.0.

B. Activity of DAS181

The sialidase activity of DAS181 was measured using the fluorogenic substrate 4-methylumbelliferyl-N-acetyl-α-D-neuraminic acid (4-MU-NANA; Sigma). One unit of sialidase is defined as the amount of enzyme that releases 10 nmol of MU from 4-MU-NANA in 10 minutes at 37° C. (50 mM $CH_3COOH$—NaOH buffer, pH 5.5) in a reaction that contains 20 nmol of 4-MU-NANA in a 0.2 ml volume (Potier et al., *Anal. Biochem.*, 94:287-296, 1979). The specific activity of DAS181 was determined to be 1,300 U/mg protein (0.77 μg DAS181 protein per unit of activity).

C. Preparation of Microspheres Using Purified DAS181

DAS181 (10 mg/ml), purified and prepared as described under Section A above, was used to form 200 μl cocktails as shown below. The cocktails contained either glycine or citrate as counterions, and isopropanol as organic solvent, as follows:

1) DAS181+5 mM glycine, pH 5.0;
2) DAS181+5 mM glycine, pH 5.0+10% isopropanol;
3) DAS181+5 mM sodium citrate, pH 5.0;
4) DAS181+5 mM sodium citrate, pH 5.0+10% isopropanol;

Plastic microcentrifuge tubes containing the cocktails with ingredients as described in 1)-4) above were gradually cooled from:

(a) ambient temperature (about 25° C.) to 4° C. by placing the cocktails in a refrigerator, followed by:
(b) cooling to −20° C. by placing the resulting cocktail from (a) in a freezer, followed by:
(c) freezing to −80° C. by placing the resulting cocktail from b) in a freezer.

Under optimal conditions, microspheres would be expected to form between about 4° C. to about −20° C. (generally in the range of about −2° C. to about −15° C.). Freezing to −80° C. is carried out to remove ingredients from the cocktail other than the microspheres (e.g., solvent, etc.) by freeze-drying. Cocktail 4) was prepared in triplicate, two aliquots in plastic tubes and one in a glass tube. One aliquot (in a plastic tube) was cooled as described above, while the two other aliquots (one in a plastic tube and one in a glass tube) were subjected to snap cooling/freezing by dipping the tubes into liquid nitrogen.

Upon freezing, all tubes were placed into the lyophilizer and the volatiles (water and isopropanol) were removed by sublimation, leaving the dry pellets.

Results:

The dry pellets recovered from the cocktails treated as described above, were tested for the presence of microspheres. Of the above samples, microspheres with good dispersivity characteristics, about 2 microns (µm) in size, were observed only with cocktail 4) containing citrate counterion and isopropanol and subjected to gradual cooling. The counterion glycine did not prove to be optimal for the DAS181 protein (cocktail 2)), showing a mixture of glass-like crystals and agglomerates with only a few microspheres. When no organic solvent was present, a glass-like mass of lyophilized DAS181 protein was obtained and no microspheres were observed (cocktails 1) and 3)). Snap-freezing of cocktail 4) in a glass tube produced glass-like crystals and no microspheres, while snap-freezing of cocktail 4) in a plastic tube (cooling rate is slightly slower due to slower diffusion of heat through plastic than through glass) produced agglomerated microspheres.

This example demonstrates that microspheres with narrow size distribution and good dispersivity (minimal agglomeration) can be produced by a combination of appropriate protein, counterion, organic solvent and gradual cooling, using the methods provided herein.

EXAMPLE 2

Size of DAS181 Microspheres as a Function of Organic Solvent Concentration

DAS181 was purified and used to prepare microspheres as described above in Example 1 (see cocktail 4)), using a combination of DAS181 protein (10 mg/ml), citrate counterion (sodium citrate, 5 mM) and isopropanol organic solvent (10%, 20% or 30%). The resulting cocktail solutions were cooled from ambient temperature (about 25° C.) to 4° C., followed by cooling to −20° C., followed by freezing to −80° C., as described in Example 1. Upon freezing to −80° C., the tubes are placed in a lyophilizer and the volatiles (water and isopropanol) were removed by sublimation, leaving the dry powder containing microspheres.

Results:

Microsphere formation was observed with all three concentrations: 10%, 20%, or 30%, of the organic solvent isopropanol. The dimensions of the microspheres however varied, depending on the concentration of the organic solvent. The sizes of the microspheres as determined by comparing the particles to a grid on a hemocytometer were estimated to be 2 microns using 10% isopropanol, 4 microns using 20% isopropanol, and 5-6 microns using 30% isopropanol. These results demonstrate that the size of the microparticles can be engineered as desired using an appropriate concentration of organic solvent.

EXAMPLE 3

Size of DAS181 Microspheres as a Function of Protein Concentration

DAS181 was purified and used to prepare microspheres as described above in Example 1 (see cocktail 4)), using a combination of DAS181 protein (5 mg/ml or 10 mg/ml), citrate counterion (sodium citrate, 5 mM) and isopropanol (5% or 20%). The resulting cocktail solutions were cooled from ambient temperature (about 25° C.) to 4° C., followed by cooling to −20° C., followed by freezing to −80° C., as described in Example 1. Upon freezing to −80° C., the tubes were placed in a lyophilizer and the volatiles (water and isopropanol) were removed by sublimation, leaving the dry powder containing microspheres.

Results:

Microsphere formation was observed with both concentrations of protein (5 mg/ml and 10 mg/ml), and both concentrations of organic solvent (5% or 20%). The dimensions of the microspheres however varied. Cocktails containing 5 mg/ml or 10 mg/ml protein and 5% isopropanol produced microspheres estimated to be about 1.5 micron in size. The cocktail containing 5 mg/ml protein and 20% isopropanol produced microspheres of an estimated size of about 3 microns, while the cocktail containing 10 mg/ml protein and 20% isopropanol produced microspheres of an estimated size of about 4 microns. These results demonstrate that the size of the microparticles can be engineered as desired using an appropriate concentration of protein, or an appropriate combination of concentration of organic solvent and concentration of protein.

EXAMPLE 4

Size of DAS181 Microspheres as a Function of Counterion Concentration

DAS181 was purified and used to prepare microspheres as described above in Example 1 (see cocktail 4)), using a combination of DAS181 protein (10 mg/ml), citrate counterion (sodium citrate; 2 mM, 3 mM or 6 mM) and isopropanol (20%). The cocktail solutions were mixed in glass vials and cooled from +20° C. to −40° C. at a freeze ramp of 1° C. per minute in a Millrock Lab Series lyophilizer. Volatiles (water and isopropanol) were removed by sublimation at 100 mTorr with primary drying at −30° C. for 12 hours and secondary drying at 30° C. for 3 hours, leaving the dry powder containing microspheres.

Results:

Microsphere formation was observed at all three tested concentrations of citrate counterion. The size of the microspheres increased from 1 micron at 2 mM citrate, to 3 microns at 3 mM citrate, to 5 microns at 6 mM citrate. Addition of 1 mM sodium acetate or 1 mM sodium chloride to the cocktail containing 2 mM citrate did not affect formation of the microspheres triggered by the citrate counterion. These results demonstrate that the size of the microparticles can be engineered as desired using an appropriate concentration of counterion.

EXAMPLE 5

DAS181 Microspheres Formed in the Presence of Surfactants

The addition of surfactants to macromolecular (e.g., protein) microspheres often can improve characteristics of the microspheres that render them suitable for administration to a subject, such as flowability, dispersivity and disposition for a particular route of administration, such as intranasal or oral inhalation. To test whether surfactants can be incorporated into the methods of manufacturing microspheres as provided herein, the production of DAS181 microspheres was undertaken as described in Example 1 above, except that in addition, a surfactant was added to the solution.

To a cocktail solution containing 5 mg/ml DAS181, 5 mM sodium citrate, and 20% isopropanol, was added a surfactant (3.5% w/w lecithin, 0.7% w/w Span-85® (sorbitan trioleate), or 3.5% w/w oleic acid). The microspheres were formed by cooling the solutions to 4° C., followed by cooling to −20° C., followed by freezing to −80° C. for lyophilization as described above in Example 1. Upon freezing, the tubes were placed into a lyophilizer and the volatiles (water and isopropanol) were removed by sublimation, leaving the dry powder containing microspheres.

Results:

The microspheres resulting from treatment of each of the above cocktails as described above were spread on glass slides using cover slips rubbed in a circular motion. Efficient microsphere formation was observed in all cases. When the samples containing surfactant were compared to the sample containing all the remaining ingredients but no added surfactant, it was noted that the microspheres formed in the presence of surfactant had improved dispersivity (lesser agglomeration or aggregation).

EXAMPLE 6

Preparation of Microspheres of Bovine Serum Albumin (BSA) by Selection of Suitable Types and Concentrations of Organic Solvents and Counterions As described herein, the methods provided herein can empirically be optimized in high-throughput format to obtain microspheres having desired characteristics including size, flowability and dispersivity. The purpose of this experiment was to demonstrate that by varying types and concentrations of organic solvents and counterions, as well as pH of the cocktail, size and quality of microspheres of a protein of interest, in this case bovine serum albumin (BSA), can be adjusted.

Cocktail solutions containing 5 mg/ml of BSA and various organic solvents and counterions at indicated pH and concentrations (see Table 1) were placed in a microtiter plate (final volume per well of 0.1 ml). Cocktails were cooled from +20° C. to −40° C. at a freeze ramp of 1° C. per minute in a Millrock Lab Series lyophilizer. Volatiles were removed by sublimation at 100 mTorr, with a primary drying at −30° C. for 12 hours and secondary drying at 30° C. for 3 hours.

Results:

The results are shown in Table 1 below. For the BSA protein, combinations (of counterion and organic solvent, respectively) that produced the most uniform microspheres with minimal crystallization or aggregation include:
(1) citrate+isopropanol
(2) citrate+acetone
(3) itaconic acid+1-propanol
(4) glycine+dioxane
(5) glycine+1-propanol
(6) rubidium+1-propanol
(7) perchlorate+1-propanol

TABLE 1

High-throughput screening of BSA microspheres formed under different conditions

| Counterion | pH | Organic Solvent | Product description |
| --- | --- | --- | --- |
| 5 mM pivalic acid | 4.0 | 5% Cyclohexanol | 0.5-1 micron microspheres with occasional crystals |
| 5 mM pivalic acid | 4.0 | 5% 1-propanol | 0.5-1 micron microspheres with some aggregates |
| 5 mM pivalic acid | 4.0 | 5% butyl alcohol | Aggregated microspheres |
| 5 mM pivalic acid | 4.0 | 5% p-Dioxane | Aggregated microspheres |
| 5 mM rubidium chloride | 9.0 | 5% Cyclohexanol | 0.5-1 micron microspheres. Aggregates and occasional crystals |
| 5 mM rubidium chloride | 9.0 | 5% 1-propanol | 0.5-1 micron microspheres |
| 5 mM rubidium chloride | 9.0 | 5% butyl alcohol | Few microspheres (0.5-1 micron). Mostly aggregates and crystals |
| 5 mM rubidium chloride | 9.0 | 5% p-Dioxane | 1-2 microns microspheres with some aggregates |
| 5 mM sodium bromide | 4.0 | 5% Cyclohexanol | 1-2 microns microspheres with some aggregates |
| 5 mM sodium bromide | 4.0 | 5% 1-propanol | Few microspheres (0.5-2 micron). Mostly aggregates and crystals |
| 5 mM sodium bromide | 4.0 | 5% butyl alcohol | Few microspheres (0.5-1 micron). Mostly aggregates and crystals |
| 5 mM sodium bromide | 4.0 | 5% p-Dioxane | 1-2 microns microspheres with some aggregates |
| 5 mM sodium perchlorate | 4.0 | 5% Cyclohexanol | 0.5-2 microns microspheres with some crystals and aggregates |
| 5 mM sodium perchlorate | 4.0 | 5% 1-propanol | 0.5-1 micron microspheres |
| 5 mM sodium perchlorate | 4.0 | 5% butyl alcohol | Few 1-2 microns microspheres. Mostly crystals and aggregates |
| 5 mM sodium perchlorate | 4.0 | 5% p-Dioxane | Aggregated microspheres |
| 5 mM calcium phosphate | 4.0 | 5% Cyclohexanol | Few 1-2 microns microspheres, mostly aggregates |
| 5 mM calcium phosphate | 4.0 | 5% 1-propanol | 1-2 microns microspheres with some aggregates |
| 5 mM calcium phosphate | 4.0 | 5% butyl alcohol | Few 1-2 micron microspheres. Mostly crystals and aggregates |
| 5 mM calcium phosphate | 4.0 | 5% p-Dioxane | Aggregated microspheres |
| 5 mM triethylamine | 9.0 | 5% Cyclohexanol | 0.5-1 micron microspheres with some crystals and aggregates |
| 5 mM triethylamine | 9.0 | 5% 1-propanol | 1-2 micron microspheres with some aggregates |
| 5 mM triethylamine | 9.0 | 5% butyl alcohol | Few 1-2 micron microspheres. Mostly crystals and aggregates |
| 5 mM triethylamine | 9.0 | 5% p-Dioxane | Aggregated microspheres |
| 5 mM glycine | 9.0 | 5% Cyclohexanol | 0.5-1 micron microspheres with some crystals and aggregates |
| 5 mM glycine | 9.0 | 5% 1-propanol | 0.5-2 micron microspheres with occasional aggregates |
| 5 mM glycine | 9.0 | 5% butyl alcohol | Few 1-2 micron microspheres. Mostly crystals and aggregates |
| 5 mM glycine | 9.0 | 5% p-Dioxane | 1-2 micron microspheres |
| 5 mM sodium citrate | 4.0 | 15% isopropanol | 1-2 micron microspheres |
| 5 mM sodium citrate | 4.0 | 15% acetone | 0.5-1 micron microspheres |
| 5 mM itaconic acid | 4.0 | 15% 1-propanol | 1-2 micron microspheres |

These results demonstrate that, for each protein, multiple formulations can readily be screened for the best microsphere formation (desired dimensions, uniformity, dispersivity, minimal aggregation and crystal formation, etc.) in high-throughput format. The combinations of reagents and conditions (counterion, organic solvent, pH, concentrations) selected from the initial screen can then further be fine-tuned as desired.

EXAMPLE 7

Preparation of Microspheres Using a Variety of Proteins

The methods provided herein can be used to prepare microspheres using a variety of proteins. In addition to DAS181 and BSA exemplified above, the methods were used to prepare microspheres from trypsin, hemoglobin, DNase I, lysozyme, ovalbumin, RNAse A, hexahistidine-tagged human proteinase inhibitor 8 (PI8, having the sequence of amino acids set forth in SEQ ID NO:15), red fluorescent protein (RFP) and green fluorescent protein (GFP).

DNase I, trypsin and hemoglobin were purchased from Worthington. Lysozyme, ovalbumin, and RNAse A were purchased from Sigma. Purification of 6×His tagged PI8, GFP and RFP: 6×His tagged PI8, GFP and RFP were expressed and purified essentially as described for DAS181 in Example 1 above, with the following modifications:

Purification of 6xHis Tagged GFP and 6xHis Tagged RFP:

Constructs encoding Red Fluorescent protein and Green Fluorescent protein with N-terminal $His_6$ tags were expressed in *E. Coli* as 6×His-tagged proteins. Expression of Red Fluorescent protein was allowed to proceed overnight in LB medium with 1 mM IPTG. Green Fluorescent protein was induced for 3 hour in TB medium with 1 mM IPTG. Cell lysates from 4 liters of induced cultures were clarified by centrifugation and the proteins were purified by metal chelate affinity chromatography on Fast-Flow Chelating resin (GE Healthcare) charged with Nickel and packed into C-10 columns (GE Healthcare).

The proteins were further purified by Gel Filtration Chromatography on a 0.5 cm×70 cm Sephacryl 200 column equilibrated with phosphate buffered saline. The proteins were dialyzed against 2 mM sodium acetate buffer, pH 5.0, and concentrated on a Centriprep (Amicon).

Purification of 6xHis Tagged PI8:

A construct encoding PI8 with an N-terminal $His_6$ tag was expressed in *E. Coli* as 6×His-tagged PI8. Purification was performed as described for 6×His RFP and 6×His GFP above, with the exception that all buffers used in the various chromatographic purification steps contained 1 mM TCEP (Tris (2-carboxyethyl)phosphine hydrochloride).

Preparation of Microspheres:

Cocktail solutions containing 5 mg/ml of protein and various counterions, organic solvents and pH as listed below were prepared in a microtiter plate as described above in Example 6.

TABLE 2

Combinations Used to Produce Microspheres of Different Proteins

| Protein | Counterion | pH | Organic Solvent | Microsphere Size (microns) |
|---|---|---|---|---|
| Trypsin | 5 mM arginine | 8.0 | 5% isopropanol | 0.5-1 |
| Lysozyme | 5 mM citrate | 8.0 | 5% isopropanol | 4-5 |
| PIN 168 (PI8) | 5 mM citrate | 5.0 | 7% isopropanol | 2-5 |
| DNase I | 5 mM citrate | 4.0 | 5% isopropanol | 0.4-1 |
| RNase A | 5 mM citrate | 4.0 | 5% isopropanol | 0.4-1 |
| Hemoglobin | 5 mM glycine | 5.0 | 10% isopropanol | 0.4-0.7 |
| Ovalbumin | 5 mM pivalic acid | 4.0 | 10% isopropanol | 0.5-1 |
| Red fluorescent protein | 5 mM pivalic acid | 7.0 | 10% 1-propanol | 1-4 (occasional aggregates) |
| Green fluorescent protein | 5 mM pivalic acid | 7.0 | 10% 1-propanol | 0.5-1.5 |

The microtiter plate was cooled from +20° C. to −40° C. at a freeze ramp of 1° C. per minute in a Millrock Lab Series lyophilizer. Volatiles (water and isopropanol) were removed by sublimation at 100 mTorr with primary drying at −30° C. for 12 hours and secondary drying at 30° C. for 3 hours, leaving the dry powder containing microspheres.

The dry powders were spread on glass slides and microphotography was performed through either 32× or 100× objective. All the combinations listed in Table 2 above produced microspheres of good quality (uniform size distribution, dispersivity, with few aggregates and/or crystals). The microspheres varied in size from about 0.4-1 micron (RNAse A, DNAse I) to about 2-5 microns (6×His PI8, lysozyme), depending on the protein. This example demonstrates that the methods provided herein can be used to produce microspheres from a wide variety of proteins.

EXAMPLE 8

Aerodynamic Particle Size Distribution of DAS181 Microspheres for Inhalation: A Comparison of the Method Provided Herein with Spray-Drying As described herein, the methods provided herein can be used to produce microspheres in any desired size range, including a range of about 0.5 micron to about 6-8 microns for delivery via inhalation.

A. Preparation of Microspheres

To test the aerodynamic particle size distribution of DAS181 dry powder (microspheres) formulated for delivery by inhalation, DAS181 microspheres were prepared using two methods as follows:

(a) A DAS181 aqueous solution containing 14 mg/ml DAS181, 5 mM sodium citrate, pH 5.0 was spray dried into an air stream at 55° C., to produce microspheres.

(b) Alternately, DAS181 microspheres were produced according to the methods provided herein. To a DAS181 aqueous solution containing 14 mg/ml DAS181, 5 mM sodium citrate, pH 5.0, was added 5% isopropanol as organic solvent. The resulting solution was cooled from +20° C. to −40° C. at a freeze ramp of 1° C. per minute in a Millrock Lab Series lyophilizer. Volatiles (water and isopropanol) were removed by sublimation at 100 mTorr with primary drying at −30° C. for 12 hours and secondary drying at 30° C. for 3 hours, leaving the dry powder containing microspheres.

B. Aerodynamic Particle Size Distribution of Microspheres

The microspheres prepared as described in Example 8A were tested by Andersen Cascade Impaction. The deposition of pharmaceuticals in the respiratory tract can be predicted by the aerodynamic behavior of particles (microspheres) on the stages/collection plates of the cascade impactor.

The cascade impaction experiment was performed using DAS181 microspheres prepared by one of the two alternate methods described in section A above, i.e., either by spray-drying or by the methods provided herein. The microspheres (10 mg) were loaded into gelatin capsules. The gelatin capsules were placed into a CycloHaler (PharmaChemie) dry powder inhaler and subjected to cascade impaction. An 8-stage, non-viable Andersen Cascade Impactor (Thermo Electron, Boston) modified for use at 90 liters per minute of air flow and equipped with a USP throat, induction cone and no preseparator, was used. The collection plates of the impactor representing various areas/stages of deposition post-inhalation (trachea, primary and secondary bronchi, terminal bronchi, alveoli, etc.) were coated with silicon spray to prevent bouncing of the microspheres. The microspheres from the stages and collection plates were recovered into a phosphate buffered saline containing 0.1% Tween, and the amount of deposited DAS181 recovered from each stage and collection plate was quantified by measuring absorbance at 280 nm.

Results:

The geometric size of microspheres produced by the two methods was assessed by light microscopy and found to be essentially identical (range of 1.5-3.0 microns) for both methods. As shown in Table 3 below, however, the aerodynamic particle size distribution of the two preparations differs significantly between the two methods. For the microspheres produced according to a method as provided herein (i.e., method (b) as set forth in section A above), less than 25% remained trapped in the mouth (throat/cone of the impactor assembly), while greater than 70% of the microspheres were delivered to the trachea and lungs (with greater than 40% in the terminal bronchi and alveoli). In comparison, less than 50% of the DAS181 microspheres formed by spray-drying (method (a) as set forth in section A above) was delivered to the trachea and lungs (less than 20% in the terminal bronchi and alveoli). The results demonstrate that methods provided herein can produce microspheres for delivery into deep lungs, and that the microspheres produced by methods provided herein have superior disagglomeration and flowability properties (provide a higher delivered dose) compared to microspheres produced by a spray-drying method.

TABLE 3

Results of Cascade Impaction Analyses of DAS181 Microspheres

| Component of the Andersen Cascade Impactor | Corresponding Size Cut-Off (microns) | Expected Deposition in Respiratory Airways | Percent Deposition of DAS181 | |
|---|---|---|---|---|
| | | | Microspheres Produced by Method (a) (i.e., Spray Drying) | Microspheres Produced by Method (b) |
| Throat + Cone | >10 | oral cavity | 42.9 | 16.6 |
| −2 (S + P) | 8.0-10 | oral cavity | 3.7 | 4.9 |
| −1 (S + P) | 6.5-8.0 | oropharynx | 5.9 | 5.5 |
| −0 | 5.2-6.5 | pharynx | 5.8 | 4.0 |
| 1 | 3.5-5.2 | trachea/bronchi | 12.5 | 9.3 |
| 2 | 2.6-3.5 | secondary bronchi | 11.6 | 12.6 |
| 3 | 1.7-2.6 | terminal bronchi | 11.0 | 24.0 |
| 4 | 1.0-1.7 | alveoli | 4.5 | 19.2 |
| 5 | 0.43-1.0 | Alveoli | 1.4 | 3.5 |

EXAMPLE 9

Large Scale Manufacture of Microspheres

This example demonstrates that the methods provided herein can be scaled for the manufacture of large quantities of DAS181. The Batch Process described herein is suitable for the manufacture of high quality dry powder microspheres in an amount ranging from, for example, milligrams to about a kilogram and is limited by the capacity of the mixing tank and/or lyophilizer shelf space. An alternative "continuous" process described herein can be used to manufacture amounts ranging from, for example, hundreds of grams to hundred or more kilograms (100 grams to 100 kg and above). Additional advantage of continuous process is a better control over the chilling of the cocktail.

The large scale manufacture by a batch process or by a continuous process can follow, for example, one or more of the steps described below in any combination of steps or specific alternative methods:

Precipitation of protein into microspheres. This step can be performed in a batch mode by placing the cocktail solution containing the desired concentration of protein, organic solvent and counterion in lyophilization tray(s) and placing the tray(s) onto lyophilizer shelves. Alternatively, trays can be chilled and frozen on a chilled platform or other type of equipment (e.g., a freezer) and stored for a period of time frozen and lyophilized later. Alternatively, the microspheres can be formed by precipitation in a vessel with stirring, wherein the vessel is placed onto a cold surface or a cooling coil is immersed into liquid or while the cocktail is being recirculated through a heat exchanger using a peristaltic pump. Alternatively, the microspheres can be formed by precipitation in a continuous mode, by passing the cocktail solution through a heat exchanger(s) once using a peristaltic pump.

Removal of bulk liquid. The suspension of the microspheres can be concentrated using standard centrifugation, continuous flow centrifugation (e.g., CARR ViaFuge Pilot), or filtration (e.g., on glass fiber, sintered glass, polymer filters, hollow fiber cartridges (e.g., those manufactured by GE Healthcare) or tangential flow filtration cassettes (TFF cassettes, such as those manufactured by Millipore or Sartorius)). The removal of bulk liquid (50% or greater) can result in a faster drying cycle and higher efficiency and throughput.

Drying the microspheres. The recovered microspheres formed by any mode, can be dried by conventional lyophilization. Alternatively, the microspheres can be dried under ambient temperature and atmospheric pressure, eliminating the use of lyophilizer.

Results:

DAS181 protein was successfully processed into dry powder (microspheres) by a continuous mode as described herein. Cocktail containing 10 mg/ml DAS181, 20% isopropanol, 2 mM sodium sulfate was passed through 35 SERIES heat exchanger (Exergy, Garden City, N.Y.) coupled with a NESLAB circulating cryostat using a peristaltic pump so that during the passage the cocktail was cooled from about 25° C. to about −12° C. The resulting suspension of microspheres exiting the heat exchanger was pumped into a prechilled lyophilization tray (−40° C.), frozen and lyophilized or, alternatively, pumped directly into liquid nitrogen and then lyophilized. The resulting microspheres, which were analyzed by microscopy and cascade impaction, showed uniform microspheres with minimal aggregation and good dispersivity and were similar in dimensions and aerodynamic particle size distribution to the microspheres produced by batch mode. When the formulated DAS181 cocktail solution was not chilled (not passed through heat exchanger, thus no precipitation of microspheres was induced) and poured directly into liquid nitrogen, no microspheres were observed and, instead, glass-like crystals were observed after lyophilization.

EXAMPLE 10

Batch Mode Process and Formulation of DAS181 Microspheres for Delivery to Upper and Central Respiratory Airways This example describes formulation and a process for manufacture of DAS181 microspheres. The contents of the DAS181 cocktail solution and their relative amounts are shown in Table 4 below.

TABLE 4

Batch Manufacturing Formula for DAS181 Microspheres.

| Ingredient | Amount for one batch[1] | | Final concentration in formulated cocktail | Function |
|---|---|---|---|---|
| | Stock solution concentration | Amount added | | |
| DAS181 protein | 19.55 g/L | 3.306 L, API solution | 12 g/L | Active ingredient |
| Sodium acetate[2] | 1.12 mM | | 0.688 mM | pH buffer |
| Acetic acid[2] | 0.63 mM | | 0.0387 mM | pH buffer |
| Sodium Sulfate | 500 mM | 0.0215 L | 2 mM | Microparticle formation agent (counterion) |
| Isopropanol | 100% v/v | 0.269 L | 5% v/v | Microparticle formation agent |
| Calcium chloride | 500 mM | 0.0028 L | 0.268 mM | Stability enhancing agent |
| Water for irrigation | neat | 1.79 L | NA | Diluent |

[1]Batch size: final volume of formulated cocktail 5.38 L. Theoretical yield 74 g of bulk DAS181 Dry Powder.
[2]Components of the DAS181 protein (API) stock solution.

A. Production of Bulk Drug Substance

The terms Drug Substance, Active Pharmaceutical Ingredient, and API are used interchangeably in this example and refer to the DAS181 protein. Production of DAS181 protein in bulk was conducted as follows. First, bulk amounts of DAS181 were expressed in *E. coli* (BL21 strain) essentially as described in Example 1. The *E. coli* cells expressing the DAS181 protein were washed by diafiltration in a fermentation harvest wash step using Toyopearl buffer 1, UFP-500-E55 hollow fiber cartridge (GE Healthcare) and a Watson-Marlow peristaltic pump.

The recombinant DAS181 protein was then purified in bulk from the cells. The detailed specifications of the components and buffers used in the bulk purification of DAS181 are provided in Tables 5 and 6 below. The harvested and washed cells were lysed in a homogenization step by passing the cells twice through using Niro-Soave Panda cell disruptor. The homogenate thus obtained was clarified by microfiltration using the Toyopearl buffer 1, Hydrosart 0.2 micron TFF cassette and a Watson Marlow pump. The clarified homogenate was then concentrated by allowing the lysate to recirculate without fresh buffer feed. Next, DAS181 protein was captured from the clarified homogenate on a Toyopearl SP-550C resin which was washed in a series of buffers (see Table 5) before the DAS181 protein was eluted from the resin. The sodium chloride concentration of the eluate was adjusted to 1.0 M in a final buffer of 50 mM phosphate at pH 8.0. The DAS181-containing eluate was then passed through a Toyopearl Hexyl-650C resin for further purification using a Toyopearl Buffer 4. The resin eluate containing DAS181 protein was then buffer-exchanged into 5 mM sodium acetate in a diafiltration step (see step 8 in Table 5). The concentrated protein was next passed through a Sartorius Q SingleSep Filter in order to remove DNA in a flow-through mode. Isopropanol was added to the Q SingleSep filtrate to a final concentration of 20% v/v. The DAS181 protein in the buffer was passed through an Amberchrome CG300M resin equilibrated with an Amberchrom buffer (see step 11 in Table 5). The purified bulk DAS181 protein was then buffer-exchanged into formulation buffer and concentrated by diafiltration (see step 12 of Table 5).

TABLE 5

| | | Purification of bulk DAS181 drug substance | |
|---|---|---|---|
| 1 | Purpose | Fermentation Harvest Wash | |
| | Cartridge | GE UFP-500-E55 | Specifications |
| | Activity | Buffer Name | Inlet PSI |
| | Diafiltration | Toyopearl Buffer 1 | 25-35 |
| 2 | Purpose | Homogenization | |
| | Activity | Step | Buffer Name |
| | Equilibration | Equilibration | Harvest Buffer |
| | Homogenization 1st Pass | | Sample Load |
| | Homogenization 2nd Pass | | Sample Load |
| 3 | Purpose | Homogenate Clarification (Diafiltration) | |
| | TFF Cartridge | HydroSart 10K 0.6 m² | Specifications |
| | Activity | Buffer Name | Inlet PSI |
| | Recirculation | Sample Load | 40 |
| | Diafiltration | Toyopearl Buffer 1 | <50 |
| 4 | Purpose | Permeate Concentration | |
| | TFF Cartridge | HydroSart 10K 0.6 m² | Specifications |
| | Activity | Buffer Name | Inlet PSI |
| | Recirculation | Sample Load | NS |
| | Concentration | Sample Load | <50 |

TABLE 5-continued

| | | Purification of bulk DAS181 drug substance | |
|---|---|---|---|
| 5 | Purpose | DAS181 capture performed in bind and elute mode | |
| | Resin | Toyopearl SP-550C | |
| | Activity | Step | Buffer Name |
| | Loading | Sample Load | Clar. Homogenate |
| | Wash | SP Wash 1 | Toyopearl Buffer 1 |
| | | SP Wash 2 | Toyopearl Buffer 2 |
| | | SP Wash 3 | Toyopearl Buffer 3 |
| | | SP Wash 4 | Toyopearl Buffer 2 |
| | | SP Wash 5 | Toyopearl Buffer 1 |
| | Elution | Elution | Toyopearl Buffer 4 |
| 6 | Purpose | Adjust NaCl Concentration | |
| | Method | Add NaCl to 1.0 M | |
| | Final Buffer | 50 mM phosphate, 1.0 M NaCl, pH 8.0 | |
| 7 | Purpose | DAS181 purification in flow-through mode | |
| | Resin | Toyopearl Hexyl-650C | |
| | Activity | Step | Buffer Name |
| | Loading | Sample Load | Cond. Hexyl Load |
| 8 | Purpose | Concentration & Diafiltration | |
| | TFF Cartridge | HydroSart 10K 0.6 m$^2$ | Specifications |
| | Activity | Buffer Name | Recirc. L/min* |
| | Recirculation | Toyopearl Buffer 6 | 15-16 |
| | Concentration | Hexyl Product Pool | 15-16 |
| | Diafiltration | Toyopearl Buffer 6 | 15-16 |
| | Recirculation | Toyopearl Buffer 6 | NS |
| 9 | Purpose | Remove DNA in flow-through mode | |
| | Resin | Sartorius Q SingleSep Filter | |
| | Activity | Step | Buffer Name |
| | Loading | Sample Load | |
| 10 | Purpose | Buffer Adjustment | |
| | Method | Add Isopropanol to 20% | |
| | Final Buffer | 5 mM Acetate, 20% Isopropanol, pH 5.0 | |
| 11 | Purpose | DAS181 polishing in flow-through mode | |
| | Resin | Amberchrome CG300M | |
| | Activity | Step | Buffer Name |
| | Loading | Sample Load | Amberchrom Load |
| 12 | Purpose | Concentration & Diafiltration | |
| | TFF Cartridge | HydroSart 10K 0.6 m2 | Specifications |
| | Activity | Buffer Name | Recirc. L/min* |
| | Recirculation | Formulation Buffer | 15-16 |
| | Concentration | Amberchrom Product Pool | 15-16 |
| | Diafiltration | Formulation Buffer | 15-16 |

*Volumes in liters, except 4x denotes multiples of the retentate volume
CV = Column Volumes
NR = Not Recorded
NS = Not Specified

TABLE 6

Buffers used during the DAS181 purification process

| Buffer Name | Buffer Composition |
| --- | --- |
| Toyopearl Buffer 1 | 50 mM potassium phosphate, 0.3 M NaCl, pH 8.0 |
| Toyopearl Buffer 2 | 1.1 mM potassium phosphate, 2.9 mM sodium phosphate, 154 mM NaCl, pH 7.4 |
| Toyopearl Buffer 3 | 1.1 mM potassium phosphate, 2.9 mM sodium phosphate, 154 mM NaCl, 1% Triton X-100, 0.1% SDS, 0.5% sodium deoxycholate, pH 7.4 |
| Toyopearl Buffer 4 | 50 mM potassium phosphate, 1.0 M NaCl, pH 8.0 |
| Toyopearl Buffer 5 | 50 mM potassium phosphate, 0.5 M NaCl, pH 8.0 |
| Toyopearl Buffer 6 | 5 mM sodium acetate, pH 5.0 |
| Toyopearl Buffer 7 | 5 mM sodium acetate, 60% isopropanol, pH 5.0 |
| Formulation Buffer | 1.75 mM sodium acetate, pH 5.0 |
| 3% Isoproyl Alcohol | 3% isopropanol |
| Amberchrom Buffer | 5 mM sodium acetate, 20% isopropanol, pH 5.0 adjusted with acetic acid |
| 1.0 N NaOH 3% Isopropanol | 1.0 N NaOH, 3% isopropanol |
| 1.0 N NaOH | 1.0 N NaOH |
| 0.5 N NaOH | 0.5 N NaOH |
| 0.1 N NaOH | 0.1 N NaOH |
| 70% Isopropyl Alcohol | 70% isopropanol |
| 20% EtOH | 20% ethyl alcohol |

B. Batch Manufacturing Process

The ingredients set forth in Table 4 above were combined to form DAS181 microspheres in a large scale batch process as described below.

Step I: Thawing of Bulk Drug Substance

Frozen 0.2 μm-filtered bulk Drug Substance in plastic bottles was thawed overnight at ambient temperature (25±3° C.).

Step II: Weighing of the Excipients and Preparation of Solutions 35.51 g of Sodium Sulfate anhydrous powder was weighed and Q.S. to 500 mL with Water For Irrigation, then stirred to obtain a clear solution. 18.38 g of Calcium Chloride dihydrate powder was weighed and Q.S. to 250 mL with Water For Irrigation, then stirred to obtain a clear solution.

Step III: Preparation of the DAS181 Cocktail Solution

To 3.3 L of concentrated Drug Substance (19.55 g/L), 1.79 L of Water For Irrigation was added slowly with stirring, followed by 0.0215 L of Sodium Sulfate solution, 0.0028 L of Calcium Chloride solution and 0.269 L of isopropanol. The solution was stirred to ensure complete mixing of components.

Step IV: Filtration of Formulated Cocktail Solution Through 0.2 μm Filter

The formulated cocktail solution of Step III was filtered through a 0.2 μm filter into sterile media bags to control particulates and bioburden.

Step V: Filling into Lyophilization Trays

The formulated filtered solution was dispensed into autoclaved Lyoguard lyophilization trays. To ensure even cooling of the solution and formation of high quality microspheres, 6 trays were each filled with 0.9 L or less of cocktail solution.

Step VI: Freezing and Lyophilization

The trays were placed onto lyophilizer (Hull 120FSX200) shelves prechilled to −45±5° C. and the solution was allowed to chill and freeze. Formation of microspheres occurred while the solution was being frozen. The freezing is allowed to proceed for 1-2 h to ensure complete solidification. The product temperature was verified by reading the thermocouples attached to two of the six trays.

The lyophilization cycle steps are as follows:
a) Set vacuum to 160 microns and allow to evacuate to 100-200 microns;
b) Ramp shelf temperature to +10° C. over 3 h;
c) Hold shelf temperature at +10° C. for 36 h (primary drying);
d) Thermocouple traces examined to verify that primary drying phase is completed and the product temperature has stabilized at +10° C.±5° C. for 15-30 h.
e) Ramp shelf temperature to +30° C. over 1 h and hold for 3-5 h (secondary drying).

Step VII: Transfer of Bulk DAS181 Microspheres into Container and Mixing

A section on the bottom film of each Lyoguard lyophilization tray was cleaned using sanitizing wipes and a 3×3 cm opening was made with a scalpel. The dry microspheres were transferred into a plastic bottle. The bottle was capped and tumbled forty times, changing directions with each inversion. The tumbling was to ensure uniformity of bottle content. Samples for analytical testing were taken and the bottle was recapped and sealed into plastic bags for storage.

In the DAS181 microsphere bulk manufacturing process as described above, sulfate was demonstrated to be a safe substance for use as a counterion, and reproducibly produced microspheres with a narrow size distribution. Further, the organic solvent isopropanol was a good solvent of choice because (1) a class 3 solvent, (2) it can produce microspheres in a wide range (2-30%, v/v) of concentrations, and (3) it has a relatively high freezing point so its vapors can efficiently be trapped during lyophilization.

The protein concentration in the final formulation could be varied (10-14 mg/ml), as could the concentration of counterion (1-5 mM) and isopropanol (2-30% v/v), without substantial impact on the physical properties of the microspheres or the activity of the DAS181 protein in the microspheres. At higher concentrations of isopropanol (15-30%), the microspheres formed while the cocktail was still fully liquid. At lower concentrations (2-15%), ice crystals began to form first, followed by precipitation to form microspheres.

C. Yield of DAS181 in the Microspheres

The theoretical yield of DAS181 in the dry microspheres is calculated according to the following formula:

Theoretical yield=DAS181 protein, g÷protein fraction in Dry Powder (microspheres)

The protein fraction value (0.866) was established empirically by analysis of several manufactured batches of DAS181 microspheres. The theoretical yield for the amounts as set forth in Table 2 is 64.56 g÷0.866=74.55 g. The actual yield of DAS181 Dry Powder was found to be 64 g.

Results:

The suitability of the microspheres prepared as described in section B above for administration by oral inhalation was tested by Andersen Cascade Impaction. The results are summarized in Table 7 below. The deposition of pharmaceuticals in the respiratory tract can be predicted by deposition of particles (microspheres) on the stages/collection plates of the cascade impactor. For a pharmaceutical, e.g., DAS181 microspheres, that is administered to prevent or treat viral infections that initiate in the respiratory tract, such as influenza, it is desirable to deposit the pharmaceutical in the throat, trachea, bronchi (upper and central respiratory airways). The DAS181 fusion protein delivered to upper and central respiratory airways cleaves off the receptor sialic acids from mucous membranes, thus preventing viral binding and infection at these sites. For optimal delivery of the DAS181 microspheres to sites where respiratory viral infection can be initiated, i.e., in the throat, trachea or bronchi, the microspheres must not be (a) so big that they are trapped at the front end in the mouth (i.e., microspheres are too big, about 8 microns or greater); or (b) so small that they are deposited in deep lungs and absorbed systemically into the blood stream (i.e., 0.5 microns or smaller). For delivery of the DAS181 microspheres to the throat, trachea and bronchi, a size range of about 1 micron to about 5.5-6 microns generally is suitable.

DAS181 microspheres manufactured as described above were characterized by Andersen cascade impaction and found to be suitable for delivery to upper and central respiratory airways with sufficiently low percentage (<5%) deposited in the alveoli.

TABLE 7

Aerodynamic Particle Size Distribution of DAS181 dry powder at 60 liters per minute.

| Component of Andersen Cascade Impactor | Corresponding size cut-off, microns | Expected deposition in respiratory airways | DAS181 protein deposited in mg | Percent of total DAS181 protein recovered |
|---|---|---|---|---|
| Inhaler (Cyclohaler) | | | 1.57 ± 0.11 | 20.13% |
| Throat/Cone | >10 | Oral cavity | 0.93 ± 0.19 | 11.92% |
| −1 (Stage + Plate) | 8.6-10 | Oral cavity | 0.50 ± 0.10 | 6.41% |
| −0 (Stage + Plate) | 6.5-8.6 | oropharynx | 0.40 ± 0.03 | 5.13% |
| 1 (Stage + Plate) | 4.4-6.5 | pharynx | 0.58 ± 0.03 | 7.44% |
| 2 (Stage + Plate) | 3.3-4.4 | trachea/bronchi | 0.83 ± 0.07 | 10.64% |
| 3 (Stage + Plate) | 2.0-3.3 | Secondary bronchi | 1.80 ± 0.09 | 23.08% |
| 4 (Stage + Plate) | 1.1-2.0 | Terminal bronchi | 0.82 ± 0.08 | 10.51% |
| 5 (Stage + Plate) | 0.54-1.1 | alveoli | 0.23 ± 0.03 | 2.95% |
| 6 (Stage + Plate) | 0.25-0.54 | alveoli | 0.14 ± 0.03 | 1.79% |
| ΣACI (Emitted) | | | 6.24 ± 0.10 | 80.00% |

10 ± 1.0 mg of DAS181 Dry Powder (8.5 mg ± 10% DAS181 protein) was filled into HPMC capsule
ΣACI (Emitted) fraction is the sum of all material recovered from USP Throat, Induction Cone and stages −1 to 6.

DAS181 microspheres were further characterized by laser diffraction, which demonstrated, consistent with the cascade impaction results, that the majority of the microspheres produced by the method described in this Example are within a size range of between 1 micron and 5 microns in size. Scanning Electron Microscopy (FEI Quanta 200 Scanning Electron Microscope, Everhart Thornley (ET) detector) of the DAS181 microspheres prepared according to the method described in this Example revealed that the microspheres are present as agglomerates of hundreds and thousands of individual particles approximately 0.5-3 micron in size. The agglomerates however are easily dissipated by air turbulence produced during the actuation through dry powder inhaler (as demonstrated by Andersen Cascade Impaction or laser diffraction). Light microscopy of microspheres dispersed in a liquid surfactant (e.g. Triton X-100 or Tween 20) or non-polar solvent (e.g., alcohol, acetone, or acetonitrile) that does not dissolve the microspheres, confirmed that aggregates are easily dissipated into individual uniform microspheres.

EXAMPLE 11

Preparation of DAS181 Microspheres Using Sulfates Other than the Sodium Salt

Studies have shown that in certain instances, e.g., in some asthmatics, the presence of sodium in formulations for pulmonary administration could carry a risk of inducing airway hyperresponsiveness (Agrawal et al., Lung, 183:375-387 (2005)). This example therefore tested alternate salts, such as salts of other metals such as potassium, magnesium and calcium.

DAS181 microspheres were manufactured as described above in Example 1. Cocktail solutions containing 12 mg/mL DAS181 and 5% (v/v) isopropanol contained as counterions the indicated sulfates at 2 mM concentration, pH 4.5-5.0. The microspheres were formed by cooling the solutions from +25° C. to −45° C. Upon freezing, the volatiles (water and isopropanol) were removed by sublimation, leaving the dry powder containing microspheres.

The aerodynamic particle size distribution of the dry powder was assessed by Andersen Cascade Impaction, and the amount of DAS181 per stage was determined by UV measurement at 226 nm ($A_{226}$). The results are shown below in Table 8. The results demonstrate that sulfate salts other than the sodium salt can be used as counterion to obtain DAS181 microspheres of a size range such that the majority are delivered to the throat, trachea and bronchi, in an amount that is comparable to the amount delivered when sodium sulfate is used as the counterion.

TABLE 8

Aerodynamic Particle Size Distribution of DAS181 microspheres formulated with or without sodium

| | Corresponding size cut-off, microns | Expected deposition in respiratory airways | Sodium Sulfate | Potassium Sulfate | Magnesium Sulfate | Calcium Sulfate |
|---|---|---|---|---|---|---|
| Inhaler | | | 19.86% | 28.58% | 21.41% | 16.71% |
| Capsule | | | 2.07% | 2.30% | 1.88% | 0.00% |
| Throat + Cone | >10 | Oral cavity | 11.67% | 9.00% | 12.91% | 16.79% |
| −1 (S + P) | 8.6-10 | Oral cavity | 10.00% | 3.43% | 7.86% | 14.87% |
| −0 (S + P) | 6.5-8.6 | oropharynx | 5.30% | 3.08% | 4.71% | 7.77% |
| 1 (S + P) | 4.4-6.5 | pharynx | 6.97% | 5.86% | 6.58% | 7.54% |
| 2 (S + P) | 3.3-4.4 | trachea/bronchi | 7.55% | 8.24% | 6.90% | 6.43% |
| 3 (S + P) | 2.0-3.3 | Secondary bronchi | 19.57% | 20.21% | 17.01% | 12.65% |
| 4 (S + P) | 1.1-2.0 | Terminal bronchi | 12.39% | 14.00% | 13.00% | 10.39% |
| 5 (S + P) | 0.54-1.1 | alveoli | 2.80% | 2.99% | 4.31% | 4.69% |
| 6 (S + P) | 0.25-0.54 | alveoli | 1.82% | 2.31% | 3.44% | 2.16% |

The dry powders also were incubated at +37° C. or +53° C. for a duration as indicated in Table 9 and tested for sialidase activity using the 4-MU-NANA assay as described in Example 1 and incorporated by reference herein. The relative activity compared to non-lyophilized DAS181 microspheres stored at −80° C. is shown in Table 9. The results show that the stability of the microspheres prepared using the various metal sulfates as counterions were comparable to that of sodium sulfate, with retention of almost all or all the activity for over 2 months at 37° C. and retention of almost all (sodium and potassium sulfates) or over 85% (magnesium and zinc sulfates) of the activity for over 10 days at 53° C. This experiment demonstrates that various non-sodium containing counterions can produce microspheres with desirable characteristics.

TABLE 9

Sialidase activity of DAS181 microsphere formulations: accelerated stability studies.

| | Percent Activity Remaining Temperature | | | |
|---|---|---|---|---|
| | 37° C. | | 53° C. | |
| | Incubation Days | | | |
| | 42 Days | 69 Days | 11 Days | 39 Days |
| 2 mM Sodium Sulfate + 0.268 mM CaCl$_2$ | 107.14% | 105.62% | 110.66% | 23.66% |
| 2 mM Potassium Sulfate + 0.268 mM CaCl$_2$ | 97.37% | 104.00% | 101.54% | 52.76% |
| 2 mM Magnesium Sulfate + 0.268 mM CaCl$_2$ | 123.81% | 107.29% | 85.93% | 60.00% |
| 13.34 mM Calcium/2 mM Sulfate | 116.67% | 93.20% | 87.12% | 40.48% |

EXAMPLE 12

Stability of DAS181 Microspheres

The stability of the DAS181 protein in the microspheres was assessed by measuring sialidase activity over time using the 4-MU-NANA activity assay as described above in Example 1 and as incorporated by reference herein. The production of dry DAS181 microspheres was undertaken in a cocktail solution containing 10 mg/mL DAS181, 2 mM sodium sulfate, 5% v/v isopropanol. To some solutions, 0.01% w/v sugar (sorbitol, mannitol, trehalose or sucrose) was added. The microspheres were formed by cooling the solutions from +25° C. to −45° C. Upon freezing, the volatiles (water and isopropanol) were removed by sublimation, leaving the dry powders containing microspheres.

A. Stability of DAS181 Microspheres without Sugars

The DAS181 dry powder microspheres formulated without sugars were stored at room temperature (25° C.) in a container next to Drierite desiccant (Hammond Drierite, Xenia, Ohio). The dry powder retained its original potency (as measured by sialidase activity using 4-MU-NANA according to Example1 and as incorporated by reference herein; results shown in Table 10) and aerodynamic particle size distribution (as measured by Andersen Cascade impaction; Table 11) for at least 8 months.

TABLE 10

Specific activity of DAS181 dry powder.

| Test | Time 0 | 3 months | 8 months |
|---|---|---|---|
| Sialidase Activity with reference to time 0 | 100% | 102.0% | 99.9% |

TABLE 11

Aerodynamic particle size distribution of DAS181 dry powder

| ACI Component | Corresponding size cut-off, microns | Expected deposition in respiratory airways | Time 0 | 3 Months | 8 Months |
|---|---|---|---|---|---|
| Throat + Cone | >10 | Oral cavity | 19.57 ± 2.43 | 26.00 ± 0.30 | 18.57 ± 4.14 |
| Stage −1 | 8.6-10 | Oral cavity | 17.87 ± 0.51 | 12.87 ± 1.56 | 15.13 ± 2.41 |
| Stage −0 | 6.5-8.6 | oropharynx | 10.27 ± 0.93 | 7.07 ± 0.32 | 9.80 ± 1.80 |
| Stage 1 | 4.4-6.5 | pharynx | 8.57 ± 0.49 | 8.80 ± 0.26 | 7.73 ± 0.57 |
| Stage 2 | 3.3-4.4 | trachea/bronchi | 10.67 ± 0.23 | 10.70 ± 0.35 | 9.30 ± 0.82 |
| Stage 3 | 2.0-3.3 | Secondary bronchi | 21.10 ± 0.75 | 21.80 ± 0.52 | 21.90 ± 0.87 |
| Stage 4 | 1.1-2.0 | Terminal bronchi | 10.10 ± 0.75 | 10.63 ± 0.80 | 14.50 ± 3.22 |
| Stage 5 | 0.54-1.1 | alveoli | 1.47 ± 0.23 | 1.73 ± 0.06 | 2.37 ± 0.06 |
| Stage 6 | 0.25-0.54 | alveoli | 0.33 ± 0.06 | 0.40 ± 0.10 | 0.73 ± 0.06 |

Table 11: Aerodynamic particle distribution was assessed by Andersen Cascade Impaction and expressed as % of total DAS181 protein recovered. Capsules were filled with 10 mg of DAS181 dry powder and actuated using Cyclohaler dry powder inhaler as delivery device. Air flow rate was 60 Liters per minute. Assays were performed in triplicate, mean and standard deviation are shown.

B. Stability of DAS181 Microspheres Formulated with Sugars

The sialidase activity of DAS181 in the dry powder microsphere formulations containing sugars and in the unlyophilized microsphere formulations stored at −80° C., were measured using fluorescent substrate 4-MU-NANA as described in Example 1 and as incorporated by reference herein. The dry powder formulations containing no sugar or various sugars as indicated below in Table 12 were stored at +42° C. for 4 weeks (forced degradation). The results are shown in Table 12. Relative to unlyophilized formulations stored at −80° C., the formulation containing no sugar retained almost 80% of its activity. The addition of various sugars increase the stability so that about 88-98% of the activity is retained, depending on the sugar.

TABLE 12

| Sugar | Percent Sialidase Activity Remaining after 4 weeks at 42° C. |
|---|---|
| No Sugar | 79.82 |
| Sorbitol | 91.23 |

TABLE 12-continued

| Sugar | Percent Sialidase Activity Remaining after 4 weeks at 42° C. |
|---|---|
| Mannitol | 89.47 |
| Trehalose | 97.37 |
| Sucrose | 88.60 |

Since modifications will be apparent to those of skill in this art, it is intended that this invention be limited only by the scope of the appended claims.

What is claimed is:

1. A method of making a microparticle composition comprising:
   a) adding a counterion selected from the group consisting of sodium citrate, sodium sulfate, calcium sulfate, potassium sulfate and magnesium sulfate to an aqueous solution comprising a polypeptide comprising SEQ ID NO:17, whereby an aqueous composition is formed;
   b) adding isopropanol to the aqueous composition of (a) whereby a second aqueous composition is formed; and
   c) cooling the second aqueous composition of (b) at a rate of 0.1° C./min to 10° C./min to a temperature between 4° C. and −45° C., whereby a composition containing microparticles comprising a polypeptide compromising SEQ ID NO: 17 is formed.

2. The method of claim 1 wherein the cooling rate is 0.5° C./min to 2° C./min.

3. The method of claim 1 wherein the cooling rate is 0.5° C./min to 1' C/min.

4. The method of claim 1 wherein the counterion is sodium citrate.

5. The method of claim 1 wherein the counterion is magnesium sulfate.

6. The method of claim 1 further comprising cooling the composition containing microparticles comprising a polypeptide compromising SEQ ID NO: 17 to a temperature of between about −45° C. and about −80° C.

7. The method of claim 1 wherein step c) comprises cooling the second aqueous composition of (b) to a temperature between 2° C. and −20° C. degrees.

8. The method of claim 1 wherein step b) comprises adding isopropanol to about 10% v/v.

9. The method of claim 1 wherein step b) comprises adding isopropanol to about 20% v/v.

10. The method of claim 1 wherein step b) comprises adding isopropanol to about 30% v/v.

11. The method of claim 1 further comprising lyophilizing the composition containing microparticles to obtain a dry powder.

* * * * *

UNITED STATES PATENT AND TRADEMARK OFFICE
CERTIFICATE OF CORRECTION

| | | |
|---|---|---|
| PATENT NO. | : 8,623,419 B2 | Page 1 of 1 |
| APPLICATION NO. | : 13/289644 | |
| DATED | : January 7, 2014 | |
| INVENTOR(S) | : Michael P. Malakhov et al. | |

It is certified that error appears in the above-identified patent and that said Letters Patent is hereby corrected as shown below:

In the Specifications:

Col. 1, line 14, before "Serial" delete "Application"

In the Claims:

Col. 105, line 36, claim 1, delete "compromising" and insert -- comprising --

Col. 105, line 41, claim 3, delete "1'C/min." and insert -- 1° C/min. --

Col. 106, line 28, claim 6, delete "compromising" and insert -- comprising --

Col. 106, line 32, claim 7, after "C." delete "degrees."

Signed and Sealed this
Sixth Day of May, 2014

Michelle K. Lee
*Deputy Director of the United States Patent and Trademark Office*

```
                       SEQUENCE LISTING

<160> NUMBER OF SEQ ID NOS: 17

<210> SEQ ID NO 1
<211> LENGTH: 901
<212> TYPE: PRT
<213> ORGANISM: Actinomyces viscosus

<400> SEQUENCE: 1

Met Thr Ser His Ser Pro Phe Ser Arg Arg Leu Pro Ala Leu Leu
 1               5                  10                  15

Gly Ser Leu Pro Leu Ala Ala Thr Gly Leu Ile Ala Ala Pro Pro
                20                  25                  30

Ala His Ala Val Pro Thr Ser Asp Gly Leu Ala Asp Val Thr Ile Thr
            35                  40                  45

Gln Val Asn Ala Pro Ala Asp Gly Leu Tyr Ser Val Gly Asp Val Met
        50                  55                  60

Thr Phe Asn Ile Thr Leu Thr Asn Thr Ser Gly Glu Ala His Ser Tyr
 65                  70                  75                  80

Ala Pro Ala Ser Thr Asn Leu Ser Gly Asn Val Ser Lys Cys Arg Trp
                 85                  90                  95

Arg Asn Val Pro Ala Gly Thr Thr Lys Thr Asp Cys Thr Gly Leu Ala
            100                 105                 110

Thr His Thr Val Thr Ala Glu Asp Leu Lys Ala Gly Gly Phe Thr Pro
        115                 120                 125

Gln Ile Ala Tyr Glu Val Lys Ala Val Glu Tyr Ala Gly Lys Ala Leu
    130                 135                 140

Ser Thr Pro Glu Thr Ile Lys Gly Ala Thr Ser Pro Val Lys Ala Asn
145                 150                 155                 160

Ser Leu Arg Val Glu Ser Ile Thr Pro Ser Ser Ser Gln Glu Asn Tyr
                165                 170                 175

Lys Leu Gly Asp Thr Val Ser Tyr Thr Val Arg Val Arg Ser Val Ser
            180                 185                 190

Asp Lys Thr Ile Asn Val Ala Ala Thr Glu Ser Ser Phe Asp Asp Leu
        195                 200                 205

Gly Arg Gln Cys His Trp Gly Gly Leu Lys Pro Gly Lys Gly Ala Val
    210                 215                 220

Tyr Asn Cys Lys Pro Leu Thr His Thr Ile Thr Gln Ala Asp Val Asp
225                 230                 235                 240

Ala Gly Arg Trp Thr Pro Ser Ile Thr Leu Thr Ala Thr Gly Thr Asp
                245                 250                 255

Gly Ala Thr Leu Gln Thr Leu Thr Ala Thr Gly Asn Pro Ile Asn Val
            260                 265                 270
```

```
Val Gly Asp His Pro Gln Ala Thr Pro Ala Pro Asp Ala Ser
        275                 280                 285

Thr Glu Leu Pro Ala Ser Met Ser Gln Ala Gln His Leu Ala Ala Asn
290                 295                 300

Thr Ala Thr Asp Asn Tyr Arg Ile Pro Ala Ile Thr Thr Ala Pro Asn
305                 310                 315                 320

Gly Asp Leu Leu Ile Ser Tyr Asp Glu Arg Pro Lys Asp Asn Gly Asn
                325                 330                 335

Gly Gly Ser Asp Ala Pro Asn Pro Asn His Ile Val Gln Arg Arg Ser
            340                 345                 350

Thr Asp Gly Gly Lys Thr Trp Ser Ala Pro Thr Tyr Ile His Gln Gly
        355                 360                 365

Thr Glu Thr Gly Lys Lys Val Gly Tyr Ser Asp Pro Ser Tyr Val Val
370                 375                 380

Asp His Gln Thr Gly Thr Ile Phe Asn Phe His Val Lys Ser Tyr Asp
385                 390                 395                 400

Gln Gly Trp Gly Gly Ser Arg Gly Gly Thr Asp Pro Glu Asn Arg Gly
                405                 410                 415

Ile Ile Gln Ala Glu Val Ser Thr Ser Thr Asp Asn Gly Trp Thr Trp
            420                 425                 430

Thr His Arg Thr Ile Thr Ala Asp Ile Thr Lys Asp Lys Pro Trp Thr
        435                 440                 445

Ala Arg Phe Ala Ala Ser Gly Gln Gly Ile Gln Ile Gln His Gly Pro
450                 455                 460

His Ala Gly Arg Leu Val Gln Gln Tyr Thr Ile Arg Thr Ala Gly Gly
465                 470                 475                 480

Ala Val Gln Ala Val Ser Val Tyr Ser Asp Asp His Gly Lys Thr Trp
                485                 490                 495

Gln Ala Gly Thr Pro Ile Gly Thr Gly Met Asp Glu Asn Lys Val Val
            500                 505                 510

Glu Leu Ser Asp Gly Ser Leu Met Leu Asn Ser Arg Ala Ser Asp Gly
        515                 520                 525

Ser Gly Phe Arg Lys Val Ala His Ser Thr Asp Gly Gly Gln Thr Trp
530                 535                 540

Ser Glu Pro Val Ser Asp Lys Asn Leu Pro Asp Ser Val Asp Asn Ala
545                 550                 555                 560

Gln Ile Ile Arg Ala Phe Pro Asn Ala Ala Pro Asp Asp Pro Arg Ala
                565                 570                 575

Lys Val Leu Leu Leu Ser His Ser Pro Asn Pro Arg Pro Trp Ser Arg
            580                 585                 590

Asp Arg Gly Thr Ile Ser Met Ser Cys Asp Asp Gly Ala Ser Trp Thr
        595                 600                 605

Thr Ser Lys Val Phe His Glu Pro Phe Val Gly Tyr Thr Thr Ile Ala
610                 615                 620

Val Gln Ser Asp Gly Ser Ile Gly Leu Leu Ser Glu Asp Ala His Asn
625                 630                 635                 640

Gly Ala Asp Tyr Gly Gly Ile Trp Tyr Arg Asn Phe Thr Met Asn Trp
                645                 650                 655

Leu Gly Glu Gln Cys Gly Gln Lys Pro Ala Glu Pro Ser Pro Ala Pro
            660                 665                 670

Ser Pro Thr Ala Ala Pro Ser Ala Ala Pro Thr Glu Lys Pro Ala Pro
        675                 680                 685

Ser Ala Ala Pro Ser Ala Glu Pro Thr Gln Ala Pro Ala Pro Ser Ser
690                 695                 700
```

```
Ala Pro Glu Pro Ser Ala Ala Pro Glu Pro Ser Ser Ala Pro Ala Pro
705                 710                 715                 720

Glu Pro Thr Thr Ala Pro Ser Thr Glu Pro Thr Pro Ala Pro Ala Pro
            725                 730                 735

Ser Ser Ala Pro Glu Gln Thr Asp Gly Pro Thr Ala Ala Pro Ala Pro
                740                 745                 750

Glu Thr Ser Ser Ala Pro Ala Ala Glu Pro Thr Gln Ala Pro Thr Val
        755                 760                 765

Ala Pro Ser Val Glu Pro Thr Gln Ala Pro Gly Ala Gln Pro Ser Ser
    770                 775                 780

Ala Pro Lys Pro Gly Ala Thr Gly Arg Ala Pro Ser Val Val Asn Pro
785                 790                 795                 800

Lys Ala Thr Gly Ala Ala Thr Glu Pro Gly Thr Pro Ser Ser Ser Ala
            805                 810                 815

Ser Pro Ala Pro Ser Arg Asn Ala Ala Pro Thr Pro Lys Pro Gly Met
                820                 825                 830

Glu Pro Asp Glu Ile Asp Arg Pro Ser Asp Gly Thr Met Ala Gln Pro
        835                 840                 845

Thr Gly Gly Ala Ser Ala Pro Ser Ala Ala Pro Thr Gln Ala Ala Lys
    850                 855                 860

Ala Gly Ser Arg Leu Ser Arg Thr Gly Thr Asn Ala Leu Leu Ile Leu
865                 870                 875                 880

Gly Leu Ala Gly Val Ala Val Val Gly Gly Tyr Leu Leu Leu Arg Ala
            885                 890                 895

Arg Arg Ser Lys Asn
                900

<210> SEQ ID NO 2
<211> LENGTH: 394
<212> TYPE: PRT
<213> ORGANISM: Actinomyces viscosus

<400> SEQUENCE: 2

Gly Asp His Pro Gln Ala Thr Pro Ala Pro Ala Pro Asp Ala Ser Thr
1               5                   10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
    50                  55                  60

Gly Ser Asp Ala Pro Asn Pro Asn His Ile Val Gln Arg Arg Ser Thr
65                  70                  75                  80

Asp Gly Gly Lys Thr Trp Ser Ala Pro Thr Tyr Ile His Gln Gly Thr
            85                  90                  95

Glu Thr Gly Lys Lys Val Gly Tyr Ser Asp Pro Ser Tyr Val Val Asp
            100                 105                 110

His Gln Thr Gly Thr Ile Phe Asn Phe His Val Lys Ser Tyr Asp Gln
        115                 120                 125

Gly Trp Gly Gly Ser Arg Gly Gly Thr Asp Pro Glu Asn Arg Gly Ile
    130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
            165                 170                 175
```

```
Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp Asp His Gly Lys Thr Trp Gln
210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
            245                 250                 255

Gly Phe Arg Lys Val Ala His Ser Thr Asp Gly Gly Gln Thr Trp Ser
        260                 265                 270

Glu Pro Val Ser Asp Lys Asn Leu Pro Asp Ser Val Asp Asn Ala Gln
    275                 280                 285

Ile Ile Arg Ala Phe Pro Asn Ala Ala Pro Asp Asp Pro Arg Ala Lys
290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
            325                 330                 335

Ser Lys Val Phe His Glu Pro Phe Val Gly Tyr Thr Thr Ile Ala Val
        340                 345                 350

Gln Ser Asp Gly Ser Ile Gly Leu Leu Ser Glu Asp Ala His Asn Gly
    355                 360                 365

Ala Asp Tyr Gly Gly Ile Trp Tyr Arg Asn Phe Thr Met Asn Trp Leu
370                 375                 380

Gly Glu Gln Cys Gly Gln Lys Pro Ala Glu
385                 390

<210> SEQ ID NO 3
<211> LENGTH: 24
<212> TYPE: PRT
<213> ORGANISM: Homo sapiens

<400> SEQUENCE: 3

Asn Gly Arg Arg Ile Cys Leu Asp Leu Gln Ala Pro Leu Tyr Lys Lys
1               5                   10                  15

Ile Ile Lys Lys Leu Leu Glu Ser
            20

<210> SEQ ID NO 4
<211> LENGTH: 27
<212> TYPE: PRT
<213> ORGANISM: Homo sapiens

<400> SEQUENCE: 4

Gly Arg Glu Leu Cys Leu Asp Pro Lys Glu Asn Trp Val Gln Arg Val
1               5                   10                  15

Val Glu Lys Phe Leu Lys Arg Ala Glu Asn Ser
            20                  25

<210> SEQ ID NO 5
<211> LENGTH: 34
<212> TYPE: PRT
<213> ORGANISM: Homo sapiens

<400> SEQUENCE: 5

Gln Ile His Phe Phe Phe Ala Lys Leu Asn Cys Arg Leu Tyr Arg Lys
```

```
                1               5                  10                 15
Ala Asn Lys Ser Ser Lys Leu Val Ser Ala Asn Arg Leu Phe Gly Asp
            20                  25                 30

Lys Ser

<210> SEQ ID NO 6
<211> LENGTH: 34
<212> TYPE: PRT
<213> ORGANISM: Homo sapiens

<400> SEQUENCE: 6

Glu Leu Arg Val Arg Leu Ala Ser His Leu Arg Lys Leu Arg Lys Arg
 1               5                  10                 15

Leu Leu Arg Asp Ala Asp Asp Leu Gln Lys Arg Leu Ala Val Tyr Gln
            20                  25                 30

Ala Gly

<210> SEQ ID NO 7
<211> LENGTH: 12
<212> TYPE: PRT
<213> ORGANISM: Homo sapiens

<400> SEQUENCE: 7

Arg Arg Leu Arg Arg Met Glu Ser Glu Ser Glu Ser
 1               5                  10

<210> SEQ ID NO 8
<211> LENGTH: 21
<212> TYPE: PRT
<213> ORGANISM: Homo sapiens

<400> SEQUENCE: 8

Lys Arg Lys Lys Lys Gly Gly Lys Asn Gly Lys Asn Arg Arg Asn Arg
 1               5                  10                 15

Lys Lys Lys Asn Pro
            20

<210> SEQ ID NO 9
<211> LENGTH: 400
<212> TYPE: PRT
<213> ORGANISM: Artificial Sequence
<220> FEATURE:
<223> OTHER INFORMATION: Synthetic construct

<400> SEQUENCE: 9

Met Gly Glu Leu Pro Ala Ser Met Ser Gln Ala Gln His Leu Ala Ala
 1               5                  10                 15

Asn Thr Ala Thr Asp Asn Tyr Arg Ile Pro Ala Ile Thr Thr Ala Pro
            20                  25                 30

Asn Gly Asp Leu Leu Ile Ser Tyr Asp Glu Arg Pro Lys Asp Asn Gly
            35                  40                 45

Asn Gly Gly Ser Asp Ala Pro Asn Pro Asn His Ile Val Gln Arg Arg
      50                  55                 60

Ser Thr Asp Gly Gly Lys Thr Trp Ser Ala Pro Thr Tyr Ile His Gln
65                  70                  75                  80

Gly Thr Glu Thr Gly Lys Lys Val Gly Tyr Ser Asp Pro Ser Tyr Val
                85                  90                 95

Val Asp His Gln Thr Gly Thr Ile Phe Asn Phe His Val Lys Ser Tyr
            100                 105                110

Asp Gln Gly Trp Gly Gly Ser Arg Gly Gly Thr Asp Pro Glu Asn Arg
```

```
            115                 120                 125
Gly Ile Ile Gln Ala Glu Val Ser Thr Ser Thr Asp Asn Gly Trp Thr
130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
                165                 170                 175

Pro His Ala Gly Arg Leu Val Gln Gln Tyr Thr Ile Arg Thr Ala Gly
            180                 185                 190

Gly Ala Val Gln Ala Val Ser Val Tyr Ser Asp Asp His Gly Lys Thr
        195                 200                 205

Trp Gln Ala Gly Thr Pro Ile Gly Thr Gly Met Asp Glu Asn Lys Val
210                 215                 220

Val Glu Leu Ser Asp Gly Ser Leu Met Leu Asn Ser Arg Ala Ser Asp
225                 230                 235                 240

Gly Ser Gly Phe Arg Lys Val Ala His Ser Thr Asp Gly Gly Gln Thr
                245                 250                 255

Trp Ser Glu Pro Val Ser Asp Lys Asn Leu Pro Asp Ser Val Asp Asn
            260                 265                 270

Ala Gln Ile Ile Arg Ala Phe Pro Asn Ala Ala Pro Asp Asp Pro Arg
        275                 280                 285

Ala Lys Val Leu Leu Leu Ser His Ser Pro Asn Pro Arg Pro Trp Ser
290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
            340                 345                 350

Asn Gly Ala Asp Tyr Gly Gly Ile Trp Tyr Arg Asn Phe Thr Met Asn
        355                 360                 365

Trp Leu Gly Glu Gln Cys Gly Gln Lys Pro Ala Lys Arg Lys Lys Lys
370                 375                 380

Gly Gly Lys Asn Gly Lys Asn Arg Arg Asn Lys Lys Asn Pro
385                 390                 395                 400

<210> SEQ ID NO 10
<211> LENGTH: 422
<212> TYPE: PRT
<213> ORGANISM: Artificial Sequence
<220> FEATURE:
<223> OTHER INFORMATION: Synthetic construct

<400> SEQUENCE: 10

Met Val Lys Arg Lys Lys Lys Gly Gly Lys Asn Gly Lys Asn Arg Arg
1               5                   10                  15

Asn Arg Lys Lys Lys Asn Pro Gly Gly Gly Ser Gly Asp His Pro
            20                  25                  30

Gln Ala Thr Pro Ala Pro Ala Pro Asp Ala Ser Thr Glu Leu Pro Ala
        35                  40                  45

Ser Met Ser Gln Ala Gln His Leu Ala Ala Asn Thr Ala Thr Asp Asn
50                  55                  60

Tyr Arg Ile Pro Ala Ile Thr Thr Ala Pro Asn Gly Asp Leu Leu Ile
65                  70                  75                  80

Ser Tyr Asp Glu Arg Pro Lys Asp Asn Gly Asn Gly Gly Ser Asp Ala
                85                  90                  95
```

```
Pro Asn Pro Asn His Ile Val Gln Arg Arg Ser Thr Asp Gly Gly Lys
            100                 105                 110

Thr Trp Ser Ala Pro Thr Tyr Ile His Gln Gly Thr Glu Thr Gly Lys
        115                 120                 125

Lys Val Gly Tyr Ser Asp Pro Ser Tyr Val Val Asp His Gln Thr Gly
130                 135                 140

Thr Ile Phe Asn Phe His Val Lys Ser Tyr Asp Gln Gly Trp Gly Gly
145                 150                 155                 160

Ser Arg Gly Gly Thr Asp Pro Glu Asn Arg Gly Ile Ile Gln Ala Glu
                165                 170                 175

Val Ser Thr Ser Thr Asp Asn Gly Trp Thr Trp Thr His Arg Thr Ile
                180                 185                 190

Thr Ala Asp Ile Thr Lys Asp Lys Pro Trp Thr Ala Arg Phe Ala Ala
            195                 200                 205

Ser Gly Gln Gly Ile Gln Ile Gln His Gly Pro His Ala Gly Arg Leu
210                 215                 220

Val Gln Gln Tyr Thr Ile Arg Thr Ala Gly Gly Ala Val Gln Ala Val
225                 230                 235                 240

Ser Val Tyr Ser Asp Asp His Gly Lys Thr Trp Gln Ala Gly Thr Pro
                245                 250                 255

Ile Gly Thr Gly Met Asp Glu Asn Lys Val Val Glu Leu Ser Asp Gly
            260                 265                 270

Ser Leu Met Leu Asn Ser Arg Ala Ser Asp Gly Ser Gly Phe Arg Lys
        275                 280                 285

Val Ala His Ser Thr Asp Gly Gly Gln Thr Trp Ser Glu Pro Val Ser
290                 295                 300

Asp Lys Asn Leu Pro Asp Ser Val Asp Asn Ala Gln Ile Ile Arg Ala
305                 310                 315                 320

Phe Pro Asn Ala Ala Pro Asp Asp Pro Arg Ala Lys Val Leu Leu Leu
                325                 330                 335

Ser His Ser Pro Asn Pro Arg Pro Trp Ser Arg Asp Arg Gly Thr Ile
            340                 345                 350

Ser Met Ser Cys Asp Asp Gly Ala Ser Trp Thr Thr Ser Lys Val Phe
        355                 360                 365

His Glu Pro Phe Val Gly Tyr Thr Thr Ile Ala Val Gln Ser Asp Gly
370                 375                 380

Ser Ile Gly Leu Leu Ser Glu Asp Ala His Asn Gly Ala Asp Tyr Gly
385                 390                 395                 400

Gly Ile Trp Tyr Arg Asn Phe Thr Met Asn Trp Leu Gly Glu Gln Cys
                405                 410                 415

Gly Gln Lys Pro Ala Glu
            420

<210> SEQ ID NO 11
<211> LENGTH: 415
<212> TYPE: PRT
<213> ORGANISM: Artificial Sequence
<220> FEATURE:
<223> OTHER INFORMATION: Synthetic construct

<400> SEQUENCE: 11

Met Gly Glu Leu Pro Ala Ser Met Ser Gln Ala Gln His Leu Ala Ala
1               5                   10                  15

Asn Thr Ala Thr Asp Asn Tyr Arg Ile Pro Ala Ile Thr Thr Ala Pro
            20                  25                  30
```

Asn Gly Asp Leu Leu Ile Ser Tyr Asp Glu Arg Pro Lys Asp Asn Gly
             35                  40                  45

Asn Gly Gly Ser Asp Ala Pro Asn Pro Asn His Ile Val Gln Arg Arg
 50                  55                  60

Ser Thr Asp Gly Gly Lys Thr Trp Ser Ala Pro Thr Tyr Ile His Gln
 65                  70                  75                  80

Gly Thr Glu Thr Gly Lys Lys Val Gly Tyr Ser Asp Pro Ser Tyr Val
                 85                  90                  95

Val Asp His Gln Thr Gly Thr Ile Phe Asn Phe His Val Lys Ser Tyr
            100                 105                 110

Asp Gln Gly Trp Gly Gly Ser Arg Gly Gly Thr Asp Pro Glu Asn Arg
            115                 120                 125

Gly Ile Ile Gln Ala Glu Val Ser Thr Ser Thr Asp Asn Gly Trp Thr
130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
                165                 170                 175

Pro His Ala Gly Arg Leu Val Gln Tyr Thr Ile Arg Thr Ala Gly
            180                 185                 190

Gly Ala Val Gln Ala Val Ser Val Tyr Ser Asp Asp His Gly Lys Thr
            195                 200                 205

Trp Gln Ala Gly Thr Pro Ile Gly Thr Gly Met Asp Glu Asn Lys Val
210                 215                 220

Val Glu Leu Ser Asp Gly Ser Leu Met Leu Asn Ser Arg Ala Ser Asp
225                 230                 235                 240

Gly Ser Gly Phe Arg Lys Val Ala His Ser Thr Asp Gly Gly Gln Thr
                245                 250                 255

Trp Ser Glu Pro Val Ser Asp Lys Asn Leu Pro Asp Ser Val Asp Asn
            260                 265                 270

Ala Gln Ile Ile Arg Ala Phe Pro Asn Ala Ala Pro Asp Asp Pro Arg
            275                 280                 285

Ala Lys Val Leu Leu Leu Ser His Ser Pro Asn Pro Arg Pro Trp Ser
290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
            340                 345                 350

Asn Gly Ala Asp Tyr Gly Gly Ile Trp Tyr Arg Asn Phe Thr Met Asn
            355                 360                 365

Trp Leu Gly Glu Gln Cys Gly Gln Lys Pro Ala Glu Pro Ser Pro Ala
370                 375                 380

Pro Ser Pro Thr Ala Ala Pro Ser Ala Ala Lys Arg Lys Lys Lys Gly
385                 390                 395                 400

Gly Lys Asn Gly Lys Asn Arg Arg Asn Arg Lys Lys Asn Pro
                405                 410                 415

<210> SEQ ID NO 12
<211> LENGTH: 404
<212> TYPE: PRT
<213> ORGANISM: Artificial Sequence
<220> FEATURE:
<223> OTHER INFORMATION: Synthetic construct

<400> SEQUENCE: 12

```
Met Gly His His His His His His Leu Glu Gly Asp His Pro Gln Ala
 1               5                  10                  15

Thr Pro Ala Pro Ala Pro Asp Ala Ser Thr Glu Leu Pro Ala Ser Met
             20                  25                  30

Ser Gln Ala Gln His Leu Ala Ala Asn Thr Ala Thr Asp Asn Tyr Arg
         35                  40                  45

Ile Pro Ala Ile Thr Thr Ala Pro Asn Gly Asp Leu Leu Ile Ser Tyr
 50                  55                  60

Asp Glu Arg Pro Lys Asp Asn Gly Asn Gly Gly Ser Asp Ala Pro Asn
 65                  70                  75                  80

Pro Asn His Ile Val Gln Arg Arg Ser Thr Asp Gly Gly Lys Thr Trp
             85                  90                  95

Ser Ala Pro Thr Tyr Ile His Gln Gly Thr Glu Thr Gly Lys Lys Val
            100                 105                 110

Gly Tyr Ser Asp Pro Ser Tyr Val Val Asp His Gln Thr Gly Thr Ile
            115                 120                 125

Phe Asn Phe His Val Lys Ser Tyr Asp Gln Gly Trp Gly Gly Ser Arg
    130                 135                 140

Gly Gly Thr Asp Pro Glu Asn Arg Gly Ile Ile Gln Ala Glu Val Ser
145                 150                 155                 160

Thr Ser Thr Asp Asn Gly Trp Thr Trp Thr His Arg Thr Ile Thr Ala
                165                 170                 175

Asp Ile Thr Lys Asp Lys Pro Trp Thr Ala Arg Phe Ala Ala Ser Gly
            180                 185                 190

Gln Gly Ile Gln Ile Gln His Gly Pro His Ala Gly Arg Leu Val Gln
        195                 200                 205

Gln Tyr Thr Ile Arg Thr Ala Gly Ala Val Gln Ala Val Ser Val
    210                 215                 220

Tyr Ser Asp Asp His Gly Lys Thr Trp Gln Ala Gly Thr Pro Ile Gly
225                 230                 235                 240

Thr Gly Met Asp Glu Asn Lys Val Val Glu Leu Ser Asp Gly Ser Leu
                245                 250                 255

Met Leu Asn Ser Arg Ala Ser Asp Gly Ser Gly Phe Arg Lys Val Ala
            260                 265                 270

His Ser Thr Asp Gly Gly Gln Thr Trp Ser Glu Pro Val Ser Asp Lys
        275                 280                 285

Asn Leu Pro Asp Ser Val Asp Asn Ala Gln Ile Ile Arg Ala Phe Pro
    290                 295                 300

Asn Ala Ala Pro Asp Asp Pro Arg Ala Lys Val Leu Leu Leu Ser His
305                 310                 315                 320

Ser Pro Asn Pro Arg Pro Trp Ser Arg Asp Arg Gly Thr Ile Ser Met
                325                 330                 335

Ser Cys Asp Asp Gly Ala Ser Trp Thr Thr Ser Lys Val Phe His Glu
            340                 345                 350

Pro Phe Val Gly Tyr Thr Thr Ile Ala Val Gln Ser Asp Gly Ser Ile
        355                 360                 365

Gly Leu Leu Ser Glu Asp Ala His Asn Gly Ala Asp Tyr Gly Gly Ile
    370                 375                 380

Trp Tyr Arg Asn Phe Thr Met Asn Trp Leu Gly Glu Gln Cys Gly Gln
385                 390                 395                 400

Lys Pro Ala Glu
```

```
<210> SEQ ID NO 13
<211> LENGTH: 416
<212> TYPE: PRT
<213> ORGANISM: Artificial Sequence
<220> FEATURE:
<223> OTHER INFORMATION: Synthetic construct

<400> SEQUENCE: 13
```

| | | | | | | | | | | | | | | | |
|---|---|---|---|---|---|---|---|---|---|---|---|---|---|---|---|
| Met | Lys | Arg | Lys | Lys | Gly | Gly | Lys | Asn | Gly | Lys | Asn | Arg | Arg | Asn | |
| 1 | | | | 5 | | | | | 10 | | | | | 15 | |
| Arg | Lys | Lys | Lys | Asn | Pro | Gly | Asp | His | Pro | Gln | Ala | Thr | Pro | Ala | Pro |
| | | | 20 | | | | | 25 | | | | | 30 | | |
| Ala | Pro | Asp | Ala | Ser | Thr | Glu | Leu | Pro | Ala | Ser | Met | Ser | Gln | Ala | Gln |
| | | 35 | | | | | 40 | | | | | 45 | | | |
| His | Leu | Ala | Ala | Asn | Thr | Ala | Thr | Asp | Asn | Tyr | Arg | Ile | Pro | Ala | Ile |
| | 50 | | | | | 55 | | | | | 60 | | | | |
| Thr | Thr | Ala | Pro | Asn | Gly | Asp | Leu | Leu | Ile | Ser | Tyr | Asp | Glu | Arg | Pro |
| 65 | | | | | 70 | | | | 75 | | | | | 80 | |
| Lys | Asp | Asn | Gly | Asn | Gly | Ser | Asp | Ala | Pro | Asn | Pro | Asn | His | Ile | |
| | | | | 85 | | | | 90 | | | | | 95 | | |
| Val | Gln | Arg | Arg | Ser | Thr | Asp | Gly | Gly | Lys | Thr | Trp | Ser | Ala | Pro | Thr |
| | | | 100 | | | | | 105 | | | | | 110 | | |
| Tyr | Ile | His | Gln | Gly | Thr | Glu | Thr | Gly | Lys | Lys | Val | Gly | Tyr | Ser | Asp |
| | | 115 | | | | | 120 | | | | | 125 | | | |
| Pro | Ser | Tyr | Val | Val | Asp | His | Gln | Thr | Gly | Thr | Ile | Phe | Asn | Phe | His |
| | 130 | | | | | 135 | | | | | 140 | | | | |
| Val | Lys | Ser | Tyr | Asp | Gln | Gly | Trp | Gly | Gly | Ser | Arg | Gly | Gly | Thr | Asp |
| 145 | | | | | 150 | | | | | 155 | | | | | 160 |
| Pro | Glu | Asn | Arg | Gly | Ile | Ile | Gln | Ala | Glu | Val | Ser | Thr | Ser | Thr | Asp |
| | | | 165 | | | | | 170 | | | | | 175 | | |
| Asn | Gly | Trp | Thr | Trp | Thr | His | Arg | Thr | Ile | Thr | Ala | Asp | Ile | Thr | Lys |
| | | | 180 | | | | | 185 | | | | | 190 | | |
| Asp | Lys | Pro | Trp | Thr | Ala | Arg | Phe | Ala | Ala | Ser | Gly | Gln | Gly | Ile | Gln |
| | | 195 | | | | | 200 | | | | | 205 | | | |
| Ile | Gln | His | Gly | Pro | His | Ala | Gly | Arg | Leu | Val | Gln | Gln | Tyr | Thr | Ile |
| | 210 | | | | | 215 | | | | | 220 | | | | |
| Arg | Thr | Ala | Gly | Gly | Ala | Val | Gln | Ala | Val | Ser | Val | Tyr | Ser | Asp | Asp |
| 225 | | | | | 230 | | | | | 235 | | | | | 240 |
| His | Gly | Lys | Thr | Trp | Gln | Ala | Gly | Thr | Pro | Ile | Gly | Thr | Gly | Met | Asp |
| | | | 245 | | | | | 250 | | | | | 255 | | |
| Glu | Asn | Lys | Val | Val | Glu | Leu | Ser | Asp | Gly | Ser | Leu | Met | Leu | Asn | Ser |
| | | | 260 | | | | | 265 | | | | | 270 | | |
| Arg | Ala | Ser | Asp | Gly | Ser | Gly | Phe | Arg | Lys | Val | Ala | His | Ser | Thr | Asp |
| | | 275 | | | | | 280 | | | | | 285 | | | |
| Gly | Gly | Gln | Thr | Trp | Ser | Glu | Pro | Val | Ser | Asp | Lys | Asn | Leu | Pro | Asp |
| | 290 | | | | | 295 | | | | | 300 | | | | |
| Ser | Val | Asp | Asn | Ala | Gln | Ile | Ile | Arg | Ala | Phe | Pro | Asn | Ala | Ala | Pro |
| 305 | | | | | 310 | | | | | 315 | | | | | 320 |
| Asp | Asp | Pro | Arg | Ala | Lys | Val | Leu | Leu | Leu | Ser | His | Ser | Pro | Asn | Pro |
| | | | | 325 | | | | | 330 | | | | | 335 | |
| Arg | Pro | Trp | Ser | Arg | Asp | Arg | Gly | Thr | Ile | Ser | Met | Ser | Cys | Asp | Asp |
| | | | 340 | | | | | 345 | | | | | 350 | | |
| Gly | Ala | Ser | Trp | Thr | Thr | Ser | Lys | Val | Phe | His | Glu | Pro | Phe | Val | Gly |
| | | 355 | | | | | 360 | | | | | 365 | | | |
| Tyr | Thr | Thr | Ile | Ala | Val | Gln | Ser | Asp | Gly | Ser | Ile | Gly | Leu | Leu | Ser |
| | 370 | | | | | 375 | | | | | 380 | | | | |

```
Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
            405                 410                 415
```

<210> SEQ ID NO 14
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 14

```
Met Xaa Xaa Lys Arg Lys Lys Lys Gly Gly
1               5                   10
```

<210> SEQ ID NO 15
<211> LENGTH: 374
<212> TYPE: PRT
<213> ORGANISM: Homo sapiens
<220> FEATURE:
<223> OTHER INFORMATION: protease inhibitor 8 (PI8) (Serpin B8)

<400> SEQUENCE: 15

```
Met Asp Asp Leu Cys Glu Ala Asn Gly Thr Phe Ala Ile Ser Leu Phe
1               5                   10                  15

Lys Ile Leu Gly Glu Glu Asp Asn Ser Arg Asn Val Phe Phe Ser Pro
            20                  25                  30

Met Ser Ile Ser Ser Ala Leu Ala Met Val Phe Met Gly Ala Lys Gly
        35                  40                  45

Ser Thr Ala Ala Gln Met Ser Gln Ala Leu Cys Leu Tyr Lys Asp Gly
    50                  55                  60

Asp Ile His Arg Gly Phe Gln Ser Leu Leu Ser Glu Val Asn Arg Thr
65                  70                  75                  80

Gly Thr Gln Tyr Leu Leu Arg Thr Ala Asn Arg Leu Phe Gly Glu Lys
                85                  90                  95

Thr Cys Asp Phe Leu Pro Asp Phe Lys Glu Tyr Cys Gln Lys Phe Tyr
            100                 105                 110

Gln Ala Glu Leu Glu Glu Leu Ser Phe Ala Glu Asp Thr Glu Glu Cys
        115                 120                 125

Arg Lys His Ile Asn Asp Trp Val Ala Glu Lys Thr Glu Gly Lys Ile
    130                 135                 140

Ser Glu Val Leu Asp Ala Gly Thr Val Asp Pro Leu Thr Lys Leu Val
145                 150                 155                 160

Leu Val Asn Ala Ile Tyr Phe Lys Gly Lys Trp Asn Glu Gln Phe Asp
                165                 170                 175

Arg Lys Tyr Thr Arg Gly Met Leu Phe Lys Thr Asn Glu Glu Lys Lys
            180                 185                 190

Thr Val Gln Met Met Phe Lys Glu Ala Lys Phe Lys Met Gly Tyr Ala
        195                 200                 205

Asp Glu Val His Thr Gln Val Leu Glu Leu Pro Tyr Val Glu Glu Glu
    210                 215                 220

Leu Ser Met Val Ile Leu Leu Pro Asp Asp Asn Thr Asp Leu Ala Val
225                 230                 235                 240

Val Glu Lys Ala Leu Thr Tyr Glu Lys Phe Lys Ala Trp Thr Asn Ser
```

```
                    245                 250                 255
Glu Lys Leu Thr Lys Ser Lys Val Gln Val Phe Leu Pro Arg Leu Lys
            260                 265                 270

Leu Glu Glu Ser Tyr Asp Leu Glu Pro Phe Leu Arg Arg Leu Gly Met
        275                 280                 285

Ile Asp Ala Phe Asp Glu Ala Lys Ala Asp Phe Ser Gly Met Ser Thr
    290                 295                 300

Glu Lys Asn Val Pro Leu Ser Lys Val Ala His Lys Cys Phe Val Glu
305                 310                 315                 320

Val Asn Glu Glu Gly Thr Glu Ala Ala Ala Thr Ala Val Val Arg
                325                 330                 335

Asn Ser Arg Cys Ser Arg Met Glu Pro Arg Phe Cys Ala Asp His Pro
            340                 345                 350

Phe Leu Phe Phe Ile Arg Arg His Lys Thr Asn Cys Ile Leu Phe Cys
        355                 360                 365

Gly Arg Phe Ser Ser Pro
    370

<210> SEQ ID NO 16
<211> LENGTH: 4176
<212> TYPE: DNA
<213> ORGANISM: Artificial Sequence
<220> FEATURE:
<223> OTHER INFORMATION: Plasmid vector PTrc99A

<400> SEQUENCE: 16
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagaccatgg aattcgagct cggtacccgg ggatcctcta     300
gagtcgacct gcaggcatgc aagcttggct gttttggcgg atgagagaag attttcagcc     360
tgatacagat taaatcagaa cgcagaagcg gtctgataaa acagaatttg cctggcggca     420
gtagcgcggt ggtcccacct gaccccatgc cgaactcaga agtgaaacgc cgtagcgccg     480
atggtagtgt ggggtctccc catgcgagag tagggaactg ccaggcatca ataaaacga      540 aaggctcagt cgaaagactg ggcctttcgt tttatctgtt gtttgtcggt gaacgctctc     600
ctgagtagga caaatccgcc gggagcggat ttgaacgttg cgaagcaacg gcccggaggg     660
tggcgggcag gacgcccgcc ataaactgcc aggcatcaaa ttaagcagaa ggccatcctg     720
acggatggcc ttttgcgtt tctacaaact cttttgttt attttctaa atacattcaa        780 atatgtatcc gctcatgaga caataaccct gataaatgct tcaataatat tgaaaagga     840 agagtatgag tattcaacat ttccgtgtcg cccttattcc cttttttgcg cattttgcc      900 ttcctgtttt tgctcacccca gaaacgctgg tgaaagtaaa agatgctgaa gatcagttgg    960
gtgcacgagt gggttacatc gaactggatc tcaacagcgg taagatcctt gagagttttc    1020
gccccgaaga acgttttcca atgatgagca cttttaaagt tctgctatgt ggcgcggtat    1080
tatcccgtgt tgacgccggg caagagcaac tcggtcgccg catacactat tctcagaatg    1140
acttggttga gtactcacca gtcacagaaa agcatcttac ggatggcatg acagtaagag    1200
aattatgcag tgctgccata accatgagtg ataacactgc ggccaactta cttctgacaa    1260
cgatcggagg accgaaggag ctaaccgctt ttttgcacaa catgggggat catgtaactc    1320
```

-continued

```
gccttgatcg ttgggaaccg gagctgaatg aagccatacc aaacgacgag cgtgacacca    1380
cgatgcctac agcaatggca acaacgttgc gcaaactatt aactggcgaa ctacttactc    1440
tagcttcccg gcaacaatta atagactgga tggaggcgga taaagttgca ggaccacttc    1500
tgcgctcggc ccttccggct ggctggttta ttgctgataa atctggagcc ggtgagcgtg    1560
ggtctcgcgg tatcattgca gcactggggc cagatggtaa gccctcccgt atcgtagtta    1620
tctacacgac ggggagtcag gcaactatgg atgaacgaaa tagacagatc gctgagatag    1680
gtgcctcact gattaagcat tggtaactgt cagaccaagt ttactcatat atactttaga    1740
ttgatttaaa acttcatttt taatttaaaa ggatctaggt gaagatcctt tttgataatc    1800
tcatgaccaa aatcccttaa cgtgagtttt cgttccactg agcgtcagac cccgtagaaa    1860
agatcaaagg atcttcttga gatcctttt ttctgcgcgt aatctgctgc ttgcaaacaa    1920
aaaaaccacc gctaccagcg gtggtttgtt tgccggatca agagctacca actctttttc    1980
cgaaggtaac tggcttcagc agagcgcaga taccaaatac tgtccttcta gtgtagccgt    2040
agttaggcca ccacttcaag aactctgtag caccgcctac atacctcgct ctgctaatcc    2100
tgttaccagt ggctgctgcc agtggcgata agtcgtgtct taccgggttg actcaagac    2160
gatagttacc ggataaggcg cagcggtcgg gctgaacggg gggttcgtgc acacagccca    2220
gcttggagcg aacgacctac accgaactga gatacctaca gcgtgagcta tgagaaagcg    2280
ccacgcttcc cgaagggaga aaggcggaca ggtatccggt aagcggcagg gtcggaacag    2340
gagagcgcac gagggagctt ccaggggaa acgcctggta tctttatagt cctgtcgggt    2400
ttcgccacct ctgacttgag cgtcgatttt tgtgatgctc gtcaggggg cggagcctat    2460
ggaaaaacgc cagcaacgcg gccttttac ggttcctggc cttttgctgg ccttttgctc    2520
acatgttctt tcctgcgtta tcccctgatt ctgtggataa ccgtattacc gcctttgagt    2580
gagctgatac cgctcgccgc agccgaacga ccgagcgcag cgagtcagtg agcgaggaag    2640
cggaagagcg cctgatgcgg tattttctcc ttacgcatct gtgcggtatt tcacaccgca    2700
tatggtgcac tctcagtaca atctgctctg atgccgcata gttaagccag tatacactcc    2760
gctatcgcta cgtgactggg tcatggctgc gccccgacac ccgccaacac ccgctgacgc    2820
gccctgacgg gcttgtctgc tcccggcatc cgcttacaga caagctgtga ccgtctccgg    2880
gagctgcatg tgtcagaggt tttcaccgtc atcaccgaaa cgcgcgaggc agcagatcaa    2940
ttcgcgcgcg aaggcgaagc ggcatgcatt tacgttgaca ccatcgaatg gtgcaaaacc    3000
tttcgcggta tggcatgata gcgcccggaa gagagtcaat tcagggtggt gaatgtgaaa    3060
ccagtaacgt tatacgatgt cgcagagtat gccggtgtct cttatcagac cgtttcccgc    3120
gtggtgaacc aggccagcca cgtttctgcg aaaacgcggg aaaaagtgga agcggcgatg    3180
gcggagctga attacattcc caaccgcgtg gcacaacaac tggcgggcaa acagtcgttg    3240
ctgattggcg ttgccacctc cagtctggcc ctgcacgcgc cgtcgcaaat gtcgcggcg    3300
attaaatctc gcgccgatca actgggtgcc agcgtggtgg tgtcgatggt agaacgaagc    3360
ggcgtcgaag cctgtaaagc ggcggtgcac aatcttctcg cgcaacgcgt cagtgggctg    3420
atcattaact atccgctgga tgaccaggat gccattgctg tggaagctgc ctgcactaat    3480
gttccggcgt tatttcttga tgtctctgac cagacaccca tcaacagtat tattttctcc    3540
catgaagacg gtacgcgact gggcgtggag catctggtcg cattgggtca ccagcaaatc    3600
gcgctgttag cgggcccatt aagttctgtc tcggcgcgtc tgcgtctggc tggctggcat    3660
aaatatctca ctcgcaatca aattcagccg atagcggaac gggaaggcga ctggagtgcc    3720
```

```
atgtccggtt ttcaacaaac catgcaaatg ctgaatgagg gcatcgttcc cactgcgatg   3780
ctggttgcca acgatcagat ggcgctgggc gcaatgcgcg ccattaccga gtccgggctg   3840
cgcgttggtg cggatatctc ggtagtggga tacgacgata ccgaagacag ctcatgttat   3900
atcccgccgt taaccaccat caaacaggat tttcgcctgc tggggcaaac cagcgtggac   3960
cgcttgctgc aactctctca gggccaggcg gtgaagggca atcagctgtt gcccgtctca   4020
ctggtgaaaa gaaaaaccac cctggcgccc aatacgcaaa ccgcctctcc ccgcgcgttg   4080
gccgattcat taatgcagct ggcacgacag gtttcccgac tggaaagcgg gcagtgagcg   4140
caacgcaatt aatgtgagtt agcgcgaatt gatctg                             4176
```

<210> SEQ ID NO 17
<211> LENGTH: 415
<212> TYPE: PRT
<213> ORGANISM: Artificial Sequence
<220> FEATURE:
<223> OTHER INFORMATION: DAS181

<400> SEQUENCE: 17

```
Met Gly Asp His Pro Gln Ala Thr Pro Ala Pro Ala Pro Asp Ala Ser
  1               5                  10                  15

Thr Glu Leu Pro Ala Ser Met Ser Gln Ala Gln His Leu Ala Ala Asn
             20                  25                  30

Thr Ala Thr Asp Asn Tyr Arg Ile Pro Ala Ile Thr Thr Ala Pro Asn
         35                  40                  45

Gly Asp Leu Leu Ile Ser Tyr Asp Glu Arg Pro Lys Asp Asn Gly Asn
     50                  55                  60

Gly Gly Ser Asp Ala Pro Asn Pro Asn His Ile Val Gln Arg Arg Ser
 65                  70                  75                  80

Thr Asp Gly Gly Lys Thr Trp Ser Ala Pro Thr Tyr Ile His Gln Gly
                 85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp Asp His Gly Lys Thr Trp
    210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Asp Ser Val Asp Asn Ala
        275                 280                 285
```

-continued

```
Gln Ile Ile Arg Ala Phe Pro Asn Ala Ala Pro Asp Asp Pro Arg Ala
    290             295             300
Lys Val Leu Leu Leu Ser His Ser Pro Asn Pro Arg Pro Trp Ser Arg
305             310             315             320
Asp Arg Gly Thr Ile Ser Met Ser Cys Asp Asp Gly Ala Ser Trp Thr
            325             330             335
Thr Ser Lys Val Phe His Glu Pro Phe Val Gly Tyr Thr Thr Ile Ala
            340             345             350
Val Gln Ser Asp Gly Ser Ile Gly Leu Leu Ser Glu Asp Ala His Asn
        355             360             365
Gly Ala Asp Tyr Gly Gly Ile Trp Tyr Arg Asn Phe Thr Met Asn Trp
    370             375             380
Leu Gly Glu Gln Cys Gly Gln Lys Pro Ala Lys Arg Lys Lys Lys Gly
385             390             395             400
Gly Lys Asn Gly Lys Asn Arg Arg Asn Arg Lys Lys Lys Asn Pro
            405             410             415
```